US012018075B2

(12) United States Patent
Randolph

(10) Patent No.: US 12,018,075 B2
(45) Date of Patent: Jun. 25, 2024

(54) CHROMATOGRAPHY COLUMN QUALIFICATION IN MANUFACTURING METHODS FOR PRODUCING ANTI-TNF ANTIBODY COMPOSITIONS

(71) Applicant: Janssen Biotech, Inc., Horsham, PA (US)

(72) Inventor: Paul Randolph, Malvern, PA (US)

(73) Assignee: Janssen Biotech, Inc., Horsham, PA (US)

( * ) Notice: Subject to any disclaimer, the term of this patent is extended or adjusted under 35 U.S.C. 154(b) by 1076 days.

(21) Appl. No.: 16/389,055

(22) Filed: Apr. 19, 2019

(65) Prior Publication Data

US 2019/0324000 A1 Oct. 24, 2019

Related U.S. Application Data

(60) Provisional application No. 62/660,340, filed on Apr. 20, 2018.

(51) Int. Cl.
*C07K 16/24* (2006.01)
*B01D 15/16* (2006.01)
*B01D 15/20* (2006.01)
*B01D 15/36* (2006.01)
*B01D 15/38* (2006.01)
*C07K 1/18* (2006.01)
*C07K 1/22* (2006.01)
*G01N 30/56* (2006.01)
*G01N 30/86* (2006.01)
*G01N 35/00* (2006.01)

(52) U.S. Cl.
CPC .......... *C07K 16/244* (2013.01); *B01D 15/166* (2013.01); *B01D 15/20* (2013.01); *B01D 15/206* (2013.01); *B01D 15/362* (2013.01); *B01D 15/363* (2013.01); *B01D 15/3809* (2013.01); *C07K 1/18* (2013.01); *C07K 1/22* (2013.01); *C07K 16/241* (2013.01); *G01N 30/56* (2013.01); *G01N 30/8665* (2013.01); *G01N 35/00623* (2013.01); *C07K 2317/24* (2013.01); *C07K 2317/31* (2013.01); *C07K 2317/565* (2013.01); *G01N 2030/562* (2013.01)

(58) Field of Classification Search
None
See application file for complete search history.

(56) References Cited

U.S. PATENT DOCUMENTS

| | | | |
|---|---|---|---|
| 4,399,216 A | 8/1983 | Axel et al. | |
| 4,634,665 A | 1/1987 | Axel et al. | |
| 4,656,134 A | 4/1987 | Ringold | |
| 4,956,288 A | 9/1990 | Barsoum | |
| 5,122,464 A | 6/1992 | Wilson et al. | |
| 5,149,636 A | 9/1992 | Axel et al. | |
| 5,168,062 A | 12/1992 | Stinski | |
| 5,179,017 A | 1/1993 | Axel et al. | |
| 5,266,491 A | 11/1993 | Nagata | |
| 5,385,839 A | 1/1995 | Stinski | |
| 5,410,928 A | 5/1995 | Bakermans | |
| 5,580,734 A | 12/1996 | Treco et al. | |
| 5,641,670 A | 6/1997 | Treco et al. | |
| 5,733,761 A | 3/1998 | Treco | |
| 5,770,359 A | 6/1998 | Wilson et al. | |
| 5,827,739 A | 10/1998 | Wilson et al. | |
| 6,171,825 B1 | 1/2001 | Chan | |
| 6,936,441 B2 | 8/2005 | Reiter | |
| 8,410,928 B2 | 4/2013 | Ganguly et al. | |
| 8,895,709 B2 | 11/2014 | Hickman | |
| 9,047,438 B2 | 6/2015 | Belousov et al. | |
| 9,518,082 B2 | 12/2016 | Allison | |
| 2007/0021277 A1 | 1/2007 | Kuo | |
| 2007/0215548 A1 | 9/2007 | Zhou | |
| 2007/0292442 A1* | 12/2007 | Wan | A61P 17/06 530/387.3 |
| 2008/0000904 A1 | 1/2008 | Vovan | |
| 2011/0147312 A1 | 6/2011 | Cunnien | |

(Continued)

FOREIGN PATENT DOCUMENTS

WO 2007077217 7/2007
WO 2007117490 A2 10/2007
(Continued)

OTHER PUBLICATIONS

US 5,733,746 A, 03/1998, Treco (withdrawn)
(Continued)

*Primary Examiner* — Ryan B Huang
(74) *Attorney, Agent, or Firm* — Riverside Law LLP

(57) ABSTRACT

A method of operating a chromatography column is described for use in methods of manufacture for producing anti-TNF antibodies, e.g., the anti-TNFα antibody SIMPONI® (golimumab). This method involves collecting column outlet signal and accumulated flow parameters at two or more intervals of at least one mobile phase transition front during operation of the chromatography column comprising column packing. A model gamma cumulative distribution curve is calculated based on the collected column outlet signal and accumulated flow parameters for the at least one mobile phase transition front. A height equivalent theoretical plate (HETP) value is calculated for the at least one mobile phase transition front using parameters of the model gamma cumulative distribution curve and the quality of the chromatography column packing is assessed based on the calculated HETP value.

20 Claims, 30 Drawing Sheets
Specification includes a Sequence Listing.

(56) References Cited

U.S. PATENT DOCUMENTS

| | | | |
|---|---|---|---|
| 2012/0282654 A1* | 11/2012 | Yao | C07K 16/2863 435/69.6 |
| 2013/0281672 A1 | 10/2013 | Belousov | |
| 2013/0338344 A1* | 12/2013 | Ramasubramanyan | C12P 21/00 530/416 |
| 2014/0288272 A1* | 9/2014 | Allison | B01D 15/3809 435/69.6 |
| 2017/0247444 A1 | 8/2017 | Hedrick | |

FOREIGN PATENT DOCUMENTS

| | | |
|---|---|---|
| WO | 2009094203 A2 | 7/2009 |
| WO | 2018024770 A1 | 2/2018 |

OTHER PUBLICATIONS

Boshart, et al., "A very strong enhancer is located upstream of an immediate early gene of human cytomegalovirus." Cell, vol. 41, No. 521-530, (1985).

Cullen, et al., "Functional analysis of the transcription control region located within the avian retroviral long terminal repeat.", Molec. Cell. Biol., vol. 5, pp. 438-447 (1985).

Alt, et al., "Selective multiplication of dihydrofolate reductase genes in methotrexate-resistant variants of cultured murine cells.", J. Biol. Chem., vol. 25, No. 253, pp. 1357-1370 (1978).

Dolinar, et al., "A Guide to Follow-on Biologics and Biosimilars With a Focus on Insulin." Endocrine Practice, vol. 24, No. 2, pp. 195-204, (Feb. 2018).

Gossen, et al., "Tight control of gene expression in mammalian cells by tetracycline-responsive promoters.", Proc. Natl. Acad. Sci. USA, vol. 89, pp. 5547-5551 (1992).

Kunert, et al., "Advances in recombinant antibody manufacturing." Appl Microbiol Biotechnol., vol. 100, No. 8, pp. 3451-3461, (2016).

Larson, et al., "Use of Process Data to Assess Chromatographic Performance in Production-Scale Protein Purification 10 Columns,", Biotechnol. Prog., vol. 19, pp. 485-492 (2003).

Page, et al., "High level expression of the humanized monoclonal antibody Campath-1H in Chinese hamster ovary cells." Biotechnology, vol. 9, pp. 64-68 (1991).

Sprague, et al., "Expression of a recombinant DNA gene coding for the vesicular stomatitis virus nucleocapsid protein.", J. Virol., vol. 45, pp. 773-781 (1983).

Van Deemter, et al., "Longitudinal Diffusion and Resistance to Mass Transfer as Causes of Nonideality in Chromatography,", Chem. Engng. Sci. vol. 5, pp. 271-289, (1956).

Gritti, et al., "The rationale for the optimum efficiency of columns packed with new 1.9 µm fully porous Titan-C18 particles—A detaled investigation of the intra-particle diffusivity", Journal of Chromatography A., vol. 1355, pp. 164-178, (Jun. 2014).

Bork, et al., "Online Integrity monitoring in the Protein A step of mAb Production Processes-increasing reliability and process robustness", Biotechnology Progress, vol. 30, No. 2, pp. 383-390, (Jan. 2014).

Jayapal et al., "Recombinant protein therapeutics from CHO cells-20 years and counting", Chemical Engineering Progress, vol. 103 (2007), pp. 40-47.

* cited by examiner

Overview of Manufacturing Process - Process Stages

SEQUENCE LISTING

<160> NUMBER OF SEQ ID NOS: 2

<210> SEQ ID NO 1
<211> LENGTH: 456
<212> TYPE: PRT
<213> ORGANISM: Homo sapiens

<400> SEQUENCE: 1

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Arg Asp Arg Gly Ile Ala Ala Gly Gly Asn Tyr Tyr Tyr Gly
            100                 105                 110

Met Asp Val Trp Gly Gln Gly Thr Thr Val Thr Val Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 2
<211> LENGTH: 215
<212> TYPE: PRT
<213> ORGANISM: Homo sapiens

<400> SEQUENCE: 2

Glu Ile Val Leu Thr Gln Ser Pro Ala Thr Leu Ser Leu Ser Pro Gly
```

-continued

```
1               5                   10                  15
Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
            50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

CHROMATOGRAPHY COLUMN QUALIFICATION IN MANUFACTURING METHODS FOR PRODUCING ANTI-TNF ANTIBODY COMPOSITIONS

CROSS REFERENCE TO RELATED APPLICATION

This application claims priority to U.S. Provisional Application No. 62/660,340, filed Apr. 20, 2018, which is incorporated herein by reference in its entirety.

FIELD OF THE INVENTION

The present invention relates to a method of chromatography column qualification in methods of manufacture for producing anti-TNF antibodies, e.g., the anti-TNFα antibody SIMPONI® (golimumab), and specific pharmaceutical compositions of the antibody.

REFERENCE TO SEQUENCE LISTING SUBMITTED ELECTRONICALLY

This application contains a sequence listing, which is submitted electronically via EFS-Web as an ASCII formatted sequence listing with a file name "JBI6083USNP1 Sequences", creation date of Apr. 12, 2019 and having a size of 7 kb. The sequence listing submitted via EFS-Web is part of the specification and is herein incorporated by reference in its entirety.

BACKGROUND OF THE INVENTION

Column chromatography is an important technique used in purification processes to produce therapeutic proteins. The performance of columns must be maintained as the process is scaled-up from the bench top to manufacturing plants and throughout column lifetimes. Difficulties in column evaluation procedures, potential changes to the integrity of packed beds, and logistics can arise as the column diameter, equipment, and buffer consumption increases to scale up the process.

A current method for chromatography column qualification calculates Height Equivalent to Theoretical Plates (HETP), a measure of dispersion following a pulse injection, by estimating the mean from the peak maximum and the standard deviation from the width of the peak at half height. The primary limitation of this method is that it does not provide an accurate measure of dispersion (i.e., HETP) when the peak shape deviates from a Gaussian distribution. In order to compensate for the lack of sensitivity, a second measurement, Asymmetry, is utilized to assess peak skewness. This measure compares the leading and tailing peak width at 10% of the maximum peak height. The limitations of this approach result in a lack of sensitivity to changes in column performance, and often results in the repacking or conditioning of a column, while column performance is actually acceptable. Other strategies for column qualification have been reported. These strategies include using Gaussian or non-Gaussian distributions to model in process transitions (see e.g., Larson, et al., "Use of Process Data to Assess Chromatographic Performance in Production-Scale Protein Purification Columns," *Biotechnol. Prog.* 19:485-492 (2003) and U.S. Pat. No. 9,047,438 to Belousov et al., and U.S. Pat. No. 8,410,928 to Ganguly). The Gaussian approaches have the same limitations in sensitivity as noted supra for the injection method and the reported non-Gaussian approaches require complex calculations.

An improved qualification procedure with greater sensitivity and more rationally defined limits is needed to monitor changes in chromatography column performance during repeated operation and evaluate the effectiveness for which the column will perform over its lifetime. The present invention is directed at overcoming this deficiency in the art.

SUMMARY OF THE INVENTION

The embodiments of the invention are defined, respectively, by the independent and dependent claims appended hereto, which for the sake of brevity are incorporated by reference herein. Other embodiments, features, and advantages of the various aspects of the invention are apparent from the detailed description below taken in conjunction with the appended drawing figures.

In certain embodiments, the present invention provides a method of operating a chromatography column in methods of manufacture for producing anti-TNF antibodies, the anti-TNF antibodies comprising a heavy chain (HC) comprising amino acid sequence of SEQ ID NO:1 and a light chain (LC) comprising amino acid sequence of SEQ ID NO:2 or an antigen binding fragment thereof, and specific pharmaceutical compositions of the antibodies. This method involves collecting column outlet signal and accumulated flow parameters at two or more intervals of at least one mobile phase transition front during a first operation of the chromatography column comprising column packing. This method further involves determining a model gamma cumulative distribution curve based on the collected column outlet signal and accumulated flow parameters for the at least one mobile phase transition front using Formula Ia for a rising transition front or Formula Ib for a falling transition front, $$C = 1 - \frac{1}{\Gamma(k)} \gamma\left(k, \frac{V - V_i}{\theta}\right) \quad \text{Formula Ia}$$

or $$C = \frac{1}{\Gamma(k)} \gamma\left(k, \frac{V - V_i}{\theta}\right) \quad \text{Formula Ib}$$

wherein C is column outlet signal for a given V, V is the accumulated flow divided by the column volume, and k, θ, and $V_i$ are the shape, scale and offset parameters used to define the curve. The height equivalent theoretical plate (HETP) value is calculated for the at least one mobile phase transition front using Formula II and the model gamma cumulative distribution curve parameters of k, θ, and $V_i$, $$HETP = \frac{\sigma^2}{\mu^2} L \quad \text{Formula II}$$

where
$\mu = k\theta + V_i$,
$\sigma = \sqrt{k\theta^2}$, and
L=column length

The quality of the chromatography column packing is assessed based on the calculated HETP value. Based on this assessment, the chromatography column is reused, conditioned, replaced, or repacked.

A new method for assessing column integrity, referred to herein as Gamma Distribution Transition Analysis (GDTA), has been developed. The new method uses a mathematical model to fit a curve through mobile phase transition front data that is generated during regular process steps of column operation. Model curve parameters are then utilized to calculate the dispersion across the column bed as a measure of column quality. Mobile phase transition fronts arise from discrete steps within the chromatography purification process where process buffers/wash solutions with different properties, such as conductivity, pH, and/or buffer components are used. The method can generally be applied to any one or more mobile phase transition fronts generated during normal column processing.

A primary advantage of the GDTA method is that it provides a more sensitive gauge of dispersion across the column bed than the Gaussian HETP estimation method. By using GDTA, it is no longer necessary to measure asymmetry, as the GDTA model correctly measures dispersion from the curve fit. Additionally, the use of the gamma distribution function facilitates ease of analysis of frontal transitions when compared to alternative non-gaussian methods previously reported. The use of mobile phase transitions already present in a chromatography process avoids the need for extra offline processing steps. Furthermore, in many cases, historical data allows for establishment of historical ranges of column efficiency prior to implementation. Finally, the GDTA method can be automated to ensure consistent application.

In certain embodiments, the present invention provides method of operating a chromatography column in methods of manufacture for producing anti-TNF antibodies, the anti-TNF antibodies comprising a heavy chain (HC) comprising amino acid sequence of SEQ ID NO:1 and a light chain (LC) comprising amino acid sequence of SEQ ID NO:2 or an antigen binding fragment thereof, said method comprising:

collecting column outlet signal and accumulated flow parameters at two or more intervals of at least one mobile phase transition front during a first operation of the chromatography column comprising column packing;

determining a model gamma cumulative distribution curve based on the collected column outlet signal and accumulated flow parameters for the at least one mobile phase transition front using Formula Ia for a rising transition front or Formula Ib for a falling transition front, $$C = 1 - \frac{1}{\Gamma(k)} \gamma\left(k, \frac{V - V_i}{\theta}\right) \quad \text{Formula Ia}$$

or $$C = \frac{1}{\Gamma(k)} \gamma\left(k, \frac{V - V_i}{\theta}\right) \quad \text{Formula Ib}$$

wherein C is column outlet signal for a given V, V is the accumulated flow divided by the column volume, and k, θ, and $V_i$ are the shape, scale and offset parameters used to define the curve;

calculating a height equivalent theoretical plate (HETP) value for the at least one mobile phase transition front using Formula II and the model gamma cumulative distribution curve parameters of k, θ, and $V_i$, $$HETP = \frac{\sigma^2}{\mu^2} L \quad \text{Formula II}$$

wherein
$\mu = k\theta + V_i$
$\sigma = \sqrt{k\theta^2}$
L=column length; and assessing quality of the chromatography column packing based on said calculated HETP value.

In certain embodiments, the present invention provides the method further comprising: conditioning, replacing, or repacking the chromatography column based on said assessing.

In certain embodiments, the present invention provides the method further comprising: collecting column outlet signal and accumulated flow parameters at two or more intervals of a corresponding mobile phase transition front during one or more subsequent uses of the chromatography column packing;

performing said determining and said calculating using the column outlet signal and accumulated flow parameters collected during each of the one or more subsequent uses of the chromatography column packing;

determining an HETP value of the chromatography column packing during each of said one or more subsequent uses based on said performing;

compiling a trend of the determined HETP values of the chromatography column packing of the two or more subsequent uses; and identifying a change in the quality of the chromatography column packing based on said compiled trend, wherein said conditioning, replacing or repacking the chromatography column is based on said identifying.

In certain embodiments, the present invention provides a method wherein an increase in the HETP value of the chromatography column packing in the one or more subsequent uses of said column packing as compared to the HETP value of the chromatography column packing in one or more earlier uses of said column packing identifies a decrease in quality of the chromatography column packing.

In certain embodiments, the present invention provides a method wherein column outlet signal and accumulated flow parameters of two or more different mobile phase transition fronts during said first operation of the column packing are collected, said method comprising:

performing said determining and calculating using the column outlet signal and accumulated flow parameters collected for each of the two or more different mobile phase transition fronts independently to calculate an HETP value for each of the two of more different mobile phase transition fronts;

assessing the quality of the chromatography column packing based on the two or more calculated HETP values, whereby said conditioning, replacing or repacking the chromatography column is based on said assessing.

In certain embodiments, the present invention provides a method wherein the chromatography column is selected from the group consisting of: a Protein A affinity chromatography column, a cation exchange chromatography column, and an anion exchange chromatography column.

In certain embodiments, the present invention provides a method wherein the Protein A affinity chromatography column comprises a MabSelect™ Protein A affinity chromatography column, the cation exchange chromatography column comprises a UNOsphere S™ cation exchange chromatography column, and the anion exchange chromatography column comprises a Q Sepharose™ XL anion exchange chromatography column.

In certain embodiments, the present invention provides a method wherein the mobile phase transition front in the Protein A affinity chromatography column is generated from one or more fronts selected from the group consisting of: a front generated during elution of the anti-TNF antibodies, a front generated during sanitization of the column with Guanidine HCl, a front generated during post-sanitization rinsing of the column with 0.1 M Sodium Citrate, pH 3.5.

In certain embodiments, the present invention provides a method wherein the mobile phase transition front in the cation exchange chromatography column is generated from one or more fronts selected from the group consisting of: a front generated during loading of solvent/detergent (S/D) treated material comprising the anti-TNF antibodies, a front generated during elution of the anti-TNF antibodies, and a front generated during a column strip.

In certain embodiments, the present invention provides a method wherein the mobile phase transition front in the cation exchange chromatography column is generated from one or more fronts selected from the group consisting of: a front generated during cleaning of the column with Sodium Hydroxide and a front generated during a column strip.

BRIEF DESCRIPTION OF THE DRAWINGS

FIG. 1A is a graph showing an exemplary gamma distribution transition analysis curve fit to mobile phase transition data. FIG. 1B is a graph showing an exemplary gamma distribution transition analysis curve fit to mobile phase transition data with parameters from that curve used to calculate the height equivalent theoretical plate (HETP) as a measure of column efficiency.

DETAILED DESCRIPTION OF THE INVENTION

Figure 1A:
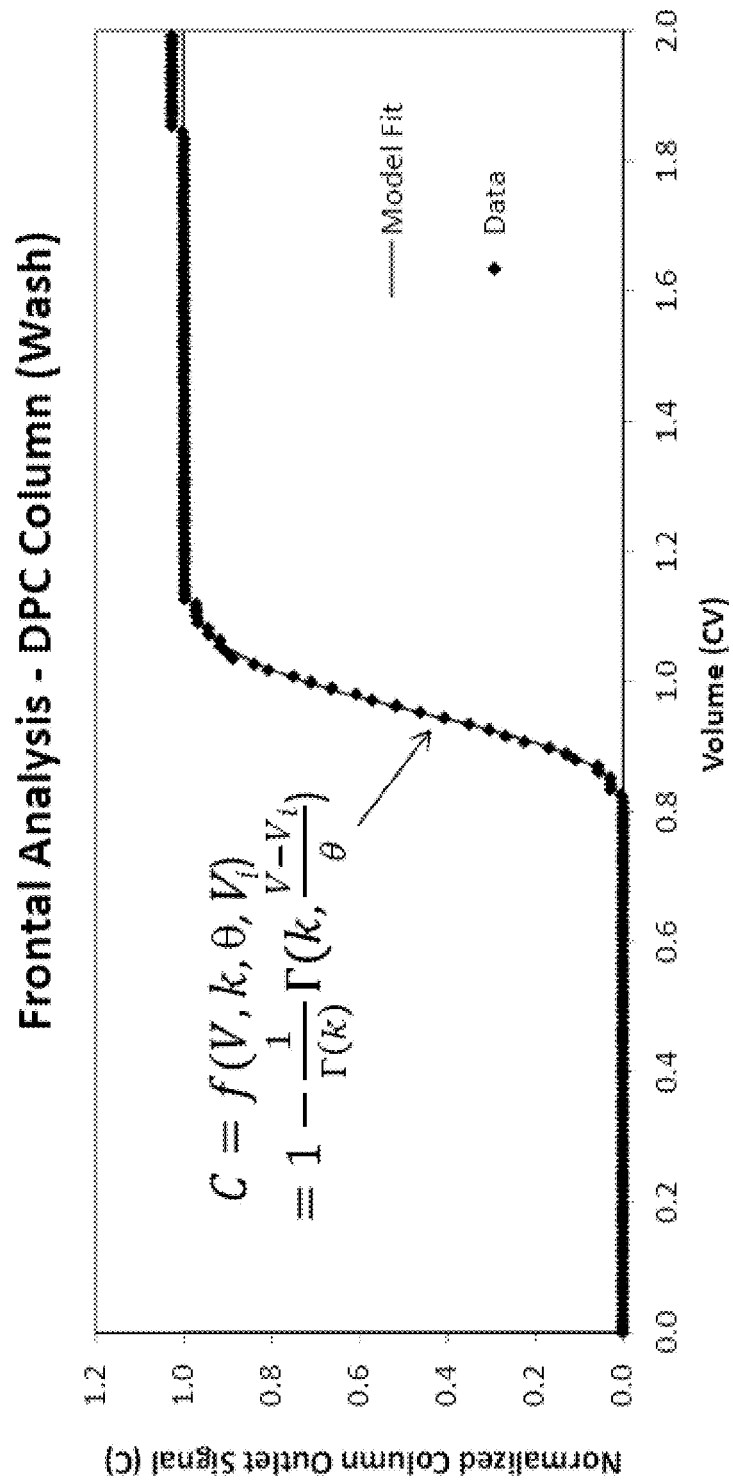
FIGS. 1A-1B show graphs of exemplary gamma distribution transition analysis curve fits.

The present disclosure relates to an improved qualification procedure for monitoring changes in packed chromatography column beds during repeated operation of the column in methods of manufacture for producing anti-TNF antibodies, e.g., the anti-TNFα antibody SIMPONI® (golimumab), and specific pharmaceutical compositions of the antibody. This method, independent of scale, provides a practical means to evaluate the effectiveness for which the column will perform throughout the column lifetime.

Chromatography column separation efficiency is often characterized using the theoretical plate model of chromatography. Using this approach, the chromatography column is perceived as consisting of a number of stages or theoretical plates. Each plate is the distance over which the sample components achieve equilibrium between the mobile and stationary phases (see Van Deemter, Zuiderweg and Klinkenberg, "Longitudinal Diffusion and Resistance to Mass Transfer as Causes of Nonideality in Chromatography," *Chem. Engng. Sci.* 5: 271-289 (1956), which is hereby incorporated by reference in its entirety). Column efficiency is measured by the number of theoretical plates in the column $N_p$, where more plates in the column means more equilibrations, less dispersion of chromatographic bands, narrower peaks, and better-quality separation. The higher the number of plates in a given column, the lower the plate height. Accordingly, column efficiency can also be measured by calculating plate height, which is referred to as "height equivalent to a theoretical plate" or HETP. Using this approach, the smaller the HETP value the higher the efficiency of column separation.

HETP is calculated by dividing by the length of chromatography column L by the number of theoretic plates $N_p$.

$$HETP = L/N_p$$

The number of theoretical plates that a column possesses has historically been determined by examining a chromatographic peak after a pulse injection using the following formula:

$$N_p = 5.54 \left( \frac{t_R}{w_{1/2}} \right)^2$$

where $t_R$ is the retention time and $w_{1/2}$ is the peak width at half height. However, this approach does not provide an accurate measure of column efficiency when the peak shape used to calculate $N_p$ deviates from a Gaussian distribution. In order to compensate for this lack of sensitivity, a second measurement—Asymmetry—is used to assess peak skewness. This measure compares the leading and tailing peak width at 10% of the maximum peak height. As discussed supra, this model lacks sensitivity to detect changes in column performance.

The method described herein provides an alternative and more accurate measure of HETP that is based on gamma distribution over one or more mobile phase transition fronts that occur during routine chromatography column operation. Thus, the present disclosure is directed to a method of operating a chromatography column. This method involves collecting column outlet signal and accumulated flow parameters at two or more intervals of at least one mobile phase transition front during a first operation of the chromatography column containing column packing. This method further involves determining a model gamma cumulative distribution curve based on the collected column outlet signal and accumulated flow parameters for the at least one mobile phase transition front using Formula Ia for a rising transition front or Formula Ib for a falling transition front.

$$C = 1 - \frac{1}{\Gamma(k)} \gamma\left(k, \frac{V - V_i}{\theta}\right) \qquad \text{Formula Ia}$$

or $$C = \frac{1}{\Gamma(k)} \gamma\left(k, \frac{V - V_i}{\theta}\right) \qquad \text{Formula Ib}$$

In reference to Formula Ia and Formula Ib, C is column outlet signal for a given V, V is the accumulated flow divided by the column volume, and k, θ, and $V_i$ are the shape, scale and offset parameters used to define the curve. The height equivalent theoretical plate (HETP) value is calculated for the at least one mobile phase transition front using Formula II and the model gamma cumulative distribution curve parameters of k, θ, and $V_i$, $$HETP = \frac{\sigma^2}{\mu^2} L \qquad \text{Formula II}$$

where
μ=kθ+$V_i$,
σ=$\sqrt{k\theta^2}$, and
L=column length.

The quality of the chromatography column packing is assessed based on the calculated HETP value. Based on the assessment of column quality, the chromatography column is determined to be acceptable for subsequent use, or otherwise must be conditioned, replaced, or repacked.

The method of column qualification disclosed herein can be applied to any chromatography column. Exemplary chromatography columns include, without limitation, those used for liquid chromatography, high-performance liquid chromatography (HPLC), ion exchange chromatography, affinity chromatography, molecular exclusion, super critical fluid chromatography, gas chromatography, size exclusion chromatography, reverse phased chromatography, two-dimensional chromatography, fast protein (FPLC) chromatography, countercurrent chromatography, chiral chromatography, aqueous normal phase (ANP), mixed mode chromatography, and pseudo-affinity chromatography. Exemplary column packing material includes, without limitation, affinity chromatography packing material (e.g., protein A or protein G affinity chromatography packing material), ion exchange chromatography packing material (e.g., cation exchange (carboxymethyl resins), anion exchange (amino ethyl resins), and mixed-mode exchange chromatography packing material), adsorption chromatography packing material (e.g. silica gel or alumina packing material), hydrophobic interaction chromatography packing material (e.g. phenyl-sepharose, aza-arenophilic resins, or m-aminophenylboronic acid packing materials), metal chelate affinity chromatography packing material (e.g., Ni(II)- and Cu(II)-affinity material), size exclusion chromatography packing material (e.g., gel electrophoresis or capillary electrophoresis packing material), or molecular exclusion chromatography packing material (e.g., polystyrene).

The method described herein can be applied during routine chromatography column operation, e.g., during isolation, purification, or identification of chemical or biological entities in a sample. Such compounds may include, for example but without limitation, proteins (e.g., antibodies and fragments thereof), nucleic acids, carbohydrates, lipids, organic small molecules, inorganic small molecules, viruses, liposomes, and hybrids or variant forms of any such compounds.

In contrast to previous chromatography column qualification methods, which require the column be taken offline for testing, e.g., the pulse injection method, the method as described herein is carried out during routine column operation. The present method takes advantage of mobile phase process transitions involving process buffers and solutions having different properties, which occur during a routine column purification process.

In accordance with the method of the present invention, the "mobile phase" is the liquid phase in column chromatography that surrounds and moves through the stationary chromatography material of the chromatography column packing. During chromatography column operation, the composition and properties of the mobile phase often change with each process step, e.g., equilibration, washes, etc. Changes in the properties of the mobile phase can be detected and measured in the eluate, i.e., the mobile phase that is eluted from the column after passing through the stationary phase. As used herein, the "column outlet signal" is the signal of a physical or chemical property of the eluate from the mobile phase that is detected as the eluate elutes off the column. The physical or chemical property providing the column outlet signal can be any property, such as pH, conductivity, light absorption, fluorescence, charge, salt concentration, polarimetry, refractive index, electrochemical response, mass-to-charge ratio, etc. that can be measured using any typical chromatography detector. Chromatography detectors suitable for measuring the column outlet signal include, without limitation, a mass spectrometer, infrared spectrometer, visible spectrometer, ultraviolet spectrometer, Fourier transform infrared spectrometer, flame ionization detector, low angle laser light scattering detector, diode array detector, fluorescence spectrometer, pH detector, conductivity detector, electrochemical detector, and refractive index detector.

The column outlet signal is collected from the eluate. In addition, to collecting the column outlet signal, the "accumulated flow" is also collected. The "accumulated flow" is the total volume of fluid eluted from the column over time. This value is divided by the volume of the column to be expressed in units of column volumes.

A transition front is generated by the change in column outlet signal over the accumulated flow. A transition front arises from the sequential application of different mobile phases having one or more different properties (e.g., conductivity, pH, etc.) to a column. In accordance with the method described herein, the column outlet signal over the transition front can be normalized to have a maximum value of 1 and a minimum value of 0. As referred to herein, a "falling transition front" is a mobile phase transition where the starting mobile phase has a column outlet signal, e.g., conductivity, that is higher than the column outlet signal of the sequentially introduced mobile phase.

A "rising transition front" as used here is a mobile phase transition where the starting mobile phase has a column outlet signal, e.g., conductivity, that is lower than the column outlet signal of the sequentially introduced mobile phase.

A transition front is created by adding a first mobile phase to the chromatography column containing column packing to be qualified during the course of column operation. At some time after the addition of the first mobile phase, e.g., as the first mobile phase begins to elute, a second mobile phase having a different detectable column outlet signal compared to the first mobile phase is added to the chromatography column containing the column packing. The transition front is detected by collecting column outlet signal and accumulated flow parameters at two or more intervals of the mobile phase as it transitions between the first and second mobile phases.

In one embodiment, the column outlet signal for the first and second mobile phases differ in signal by an amount exceeding the signal noise. In one embodiment, the difference in column outlet signal between the first and second mobile phases is 5% above the background signal noise. In another embodiment, the difference in column outlet signal between the first and second mobile phases is at least 10% above the background signal noise. In another embodiment, the difference in column outlet signal between the first and second mobile phases is at least 15% above the background signal noise.

In one embodiment, the column outlet signal detected over the transition front is conductivity. In this embodiment, the column outlet signal between the first and second mobile phases preferably differs by at least 1 $\mu$S/cm, by at least 10 $\mu$S/cm, by at least 100 $\mu$S/cm, by at least 1 mS/cm, or by greater than 1 mS/cm.

In another embodiment, the column outlet signal detected over the transition front is pH. In this embodiment, the column outlet signal between the first and second mobile phases preferably differs by at least 0.05 pH units, by at least 0.1 pH units, by at least 1 pH units, by at least 2 pH units, or by greater than 2 pH units.

In another embodiment, the column outlet signal detected over the transition front is UV-Vis absorbance. In this embodiment, the column outlet signal between the first and second mobile phases preferably differs by at least 0.01 absorbance unit, by at least 0.1 absorbance unit, by at least 0.5 absorbance unit, by at least 0.8 absorbance unit, or by more than 0.8 absorbance unit.

In another embodiment, the column outlet signal detected over the transition front is infrared absorbance. In this embodiment, the column outlet signal between the first and second mobile phases preferably differs by at least 1 percent transmittance, by at least 10 percent transmittance, by at least 20 percent transmittance, by at least 30 percent transmittance, or by more than 30 percent transmittance.

In one embodiment, the mobile phase transition front is generated by a change from a mobile phase containing a denaturing agent to a mobile phase containing a non-denaturing agent. In another embodiment, the mobile phase transition front is generated by a change from a mobile phase containing a non-denaturing agent to a mobile phase containing a denaturing agent.

In another embodiment, the mobile phase transition front is generated by a change from an alkaline mobile phase condition to a neutral or more acidic mobile phase condition. Alternatively, the mobile phase transition front is generated by a change from an acidic mobile phase condition to a neutral or more alkaline mobile phase condition.

In another embodiment, the mobile phase transition front is generated by a change from organic solvent containing mobile phase to an aqueous mobile phase. Alternatively, the mobile phase transition front is generated by a change from an aqueous mobile phase to an organic solvent containing mobile phase.

The column outlet signal and accumulated flow parameters are collected at various intervals over the course of the mobile transition front. Preferably, column outlet signal and accumulated flow parameters are collected over the course of the entire mobile transition front, from the minimum column outlet signal to the maximum column outlet signal or vice versa. In one embodiment, the column outlet signal and accumulated flow parameters are collected at irregular intervals, e.g., collected when a change in the column outlet signal is detected. In another embodiment, the column outlet signal and accumulated flow parameters are collected at regular timed intervals over the course of the entire mobile transition front. For example, in one embodiment, the column outlet signal and accumulated flow parameters are collected at 1 second intervals over the course of the entire mobile transition front. In another embodiment, the column outlet signal and accumulated flow parameters are collected at 5, 10, 15, 20, 25, 30, 35, 40, 45, 50, 55, or 60 second intervals over the course of the mobile transition phase.

In one embodiment, the column outlet signal data is normalized as described supra by setting the maximum value to 1 and the minimum value to 0 over the period of analysis. Flow is also converted to column volumes to standardize for comparison of data between different column packings. Using this data, the gamma cumulative distribution function ("CDF") is used to generate a curve that best fits the collected data points. The gamma CDF is determined by three values: shape parameter k; scale parameter $\theta$ (theta); and offset parameter $V_i$ using the following Formula I:

$$C = f(V, k, \theta, V_i) \qquad \text{Formula I}$$

In reference to Formula I, C is column outlet signal for a given V, V is the accumulated flow divided by the column volume. Formula Ia, which is derived from Formula I, is used determine the gamma distribution function value along a rising transition front.

$$C = 1 - \frac{1}{\Gamma(k)} \gamma\left(k, \frac{V - V_i}{\theta}\right) \quad \text{Formula Ia}$$

wherein
Γ is the upper incomplete gamma function, and
γ is the lower incomplete gamma function.

Alternatively, Formula Ib, which is also derived from Formula I, is used to determine the gamma distribution function value along a falling transition front.

$$C = \frac{1}{\Gamma(k)} \gamma\left(k, \frac{V - V_i}{\theta}\right) \quad \text{Formula Ib}$$

FIG. 1A is a graph plotting exemplary normalized column outlet signal and column volume data collected over a column transition front. Formula Ia was used to generate the curve fit to the data.

The best fit gamma CDF parameters are determined by manipulating the values of k, θ, and $V_i$ to find the parameters that produce a model curve with the least sum of squares deviation from the data. This curve is fitted through the data points from the entire transition front to generate the best fit model. The k, θ, and $V_i$ parameters from this curve are utilized to calculate the number of plates $N_p$ in the column or the plate height, i.e., HETP, as indicators of column efficiency.

The number of plates $N_p$ is calculated based on the mean μ and variance $\sigma^2$ of the model curve. The mean and variance are derived from the curve as follows:

Mean, $\mu = k\theta + V_i$

Variance, $\sigma^2 = k\theta^2$

The number of plates is calculated based on the mean and variance as follows:

Number of plates, $N_p = \mu^2/\sigma^2$

The HETP is calculated as described supra based on the length of the column L in centimeters divided by the number of plate $N_p$, as follows.

$$HETP = \frac{L}{N_p} = \frac{\sigma^2}{\mu^2} \cdot L = \frac{k\theta^2 L}{(k\theta + V_i)}$$

Figure 1B:
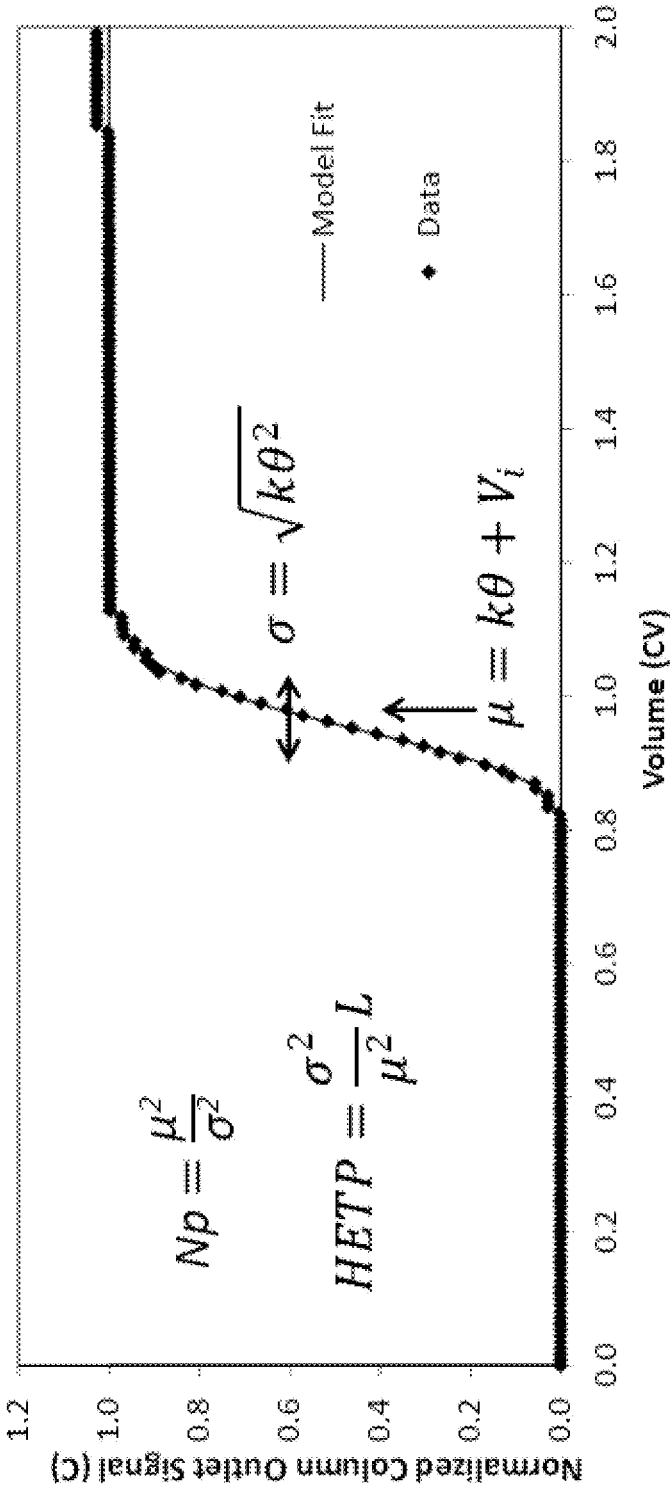

FIG. 1B shows the same graph as shown in FIG. 1A, with the mean μ and variance σ2 parameters defined.

To evaluate the model fit to the data calculated as described herein, the mean ($V_m$), sum of squares (SS), and mode can also be determined. SS is a direct measure of the deviation of the model curve from the process data upon which it is derived. The $V_m$ value is a measure of the center point of the transition in units of column volumes. This value should be close to one as it typically takes one column volume for a buffer transition. Mean is not typically affected by the shape of the front. Mean values are used to check the automatic calculations for errors. For example, a low value might indicate a data collection error and may require further investigation to confirm the result. The mode corresponds to the volume where the rate of change is greatest. This will be equal to the mean when the transition curve is symmetrical. Typically, the transitions are skewed, and the mode is lower than the mean.

In addition to HETP, other factors that can be calculated from the k (shape) parameter include skewness ($\gamma_1$), which is a measure related to asymmetry, and kurtosis ($\gamma_2$), which is a measure of the peak sharpness. These factors can be used to identify changes in column performance.

$$\gamma_1 = \frac{2}{\sqrt{k}}$$

$$\gamma_2 = \frac{6}{k}$$

In accordance with the method described herein, the column outlet signal and accumulated flow parameters are collected for the same mobile transition phase each time the column process is run on the column to calculate HETP from the gamma CDF. Historical data generated by columns used for the same process step and same scale can also be retrieved and utilized to calculate HETP. The HETP data is compiled to identify trends in the HETP values of corresponding transitions during historical or current operations to identify upper and lower control limits of the HETP value. The control limits are the high and low values of HETP that define the range of acceptable HETP values, i.e., HETP values that correspond to acceptable column efficiency. These upper and lower control limits can be set based on statistical evaluation. For example, in one embodiment the upper and lower control limits are set by calculating the mean+/−2, 3, or 4 standard deviations. In one embodiment, the upper and lower control limits are set by calculating the mean+/−3 standard deviations as described in the Examples herein. In another embodiment, the upper and lower control limits can be set by calculating the confidence interval from the historical data. In one embodiment, the upper and lower control limits are set by calculating the 95%, 96%, 97%, or 98% confidence interval from the historical data. In another embodiment, the upper and lower control limits are set by calculating the 99% confidence interval from the historical data.

The upper and lower control limits are utilized to identify changes in column efficiency over time and use of the column. Typically, any increase in HETP that exceeds the upper control limit may be indicative of a decrease in column efficiency. If during routine column monitoring, an adverse trend in HETP is observed or the control limits are exceeded, the eluate product quality, column process performance, and/or impurity removal data should be evaluated to ensure product quality for the identified batch. Should any of the product quality or column performance fail the criteria set, appropriate corrective action, such as conditioning, repacking or replacing the column, and qualification should be performed prior to release for further use. Methods of conditioning a chromatography column to redistribute the packed bed will vary depending on the column being employed, but are well understood to those of skill in the art.

The monitoring of column performance during column operation can be based on one, or more than one, transition phases that are routinely included in a purification protocol. Preferably, monitoring is based on HETP values calculated based on gamma CDF for two, or three, or more transition phases during a purification protocol.

As noted infra, calculating HETP using the GDTA method as described herein to determine column performance can be based on historical data collected from columns used for the same process step and same scale. Data generated from a qualified reduced scale model of the process step can also be used for the evaluation. This allows for the evaluation of the quality of the column's performance as compared to the qualification data.

Factors such as flow rate (Van Deemter effect), potential buffer interactions and extra column volume can impact the results of the GDTA method as described herein and should be assessed in setting the control limits for GDTA. Transition fronts included in the GDTA preferably meet certain criteria such as both mobile phase column outlet signal measurements are on scale, the column outlet signal measurement difference between mobile phases is above the background signal noise, and interaction between mobile phase and resin is consistent and reproducible.

Common column evaluation criteria used for release and monitoring during use shall be determined by evaluating historical data specific to equipment and resin type. Examples of routine product quality and process performance measurements that can be used to evaluate the relationship between column qualification results and performance are listed in Table 1. Routine quality and process performance measurements used for evaluation are not limited to those listed in Table 1, but the list is meant to be a guideline and should be based on the specific requirements of the project and process step being evaluated. Specifications and acceptance criteria for product quality and process performance are project specific and will be determined based on process requirements.

TABLE 1

Routine Quality and Step Performance Measures

| Parameter | Analytical Method |
| --- | --- |
| Pre-Elution Volume (CV) | |
| Elution Volume (CV) | |
| Step Yield | |
| Chromatographic Profile | Visual inspection |
| Eluate Concentration | A280 |
| Eluate Monomer | DW-SE-HPLC |
| Process Impurities | Various Assays |

The gamma distribution transition analysis method as described herein can be carried out in real-time during column operation. This method involves collecting, by a chromatography column qualification computing device, column outlet signal and accumulated flow parameters at two or more intervals of at least one mobile phase transition front during a first operation of the chromatography column comprising column packing; determining, by a chromatography column qualification computing device, a model gamma cumulative distribution curve based on the collected column outlet signal and accumulated flow parameters for the at least one mobile phase transition front using Formula Ia for a rising transition front or Formula Ib for a falling transition front.

$$C = 1 - \frac{1}{\Gamma(k)} \gamma\left(k, \frac{V - V_i}{\theta}\right) \quad \text{Formula Ia}$$

or $$C = \frac{1}{\Gamma(k)} \gamma\left(k, \frac{V - V_i}{\theta}\right). \quad \text{Formula Ib}$$

In reference to Formulas Ia and Ib, C is column outlet signal for a given V, V is the accumulated flow divided by the column volume, and k, θ, and $V_i$ are the shape, scale and offset parameters used to define the curve. This method further involves calculating, by a chromatography column qualification computing device, a height equivalent theoretical plate (HETP) value for the at least one mobile phase transition front using Formula II and the model gamma cumulative distribution curve parameters of k, θ, and $V_i$, $$HETP = \frac{\sigma^2}{\mu^2} L \quad \text{Formula II}$$

wherein
$\mu = k\theta + V_i$
$\sigma = \sqrt{k\theta^2}$
L = column length.

The method further involves assessing, using a chromatography column qualification computing device, quality of the chromatography column packing based on said calculated HETP value. Based on this assessment, the chromatography column operator can determine whether the chromatography column can be reused, or needs to be replaced, repacked, or conditioned prior to the next column operation.

Figure 2:
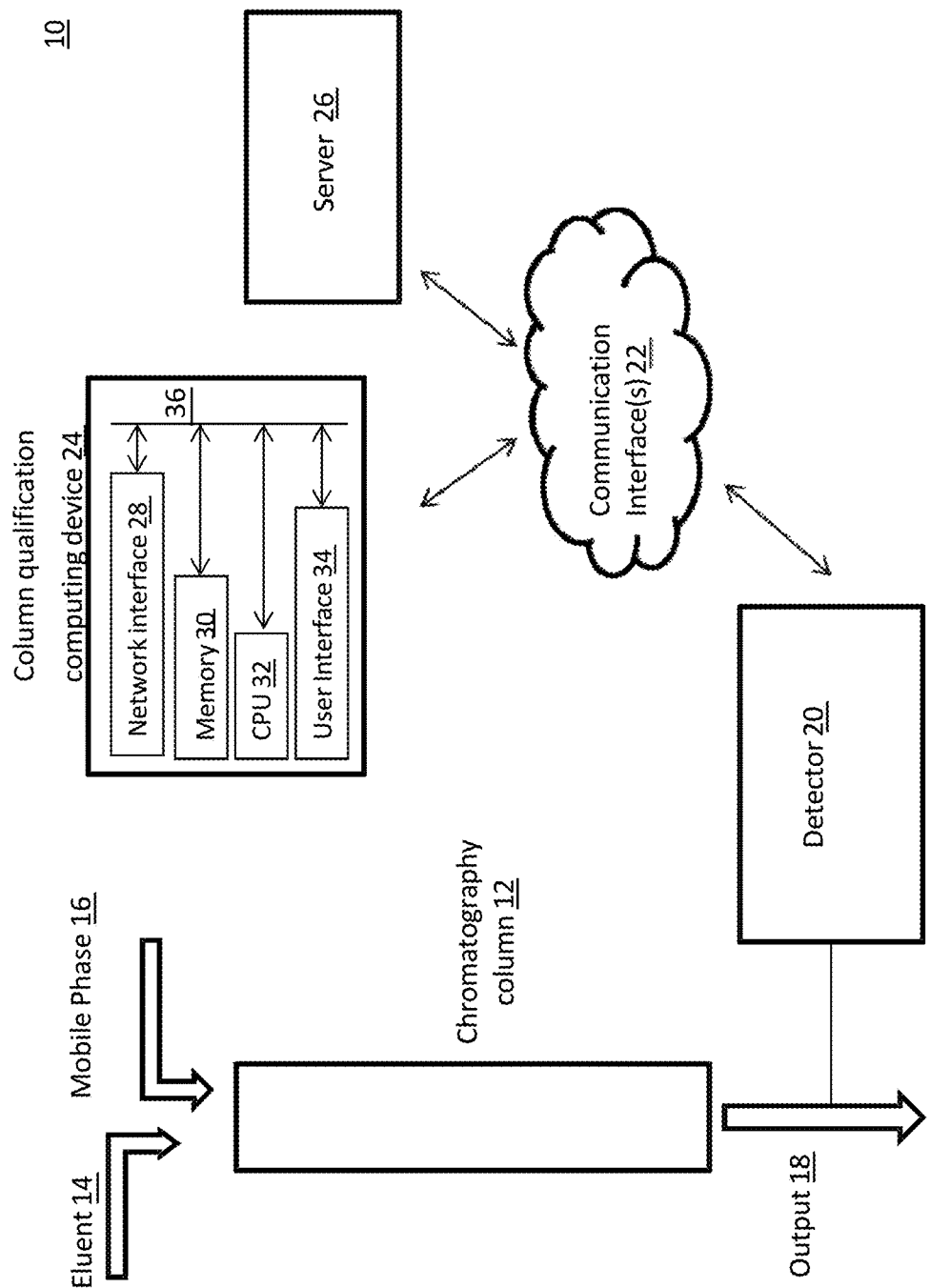
FIG. 2 is a diagram showing the chromatography column qualification system described herein.
Figure 3:
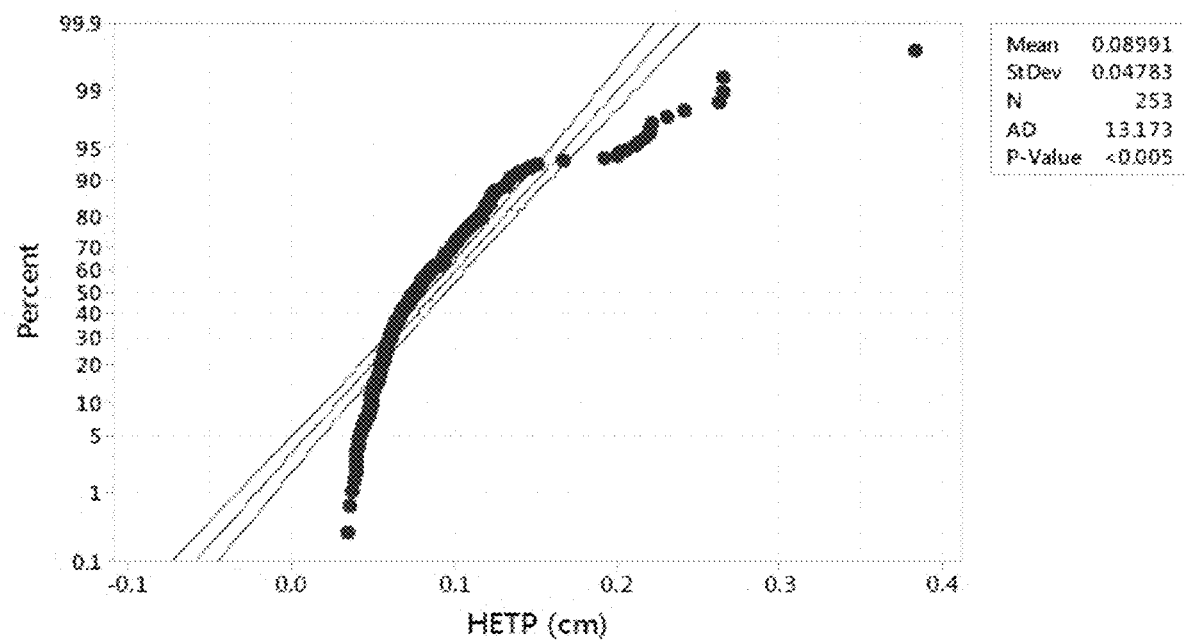
FIG. 3 is a probability plot of HETP for Protein A column equilibration front without transformation.
Figure 4:
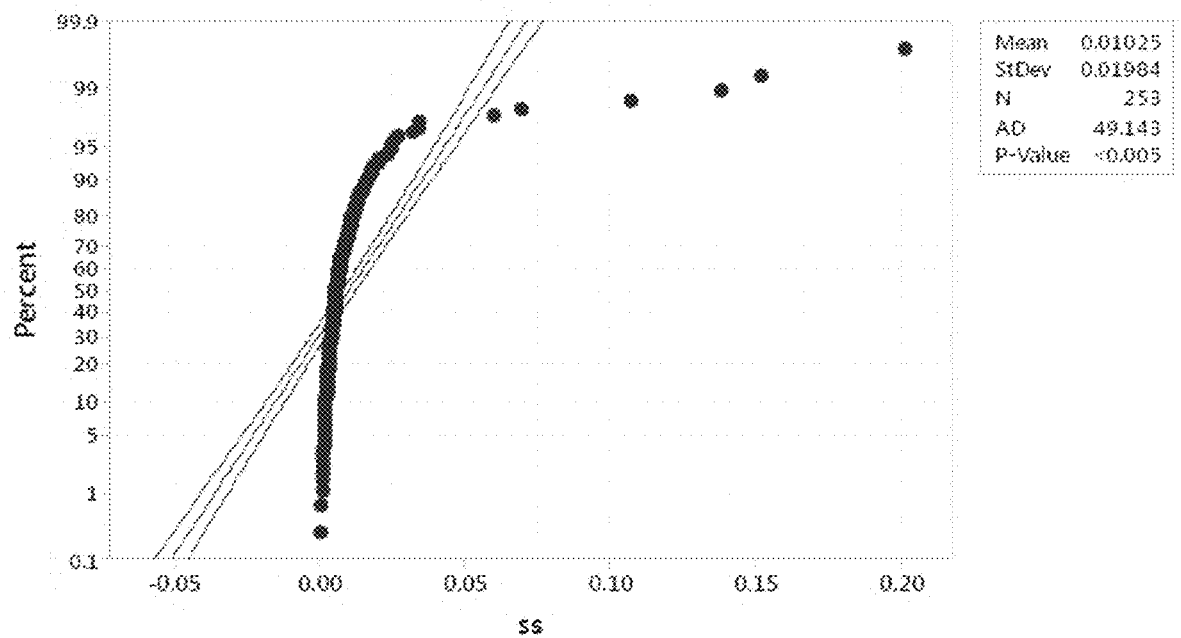
FIG. 4 is a probability plot of the sum of squares (SS) for Protein A column equilibration front without transformation.
Figure 5:
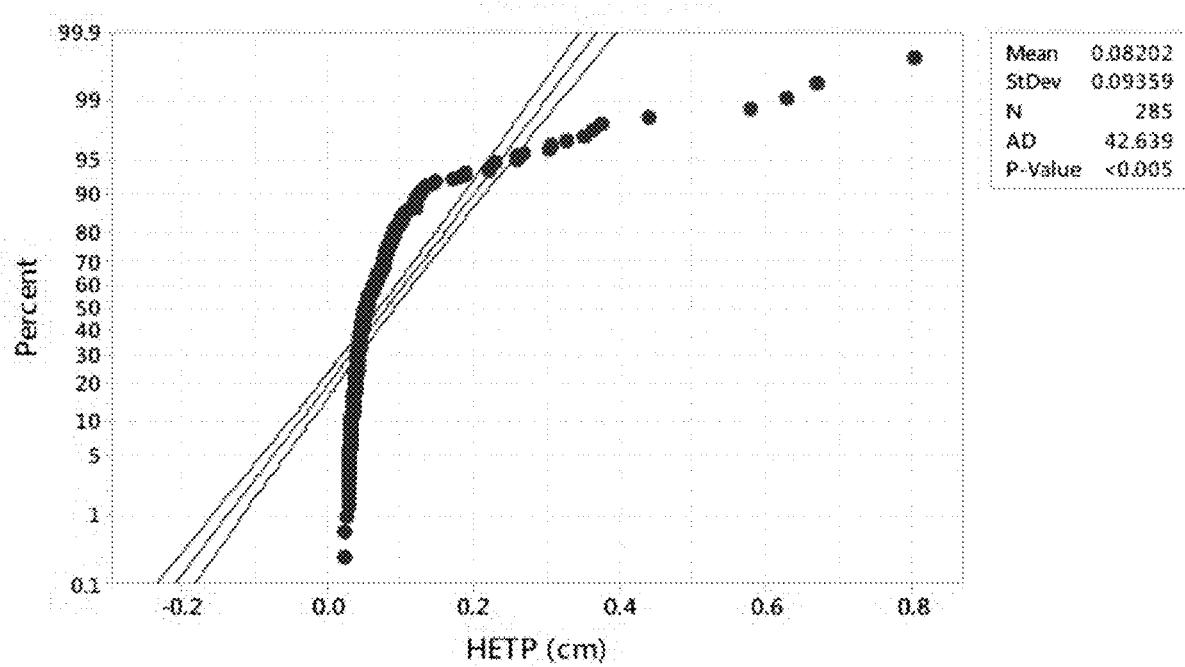
FIG. 5 is a probability plot of HETP for Protein A column wash front without transformation.
Figure 6:
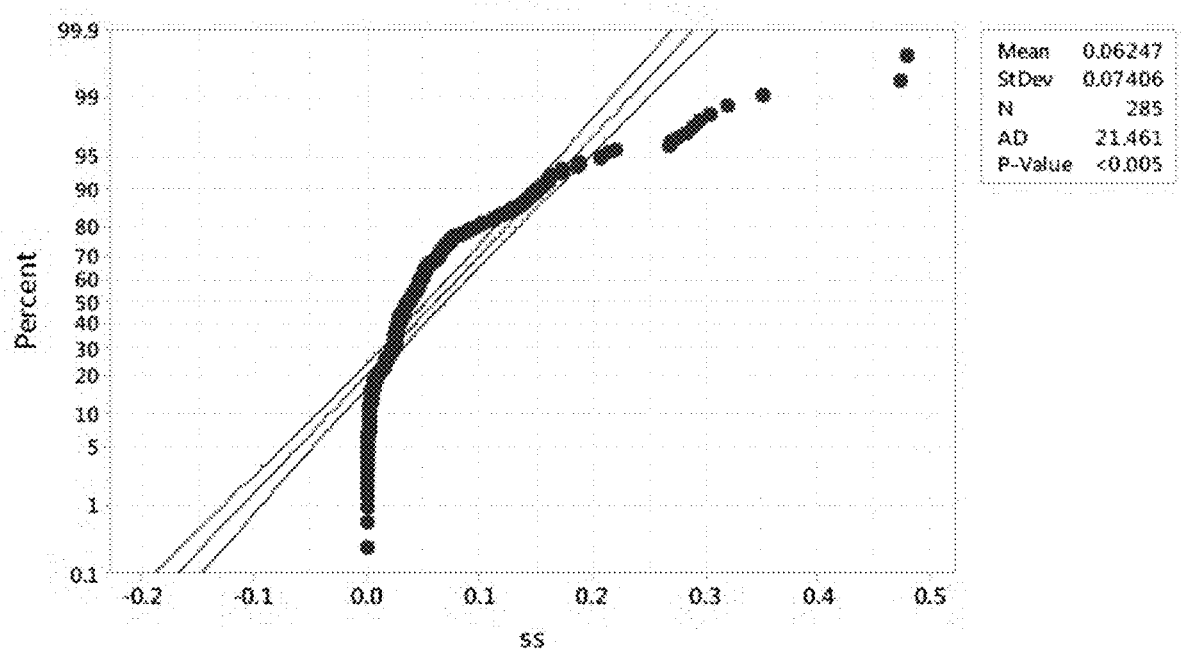
FIG. 6 is a probability plot of SS for Protein A column wash front without transformation.
Figure 7:
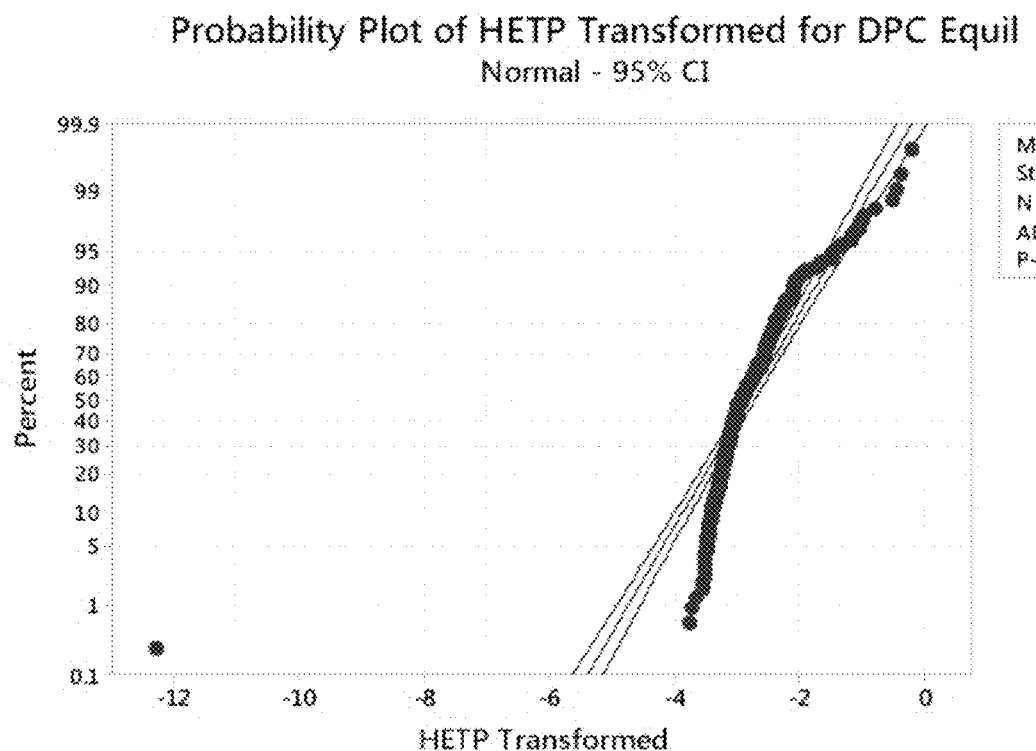
FIG. 7 is a probability plot of HETP for Protein A column equilibration front with natural log ($\lambda$=0) transformation.
Figure 8:
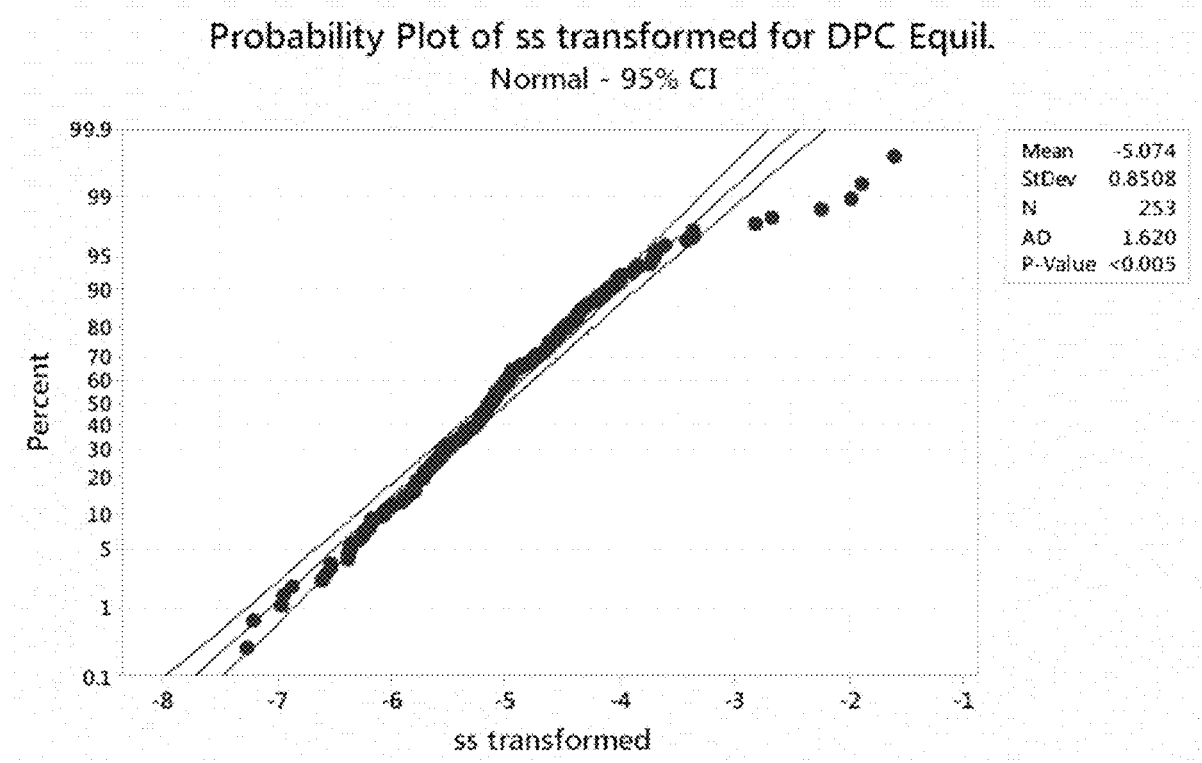
FIG. 8 is a probability plot of SS for Protein A column equilibration front with natural log ($\lambda$=0) transformation.
Figure 9:
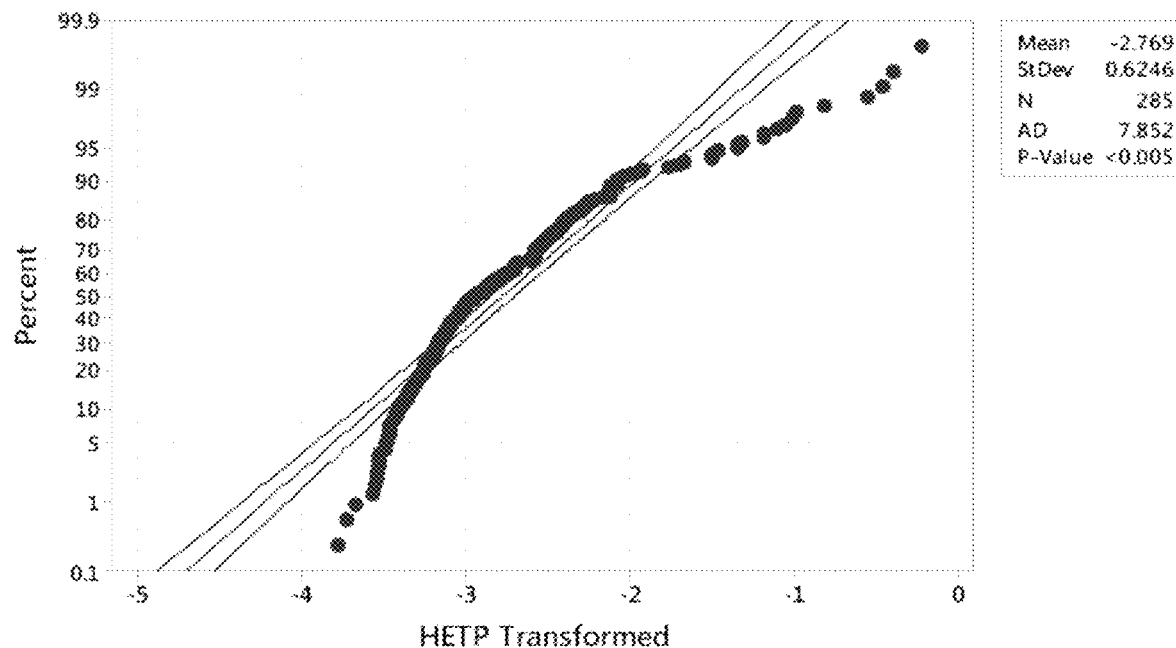
FIG. 9 is a probability plot of HETP for Protein A column wash front with natural log ($\lambda$=0) transformation.
Figure 10:
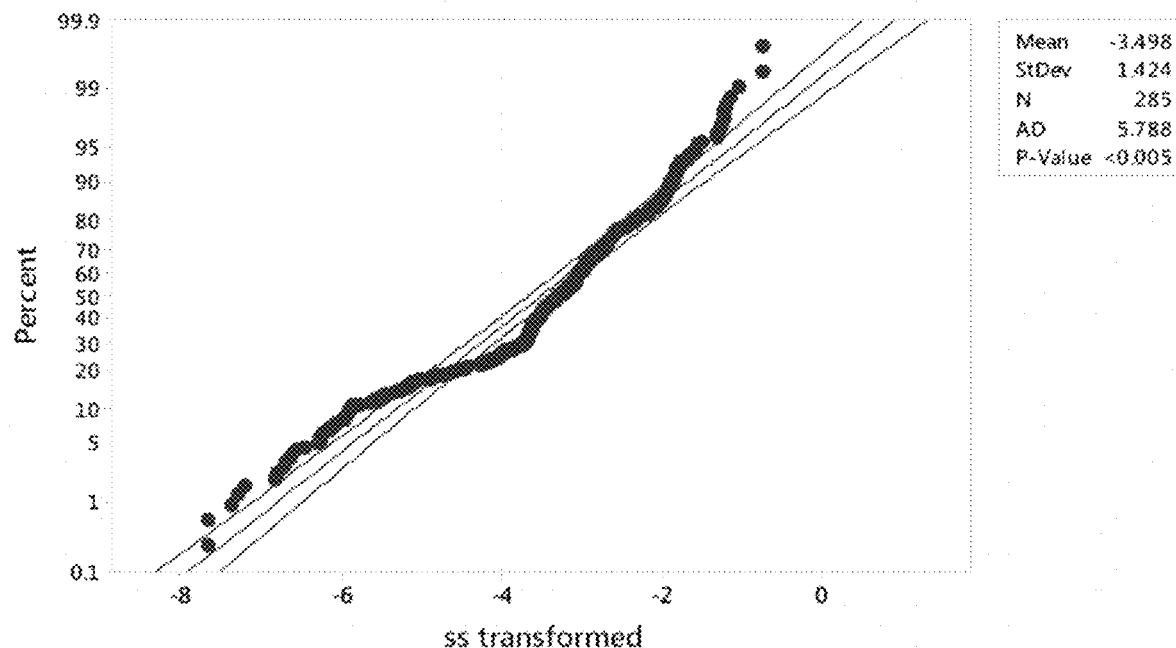
FIG. 10 is a probability plot of SS for Protein A column wash front with natural log ($\lambda$=0) transformation.

FIG. 2 is a diagram providing an overview of the method and system of operating a chromatography column and assessing column efficiency in real-time as described herein. As shown in FIG. 2 and described supra, the system 10 includes a chromatography column 12 used to separate biomolecules introduced into the column as a complex mixture, i.e., eluent 14, a detector 20 that detects a column output signal in the eluate as it elutes from the chromatography column, a communications interface 22 that transmits signal/data from the detector 20, a column qualification computing device 24, and a server 26.

Chromatography column 12 is filled with a permeable, semi-permeable, or impermeable solid phase column packing material. Suitable chromatography columns and column packing material are described supra. The eluent 14 containing the biomolecules of interest is introduced into the chromatography column 12. A mobile phase 16 is also introduced to the chromatography column 12. The mobile phase 16 facilitates separation of the biomolecules through the stationary phase of the chromatography column 12 and elution of the biomolecules in the eluate through the output 18 of the chromatography column. In accordance with the method as described herein, the mobile phase 16 comprises the sequentially introduced column buffers and/or wash reagents that differ in one or more physical or chemical properties from each other as described infra, e.g., pH, conductivity, salt concentration. These differences in one or more physical or chemical properties are detected in the eluate by the detector 20.

Detector 20 is coupled to the output 18 of chromatography column 12. Accordingly, detector 20 monitors and collects the column output signal via the eluate of chromatography column 12. Suitable detectors and the properties of the eluate, i.e., the column output signal, detected are described supra. The detector is coupled to a communications interface unit 22 that transmits data collected by the detector 20 (e.g., column output signal and accumulated flow parameters) to a column qualification computing device 24 for data processing and/or a server 26 for storage.

The column qualification computing device 24 of the system described herein can be any computing device, e.g., a computer, a personal computing device, smartphone, etc. that includes a central processing unit (CPU) or processor 32, a memory 30, a network interface 28, and a user interface 34 which are coupled together by a bus 36 or other link. The column qualification computing device 24 may include other types and/or numbers of components and elements in other configurations.

The processor 32 in the column qualification computing device 24 executes a program of stored instructions for one or more aspects of gamma distribution transition analysis described and illustrated by way of the examples herein, although other types and/or numbers of processing devices could be used and the processor 32 can execute other types and/or numbers of programmed instructions. In one embodiment, the processor 32 is located solely on the column qualification computing device 24. In another embodiment, the processor is distributed between the detector 20 and the column qualification computing device 24. For example, in one embodiment, the processor 32 of the column qualification computing device 24 comprises a microcontroller that is coupled to the detector. In this embodiment, the microcontroller serves as an on-board processor that is capable of mapping or converting data collected by the detector 20 into a digital signal that is transmitted to the column qualification computing device 24. The microcontroller coupled to the one or more detectors is capable of carrying out one or more processing functions of the column qualification computing device 24.

The memory 30 in the column qualification computing device 24 stores these programmed instructions for one or more aspects of the GDTA as described herein. A variety of different types of memory storage devices, such as a random access memory (RAM) and/or read only memory (ROM) in the timing processor device or a floppy disk, hard disk, CD ROM, DVD ROM, or other computer readable medium which is read from and written to by a magnetic, optical, or other reading and writing system that is coupled to the processor 32 in the column qualification computing device 24, can be used for the memory 30.

The network interface 28 of the column qualification computing device 24 operatively couples and facilitates communication between the column qualification computing device 24 and the detector 20, although other types and/or numbers of communication networks or systems with other types and/or numbers of connections and configurations can be used.

The column qualification computing device 24 may further comprise a user interface 34, such as, for example, a graphical user interface, a touch user interface, or a web-based user interface. The user interface is configured to display information regarding the chromatography column qualification parameters to the user. The user interface is also configured to receive input from the user regarding the chromatography column parameters.

The server 26 depicted in FIG. 2 can be one or a plurality of computing devices that each include a CPU or processor, a memory, and a network interface, which are coupled together by a bus or other link similar to that described for the column qualification computing device 24. The server 26 may include other types and/or numbers of components and elements in other configurations.

Communication interface(s) 22 of the system described herein can include one or more local area networks (LANs) and/or wide area networks (WANs). By way of example only, the communication interface(s) 22 can use TCP/IP over Ethernet and industry standard protocols, including hypertext transfer protocol (HTTP) and/or secure HTTP (HTTPS), although other types and/or numbers of communication networks may be utilized.

Another aspect of the present disclosure relates to a non-transitory computer readable medium having stored thereon instructions for chromatography column qualification using the gamma distribution transition analysis. These instructions comprise executable code which when executed by a processor, causes the processor to perform steps comprising, collecting column outlet signal and accumulated flow parameters at two or more intervals of at least one mobile phase transition front during a first operation of the chromatography column comprising column packing; determining a model gamma cumulative distribution curve based on the collected column outlet signal and accumulated flow parameters for the at least one mobile phase transition front using Formula Ia as described supra for a rising transition front or Formula Ib as described supra for a falling transition front; calculating a height equivalent theoretical plate (HETP) value for the at least one mobile phase transition front using Formula II as described supra and the model gamma cumulative distribution curve parameters of k, θ, and $V_i$ as described herein; and assessing quality of the chromatography column packing based on said calculated HETP value.

Another aspect of the present disclosure is directed to a chromatography column qualification device. This device comprises a processor and a memory coupled to the processor. The memory is configured to execute programmed instructions stored in the memory. These instruction include: collect column outlet signal and accumulated flow parameters at two or more intervals of at least one mobile phase transition front during a first operation of the chromatography column comprising column packing; determine a model gamma cumulative distribution curve based on the collected column outlet signal and accumulated flow parameters for the at least one mobile phase transition front using Formula Ia for a rising transition front or Formula Ib for a falling transition front as described supra; calculate a height equivalent theoretical plate (HETP) value for the at least one mobile phase transition front using Formula II as described supra and the model gamma cumulative distribution curve parameters of k, θ, and $V_i$ as described herein, and assess quality of the chromatography column packing based on said calculated HETP value.

EXAMPLES

Example 1—Application of the Gamma Distribution Transition Analysis for Column Qualification of Protein A Chromatography Columns Used in to REMICADE® (infliximab) Manufacturing Overview:

The manufacturing process of the therapeutic antibody, REMICADE® (infliximab), involves several stages, four of which involve chromatography purification. The gamma distribution transition analysis (GDTA) for column qualification was applied to two or three transitions during each of these column steps. This Example describes the application of the GDTA method to the Protein A column purification step employed during REMICADE® (infliximab) manufacturing. The purification process includes two transition fronts, i.e., equilibration and intermediate wash, that are appropriate for GDTA as described herein.

The GDTA was executed on 129 fronts from the consecutive purification of 69 batches of REMICADE® (infliximab), comprising 60 equilibration and 69 wash fronts. The gamma front distribution analysis was performed concurrently with manufacturing and did not impact the manufacturing process. All manufacturing, monitoring and controls were performed using current, effective procedures. During the column chromatography purification of REMICADE® (infliximab), conductivity (i.e., the column outlet signal) and flow of the eluent (i.e., accumulated flow) were recorded.

In addition to the application of the GDTA to column operation in real time, historical data for 285 batches processed over the course of the four previous years was also collected and analyzed as described herein. The data set included 253 equilibration fronts and 285 wash fronts, for a total of 538 historical fronts. The equilibration fronts were not generated for 32 batches in which pre-use sanitizations were performed. This data set was selected to provide an even distribution through the life of the columns and represents 11 column packs.

GDTA Protocol:

For each transition front during Protein A column purification, i.e., wash and equilibration, the conductivity and accumulated flow were recorded. Determination of the starting point was accomplished by evaluating the trends for pre-column conductivity and pressure in order to identify the point at which the column was placed inline. A spreadsheet was created and setup to retrieve flow and conductivity data from the server using a calculated 10 second interval for the duration of the front.

The conductivity data was normalized by setting the maximum value to 1 and the minimum value to 0 and scaling the other points proportionally. Additionally, the flow was converted to column volumes.

A starting gamma CDF was calculated by using the same starting $k$, $\theta$, $V_i$ parameters as the PI module. $V_i$ was subtracted from each volume value in the x term of the gamma distribution function. In order to normalize the conductivity, which was increasing during the purification, the conductivity values were set to 0 for volumes less than $V_i$ and the maximum was set to 1.

The difference (error) between each conductivity value and the model fit for each volume point was calculated. Additionally, the sum of squares for the error between 0.5 and 1.8 CV was calculated. The best fit gamma CDF parameters were calculated using the Excel solver to find the $k$, $\theta$, and $V_i$ parameters that produced a model curve with the minimum value for the sum of squares using $$C = 1 - \frac{1}{\Gamma(k)} \gamma\left(k, \frac{V - V_i}{\theta}\right).$$ Formula Ia The solver was run for 10,000 iterations using the GRG non-linear method with constraints of $k \geq 0.0001$ and $V_i \geq 0$ to ensure that a closest fit was reached.

The following parameters were calculated from the final values of $k$, $\theta$, and $V_i$:

$\text{Mean}(V_m), \mu = k\theta + V_i,$ $\text{Variance}, \sigma^2 (\text{sigma squared}) = k\theta^2$ $\text{Mode} = (k-1)\theta + V_i$ $$HETP = \frac{L}{N_p} = \frac{\sigma^2}{\mu^2} L = \frac{k\theta^2 L}{(k\theta + V_i)}$$

The average flow rate and pre-column pressure was calculated for the period from 0.5 to 1.8 CV for each front.

Analysis and Evaluation of Acceptance Criteria:

Normality

Results for HETP and SS for both the equilibration and wash fronts were evaluated for normality by creating a probability plot. In the probability plots (FIGS. 3-12) the data points (results for HETP or SS) represent the actual cumulative distribution observed in the sample. The lines represent the fitted cumulative distribution and the upper and lower confidence intervals based on a normal distribution using the parameters estimated from the sample. The percentile scale is transformed so the fitted distribution forms a straight line. The HETP and SS data sets are each bounded by 0 on the lower end, however, the normal distribution model suggests negative values. The resulting probability plots show a curved shape. See FIGS. 3-6. Thus, the results fit better using a log transformation. See FIGS. 7-10 for the probability plot of the log transformed data.

Figure 11:
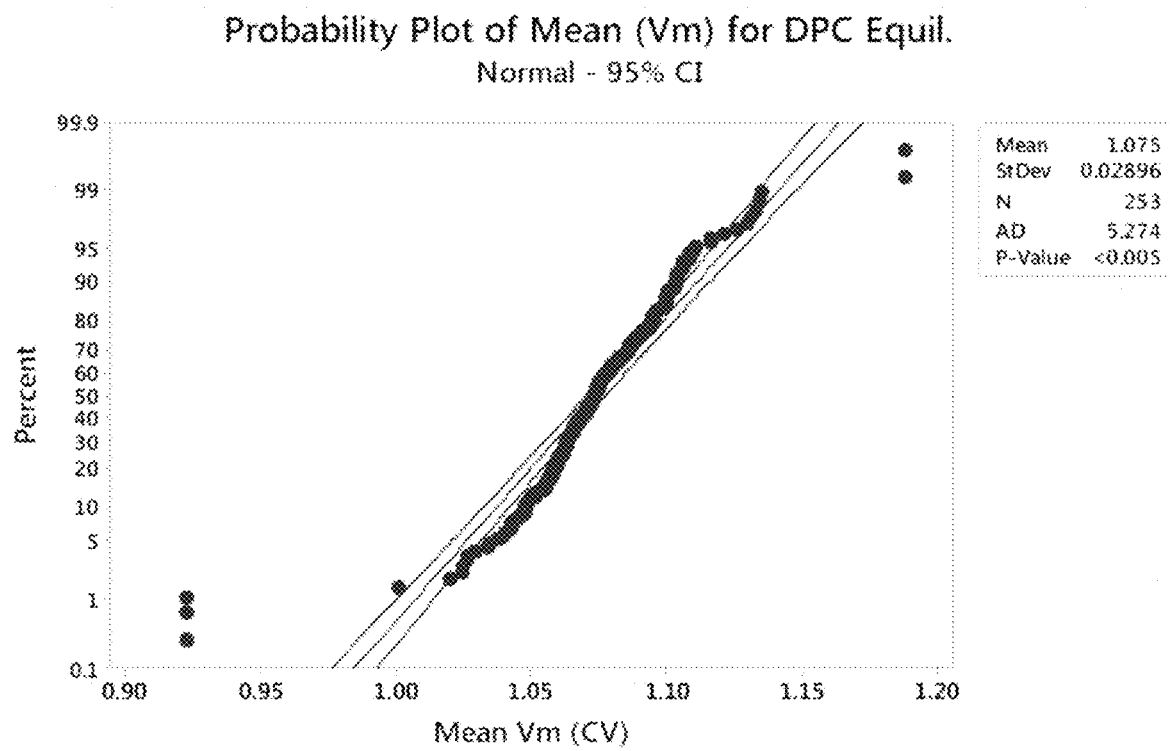
FIG. 11 is a probability plot of the Mean ($V_m$) for Protein A column equilibration.
Figure 12:
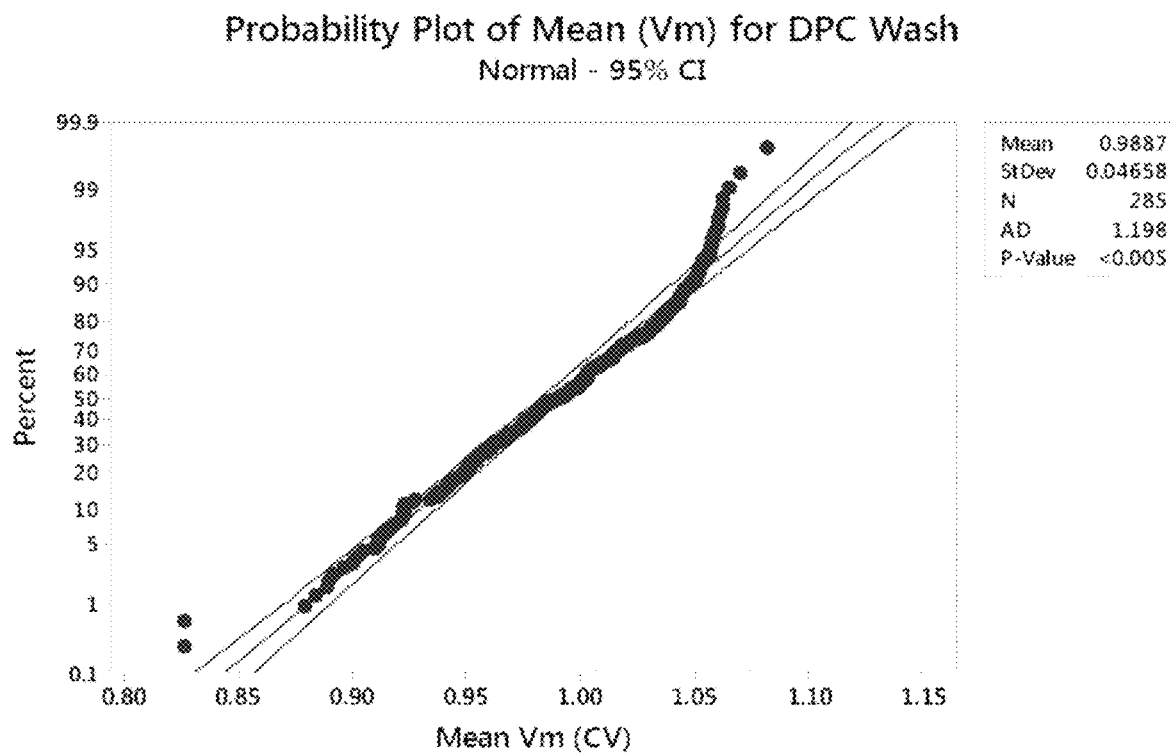
FIG. 12 is a probability plot of the Mean ($V_m$) for Protein A column wash front.

Data for the Mean ($V_m$) was also evaluated for normality. FIG. 11 and FIG. 12 show that the data fits the normal distribution, with only a few outliers. Thus, no transformation was needed. This parameter was not specified in the protocol but provides a useful assurance that the curve fit is valid. Control limits for this parameter will also be generated from this analysis.

Identification of Outliers and Causes of Variation.

In order to identify outliers and assess variability in the results, control charts for each parameter were generated. See FIGS. 13-22. Control charts used the transformed data for the HETP and SS, where natural log transformation was applied. The data is also plotted in a time series plot with the transformed upper control limit for each of these parameters.

Figure 13:
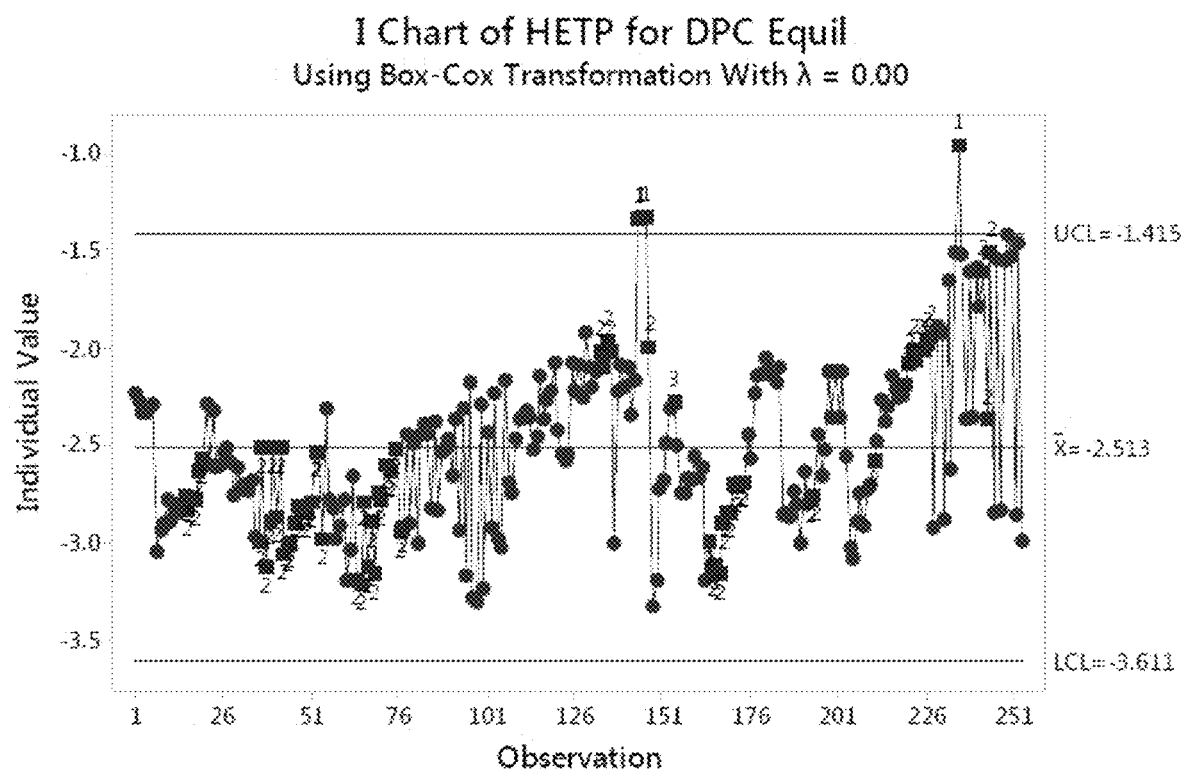
FIG. 13 is a control chart of HETP for Protein A column equilibration front with natural log ($\lambda$=0) transformation. UCL=upper control limit; LCL=lower control limit. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.
Figure 18:
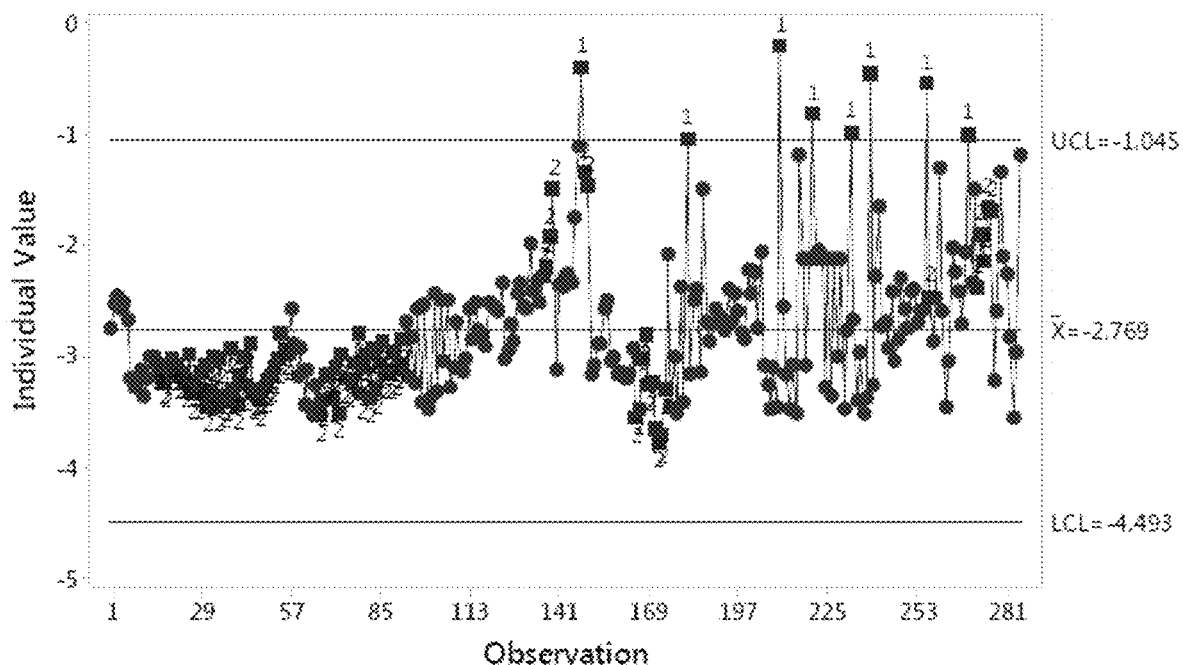
FIG. 18 is a control chart of HETP for Protein A column wash front with natural log ($\lambda$=0) transformation. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.

HETP:

A number of outliers and trends are apparent in the HETP results for both Equilibration and Wash fronts. Additionally, FIG. 13 and FIG. 18 show trends in the data based on Shewhart rules 1, 2 and 3, represented by squares in the figures and numbered according to the following.

| Test | Rule |
|---|---|
| 1 | 1 point is outside the control limits. |
| 2 | 8 points on the same side of the center line. |
| 3 | 6 consecutive points are steadily increasing or decreasing. |

The batches associated with these excursions were not excluded from the analysis as they are representative of the acceptable process.

Both of the control charts (FIG. 13 and FIG. 18) show a number of Shewhart rule 1 violations, which also exceeds the control limits. In each case the issues were identified and corrected by reconditioning the columns.

Figure 23:
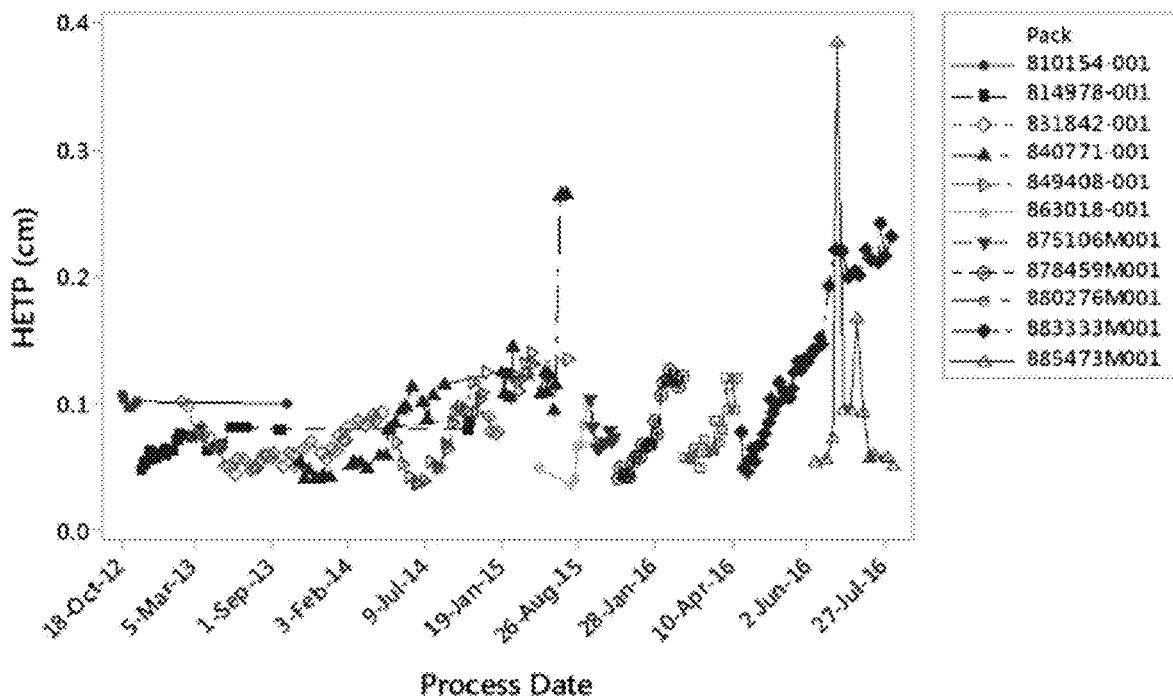
FIG. 23 is a time series plot of HETP results for direct product capture (DPC) Protein A column equilibration front grouped by column pack.
Figure 24:
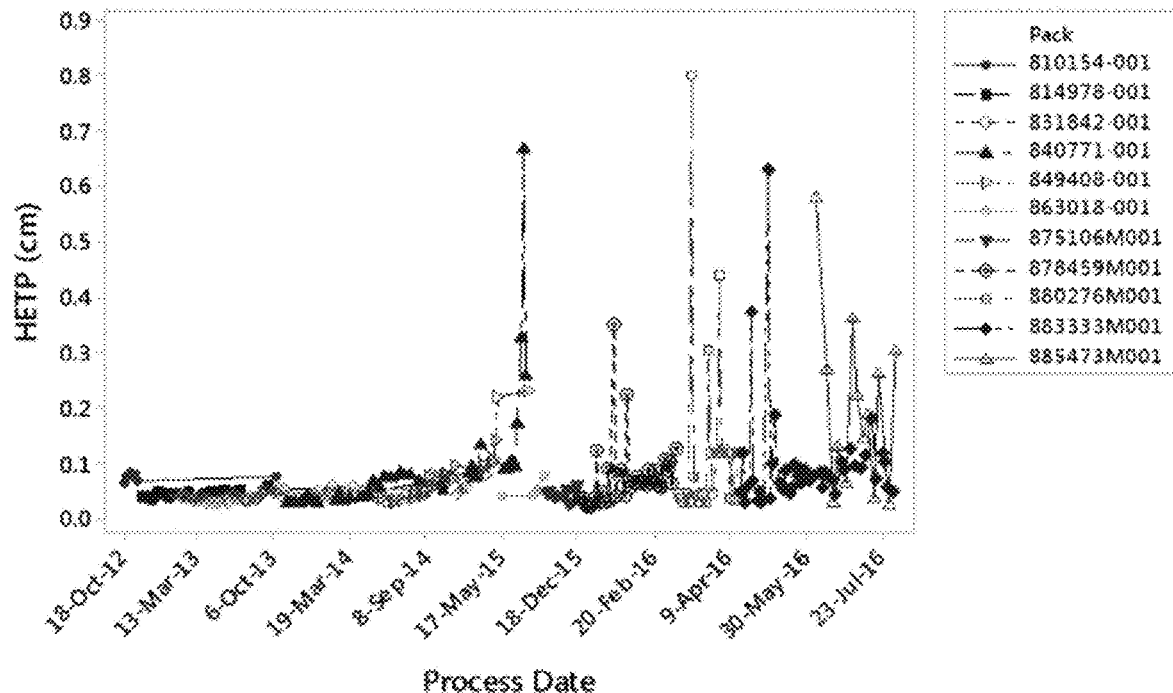
FIG. 24 is a time series plot of HETP results for DPC Protein A column wash front grouped by column pack.
Figure 25:
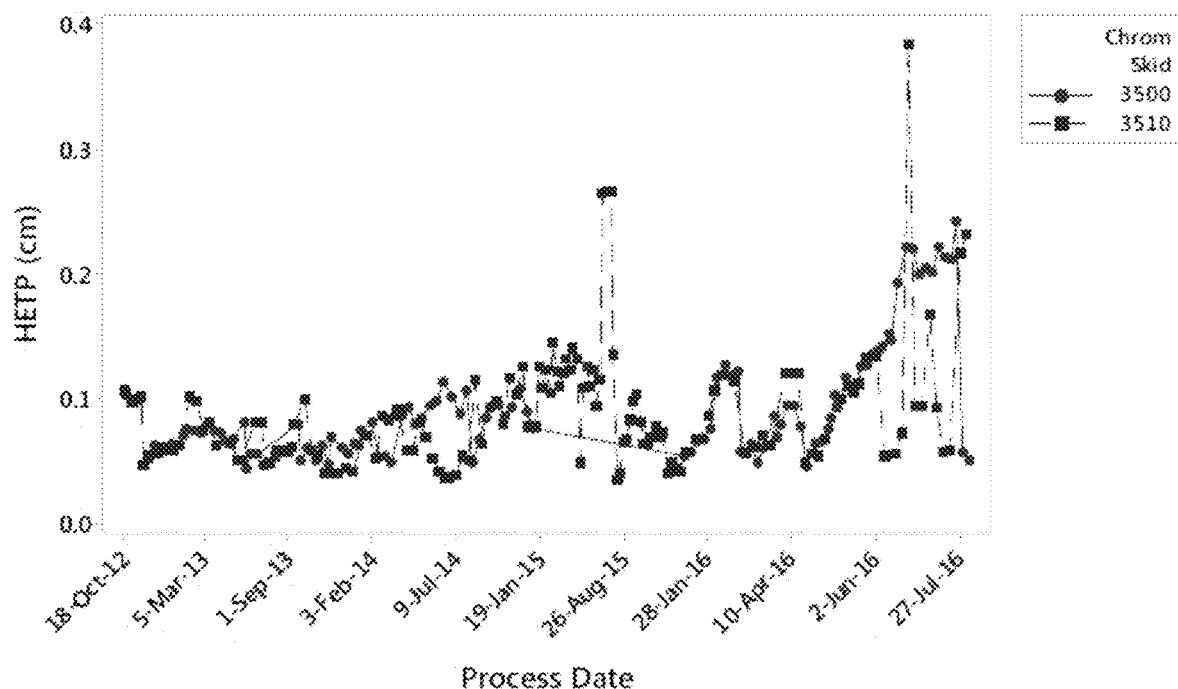
FIG. 25 is a time series plot of HETP results for DPC Protein A column equilibration front grouped by skid.
Figure 26:
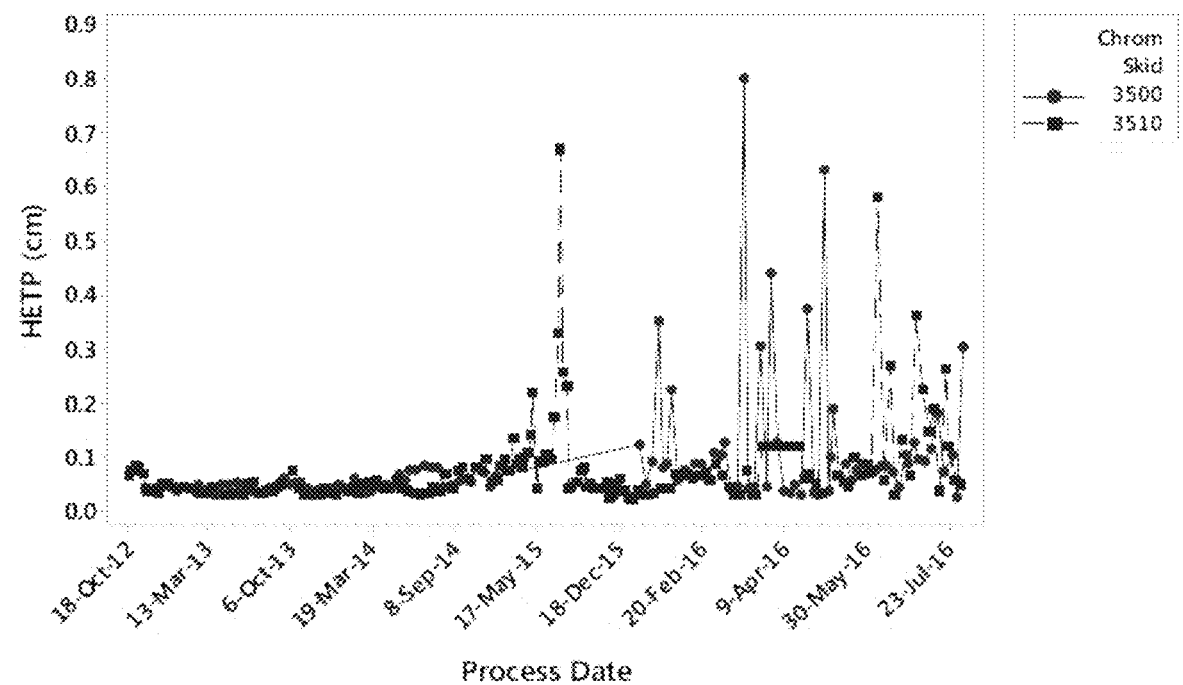
FIG. 26 is a time series plot of HETP results for DPC Protein A column wash front grouped by skid.
Figure 27:
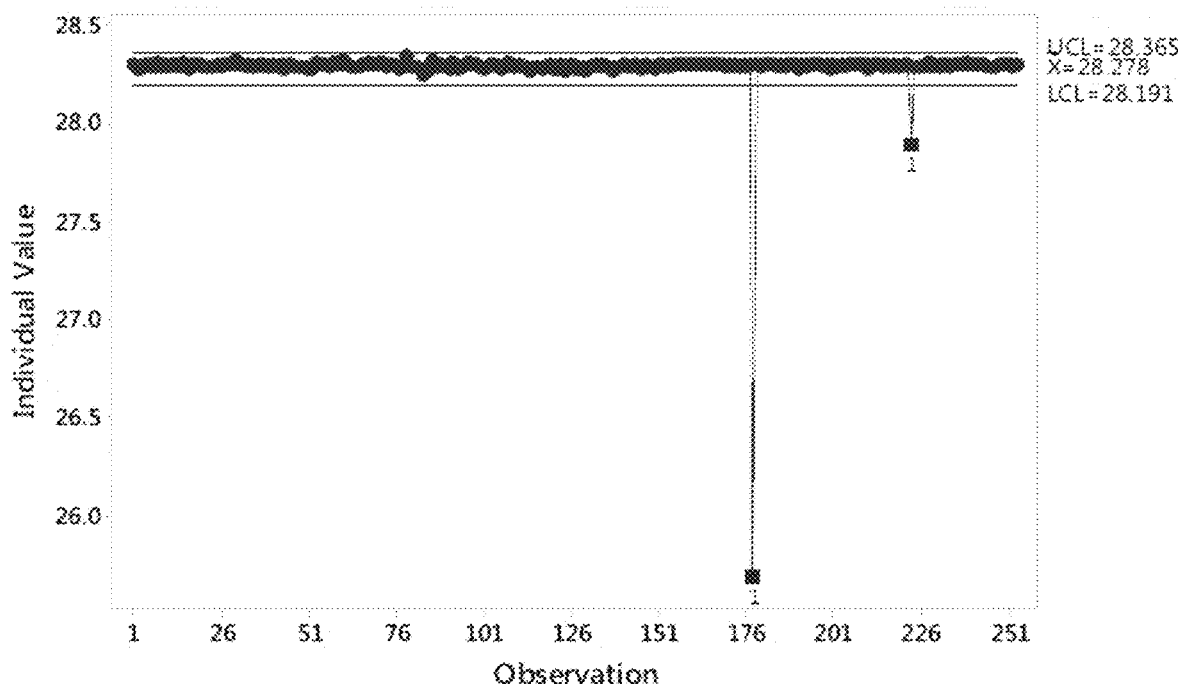
FIG. 27 is chart showing the average flow for DPC Protein A column equilibration. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.
Figure 28:
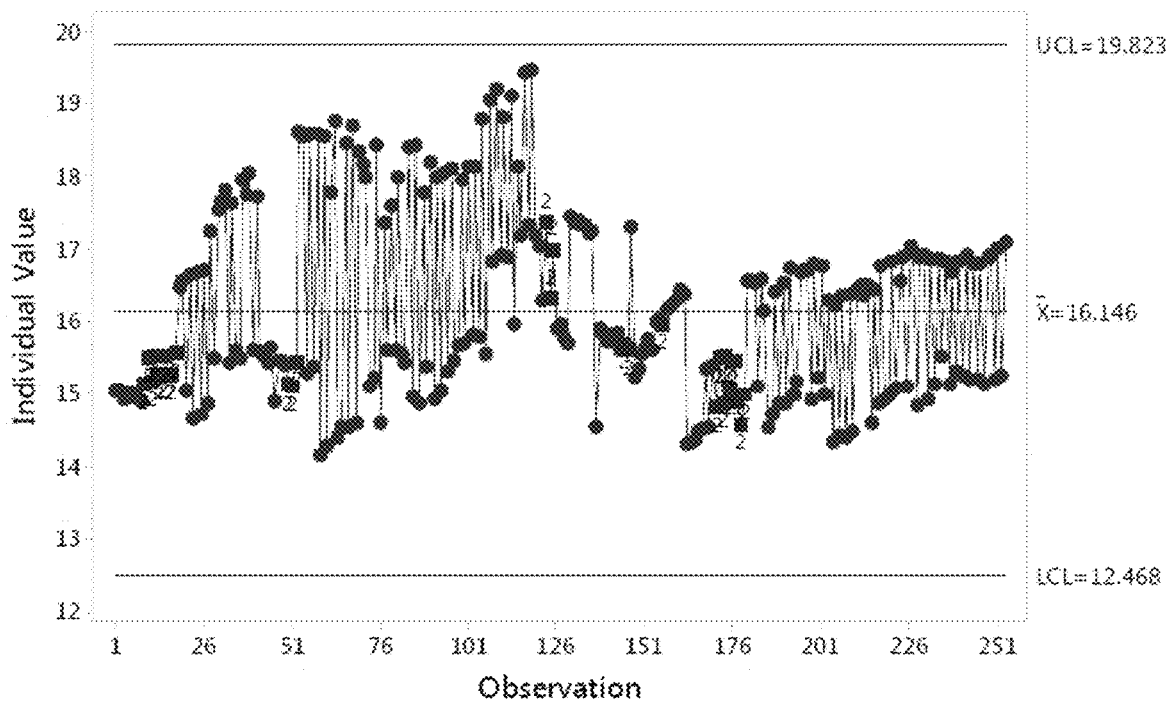
FIG. 28 is a chart of the average pre-column pressure during equilibration. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.
Figure 29:
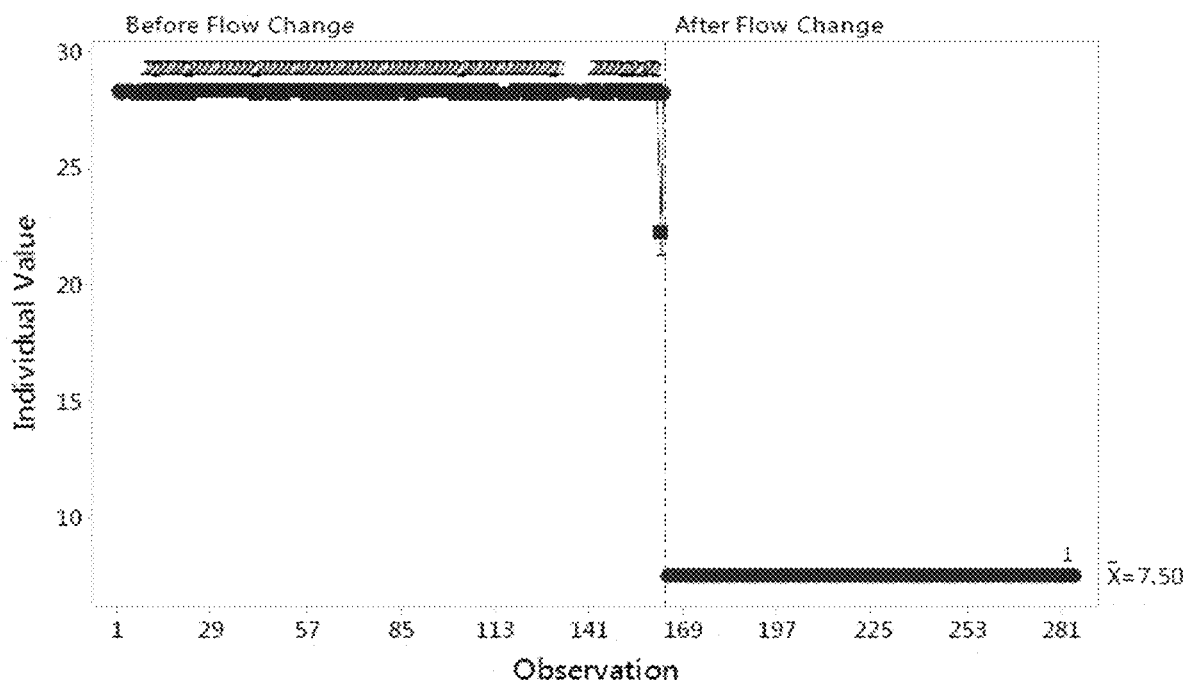
FIG. 29 is a chart of the average wash flow rate for DPC Protein A column wash front. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.
Figure 30:
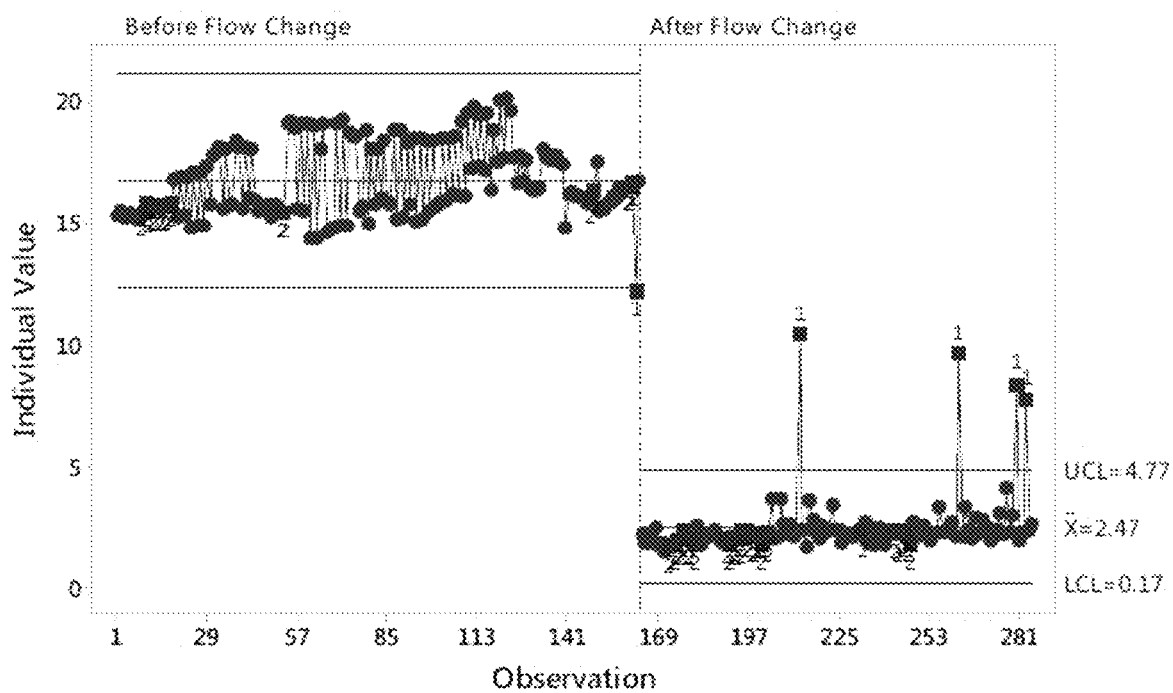
FIG. 30 is a chart of the average wash pressure for the DPC Protein A column wash front. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.

As expected, a number of runs met the criteria for rule 2 and 3 due to variation in the column packs. In order to further assess the trends, time series plots were prepared with data grouped by column pack (FIGS. 23-24) and skid (FIGS. 25-26). These charts show that much of the special cause variation is attributed to column degradation and some isolated excursions. Trends of increasing HETP are apparent for each column over time for the equilibration front (FIG. 23). Excursions observed for the Wash front appear to be isolated to one skid or the other at different times (FIG. 26), suggesting that there may be a source of column performance variability in the skid.

Figure 15:
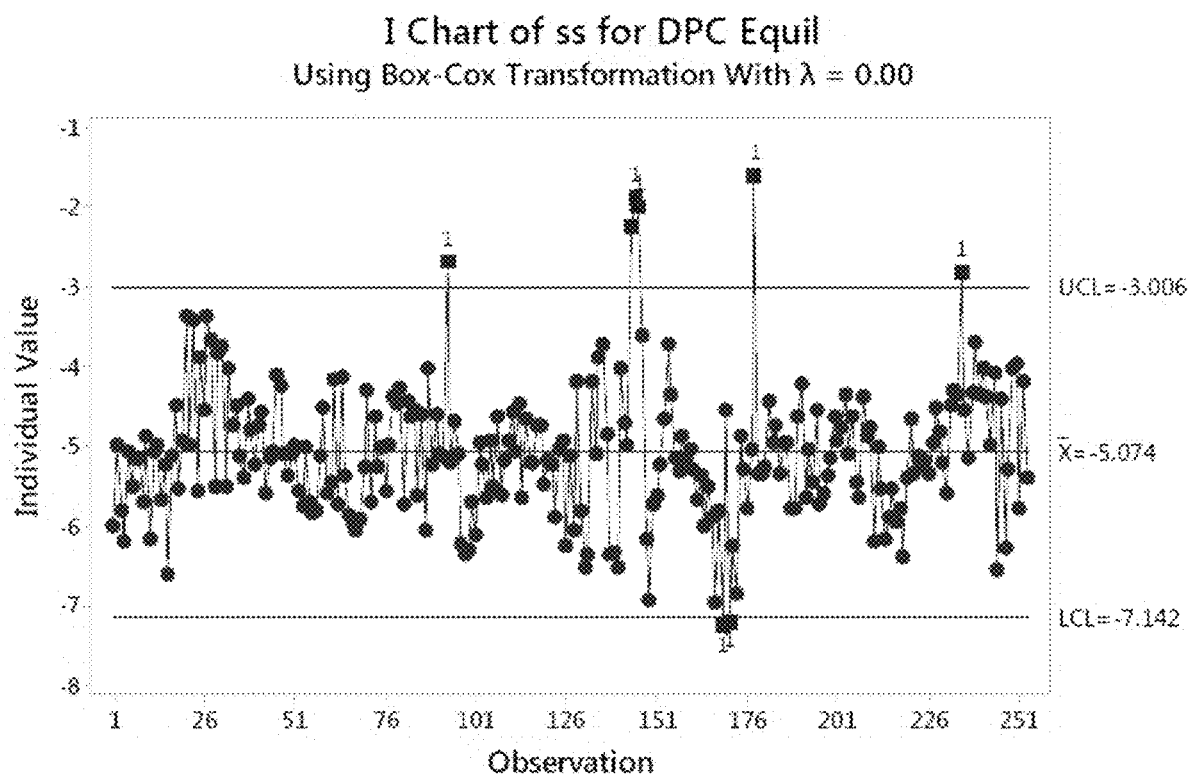
FIG. 15 is a control chart of the SS for Protein A column equilibration front with natural log ($\lambda$=0) transformation. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.
Figure 20:
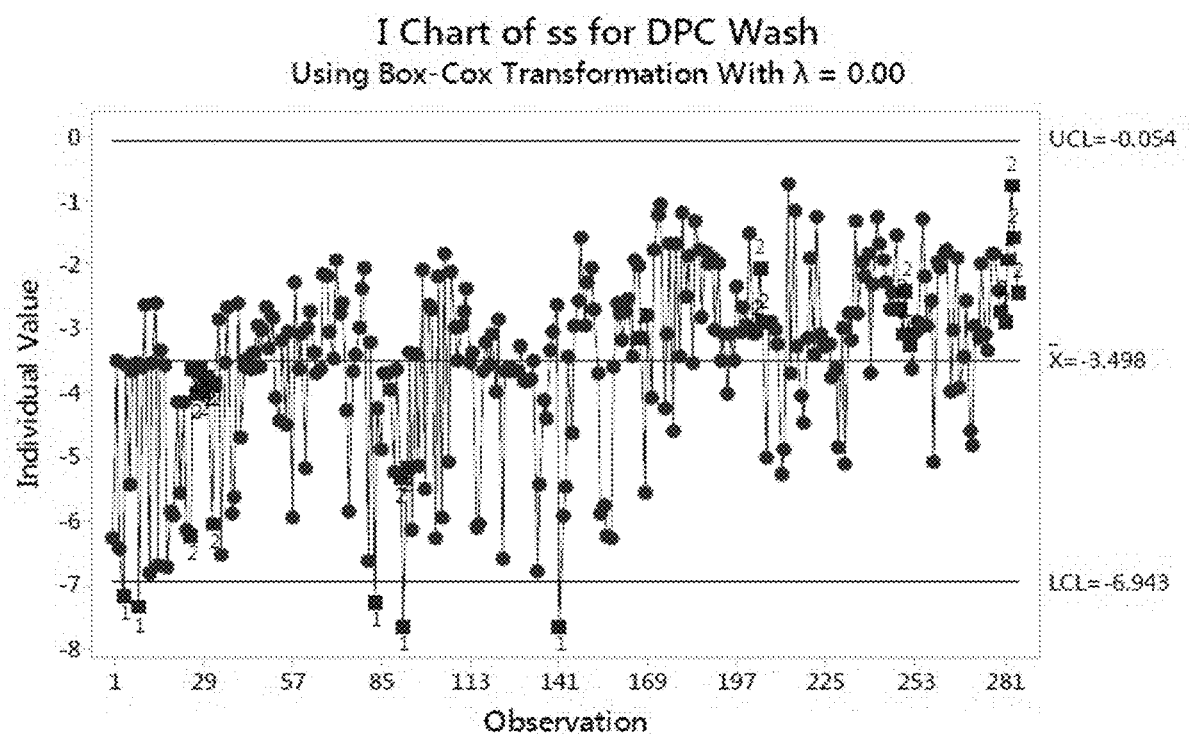
FIG. 20 is a control chart for SS for Protein A column wash front with natural log ($\lambda$=0) transformation. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.
Figure 21:
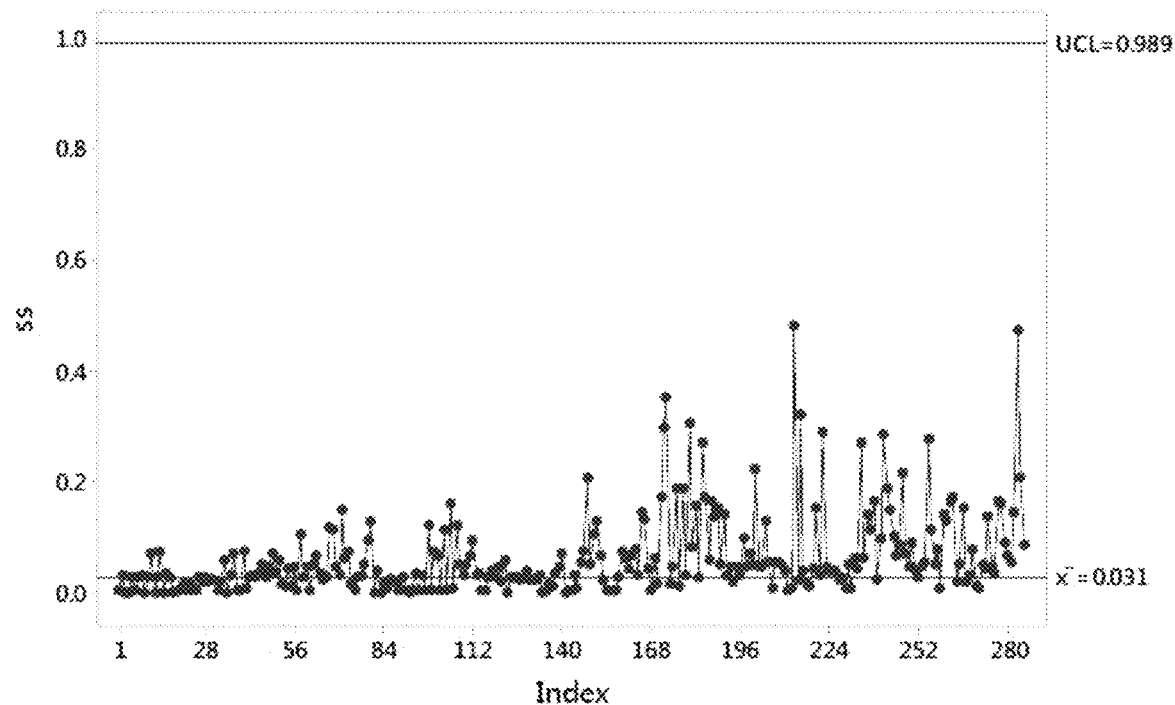
FIG. 21 is a time series plot of SS for Protein A column wash front. UCL is derived from transformed data in FIG. 20.
Figure 22:
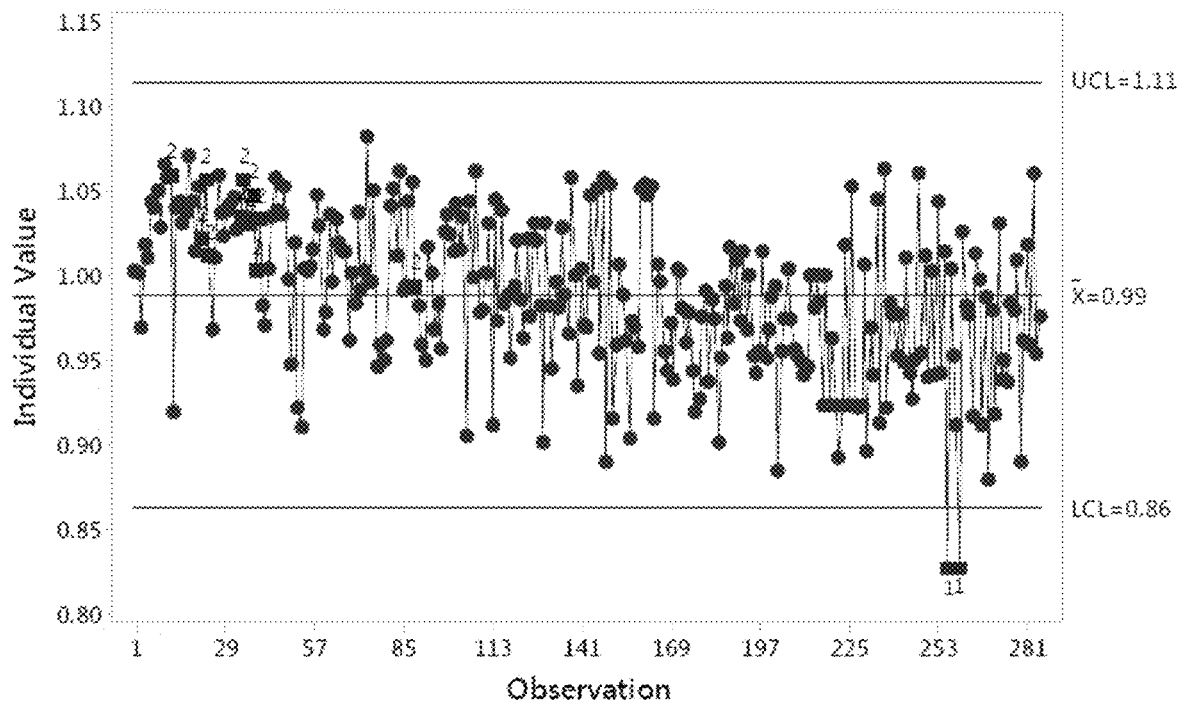
FIG. 22 is a control chart for Mean ($V_m$) for Protein A column wash front. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.

Sum of Squares (SS):

The sum of squares is a measure of how well the gamma distribution fits the process data. This measure will provide a check to ensure that the HETP result is valid. Control charts for the transformed data are shown in FIG. 15 and FIG. 20 for equilibration and wash, respectively. This measure only has an upper control limit. FIG. 15 shows 6 points where the upper control limit is exceeded. Four of these are associated with higher HETP. Batch 880572M had a flow disruption during the front which caused the SS to be high but did not impact HETP.

Evaluation of Flow and Pressure.

The average flow rate and pre-column pressure for the data set was evaluated to identify any outliers. The relationship between the differences identified and the results was assessed.

Figure 31:
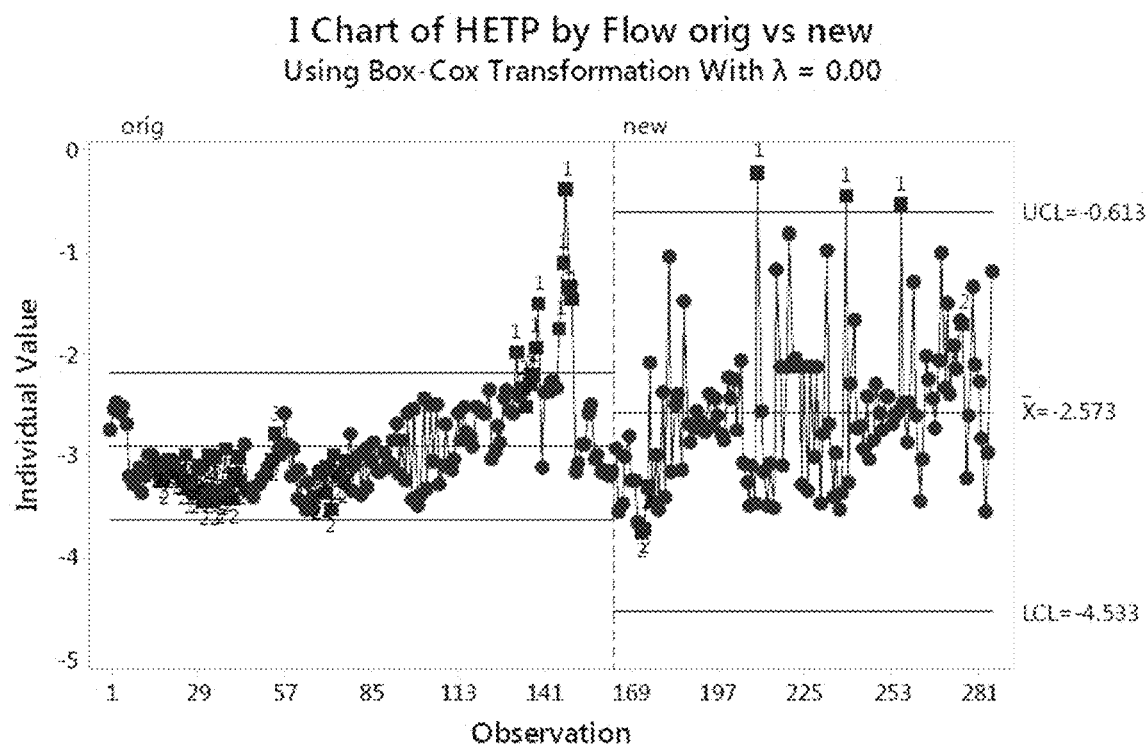
FIG. 31 is a chart showing the HETP before and after changing the wash flow rate. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.

Flow rate and pre-column pressure are trended in FIGS. 27-30. The charts show excellent control of flow rate for each of the steps. The Wash flow rate was changed during this assessment. Pre-Column pressure shows variations related to the skid and columns but is generally stable within a range. FIG. 31 shows that the HETP value is not significantly impacted by the wash flow rate change.

Control Limits for Protein A Column

HETP:

HETP is directly related to the column performance and is also affected by other factors in the system that may increase dispersion. The result must be >0. The control limits for HETP are best determined by using the natural log Box-Cox transformation ($\lambda=0$), as shown in FIG. 13 for the equilibration and FIG. 18 for the wash front. The control charts show control limits for the transformed data calculated by Minitab using the mean+/−3 standard deviations (see also Table 2 below). Standard deviation is determined based on the average moving range. A moving range of 100 was selected to account for the variation in column performance over the column life. The upper and lower control limits are reverse transformed ($e^x$) to determine the control limits for the untransformed data.

Figure 14:
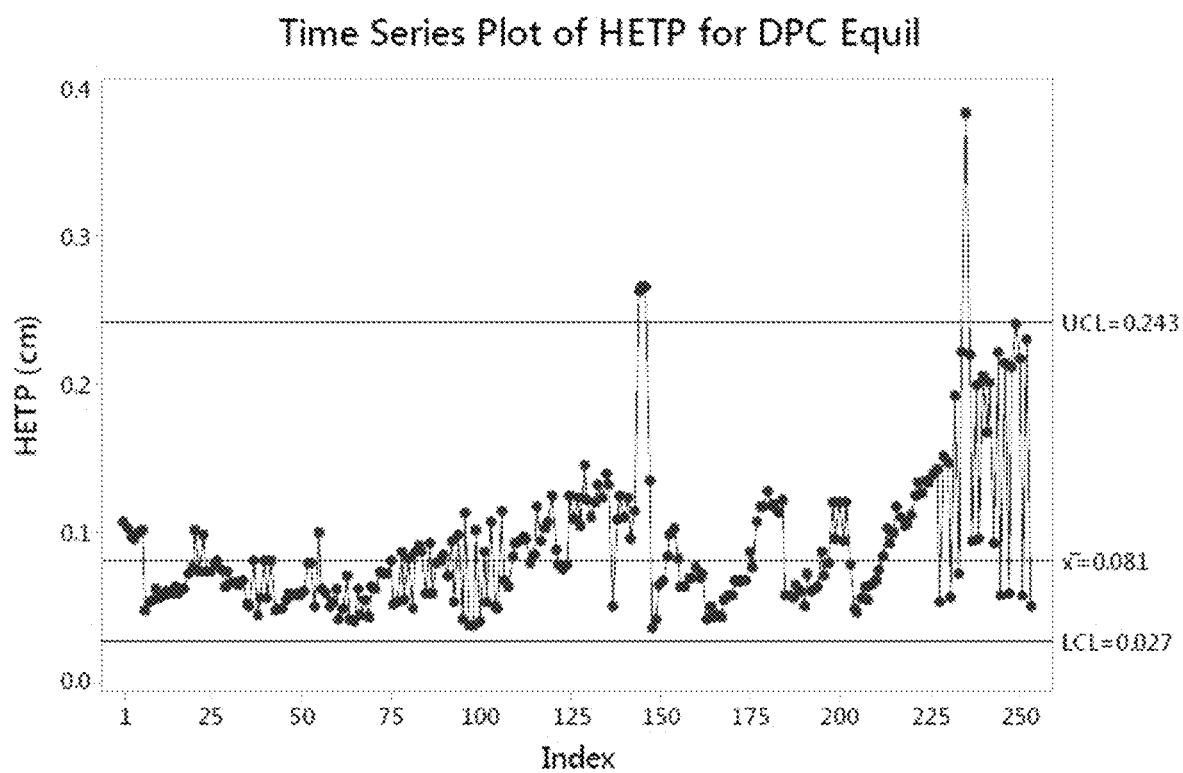
FIG. 14 is a time series plot of HETP for Protein A column equilibration front. The UCL is derived from transformed data in FIG. 13.
Figure 19:
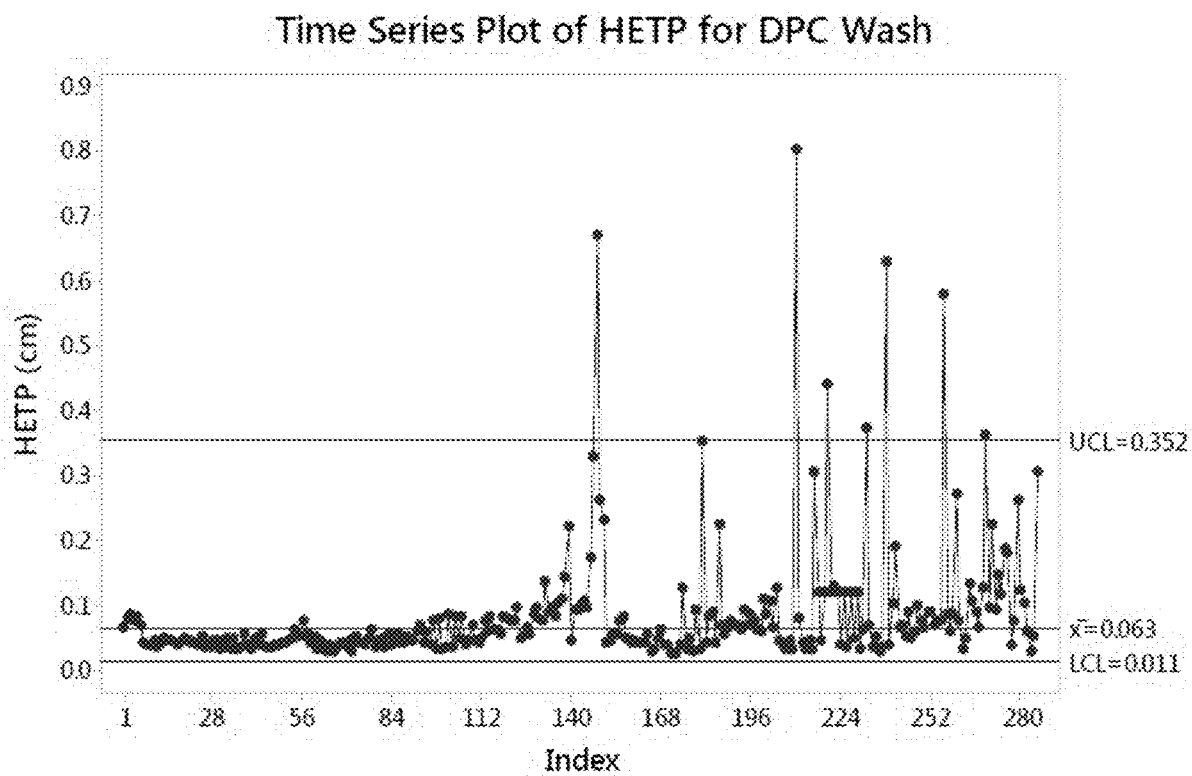
FIG. 19 is a time series plot of HETP for Protein A column wash front. UCL is derived from transformed data in FIG. 18.

A time series plot for each front's HETP results and control limits is shown in FIG. 14 and FIG. 19. Operation within these limits is expected to produce acceptable chromatographic performance based on this historical review. Values above the upper control limits may indicate column flow issues and should be evaluated further. Values below the lower control limits may be indicative of a calculation error.

Figure 16:
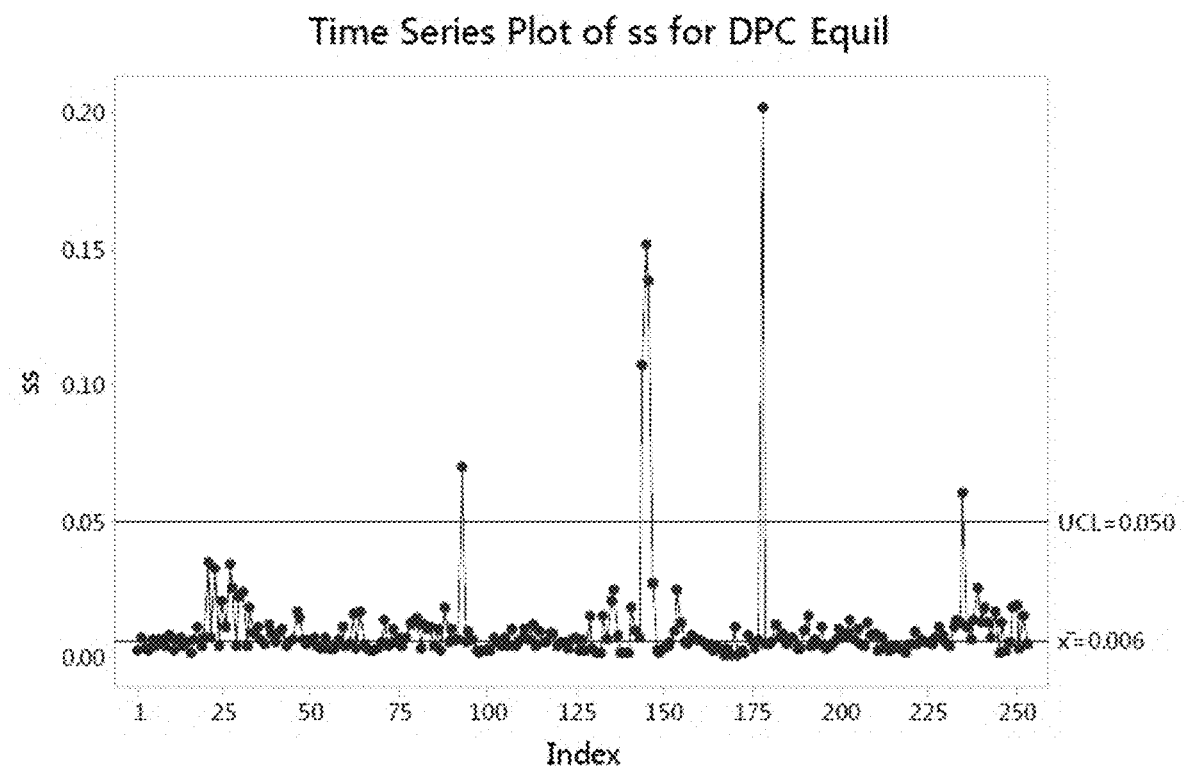
FIG. 16 is a time series plot of SS for Protein A column equilibration front. The UCL is derived from transformed data in FIG. 15.
Figure 17:
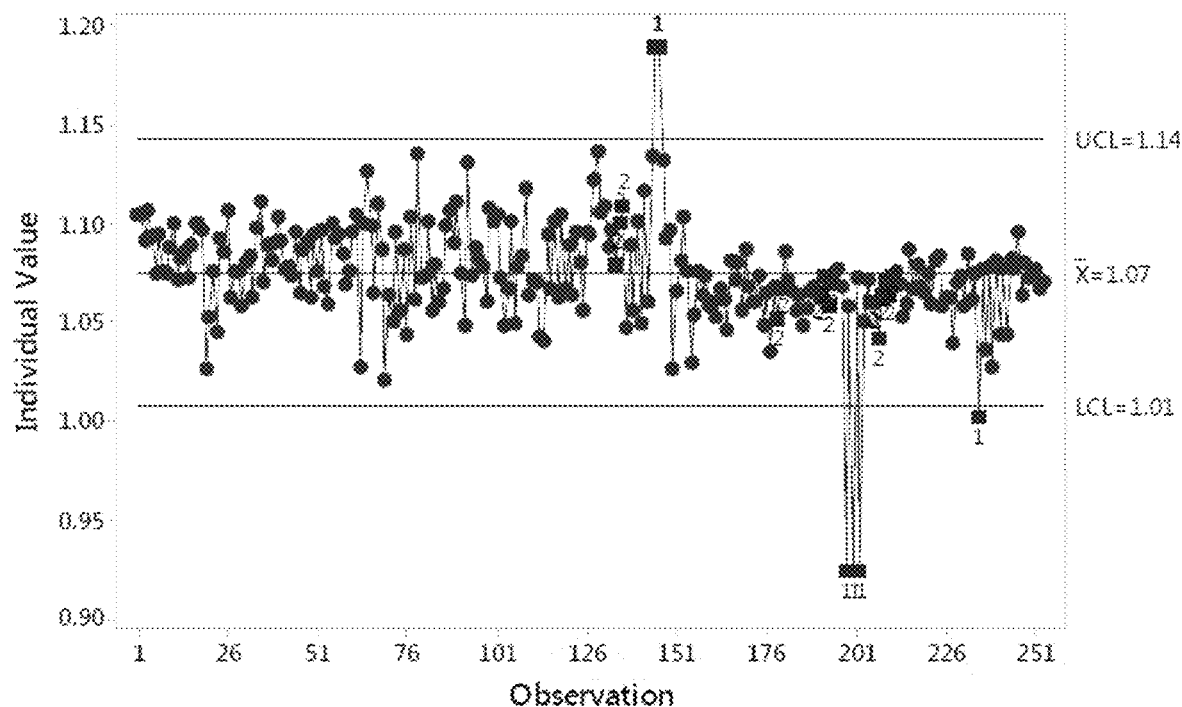
FIG. 17 is a control chart of the Mean ($V_m$) for Protein A column equilibration front. Numbered points on the chart show outliers and/or trends apparent in the HETP results based on Shewhart rules 1, 2 and 3, i.e., 1 represents 1 point outside the control limits, 2 represents 8 points on the same side of the center line, and 3 represents 6 consecutive points steadily increasing or decreasing.

Sum of Squares (SS):

The SS is a measure of how well the gamma distribution model fits the data. This measure is used to ensure that HETP values calculated using the GDTA method represent the process data. There is no lower limit and the result must be >0. The upper control limit for SS is best determined by using the natural log Box-Cox transformation ($\lambda=0$), as shown in FIG. 15 for the equilibration front and FIG. 20 for the wash front. The control charts show control limits for the transformed data calculated by Minitab using the mean+/−3 standard deviations. Standard deviation is determined based on the average moving range. A moving range of 100 was selected to account for the variation in column performance over the column life. The control charts show upper control limits for the transformed data which are reverse transformed to give 0.050 and 0.989 for the Equilibration and Wash fronts, respectively (see Table 2). A time series plot for each front's SS results and control limits is shown in FIG. 16 and FIG. 20. Results within the limits will ensure that the model fits the data as well as historical results. If the result is outside of this range, a special cause is likely.

Mean:

The mean was added as a second measure of the accuracy of the gamma distribution model. The mean represents the theoretical center of mass for the front and should always be near 1 column volume unless there are other factors in the system that cause it to shift, such as large extra column volume or interaction between the mobile phase and resin. The mean values for both equilibration and wash fronts are roughly normally distributed and do not need transformation, see FIG. 11 and FIG. 12. The mean for the equilibration front is tightly distributed around 1.07 CV with some outliers present on either side and approaching 1.2 on the high side, see FIG. 17. The wash front shows slightly more variation and is centered at 0.99 CV with several low outliers approaching 0.8, see FIG. 22. It is recommended to apply control limits of 0.80 to 1.20 CV for the mean for both fronts (see Table 2). This is appropriate because the mean is not a measure of the column performance but is used as a check to ensure that the analysis was appropriate. The tighter control limits would result in unnecessary sensitivity for this check.

TABLE 2

Recommended HETP, SS, and Mean Control Limits for Protein A Column Purification during REMICADE ® (infliximab) Manufacturing

| Front | Parameter | UCL | LCL |
|---|---|---|---|
| Equilibration | HETP | 0.243 | 0.027 |
|  | SS | 0.050 | NA |
|  | Mean | 1.20 | 0.80 |
| Wash | HETP | 0.352 | 0.011 |
|  | SS | 0.989 | NA |
|  | Mean | 1.20 | 0.80 |

Example 2—Application of the Gamma Distribution Transition Analysis for Detection of Sub-Optimal Performance of Protein A Chromatography Columns Used in to REMICADE® (Infliximab) Manufacturing The manufacturing process of the therapeutic antibody, REMICADE® (infliximab), involves several stages, four of which involve chromatography purification. The gamma distribution transition analysis (GDTA) for column qualification was applied to two or three transitions during each of these column steps. This Example describes the application of the GDTA method to the Protein A column purification step employed REMICADE® (infliximab) manufacturing. The purification process includes two transition fronts, i.e., equilibration and intermediate wash, that are appropriate for GDTA as described herein.

The GDTA was executed on 45 Equilibration fronts from the consecutive purification of 45 batches of REMICADE® (infliximab), comprising 23 batches processed on column pack 883333M001 and 22 batches processed on column pack 885473M001. The gamma front distribution analysis was performed concurrently with manufacturing and did not impact the manufacturing process. All manufacturing, monitoring and controls were performed using current, effective procedures. During the column chromatography purification of REMICADE® (infliximab), conductivity (i.e., the column outlet signal) and flow of the eluent (i.e., accumulated flow) were recorded.

Figure 32:
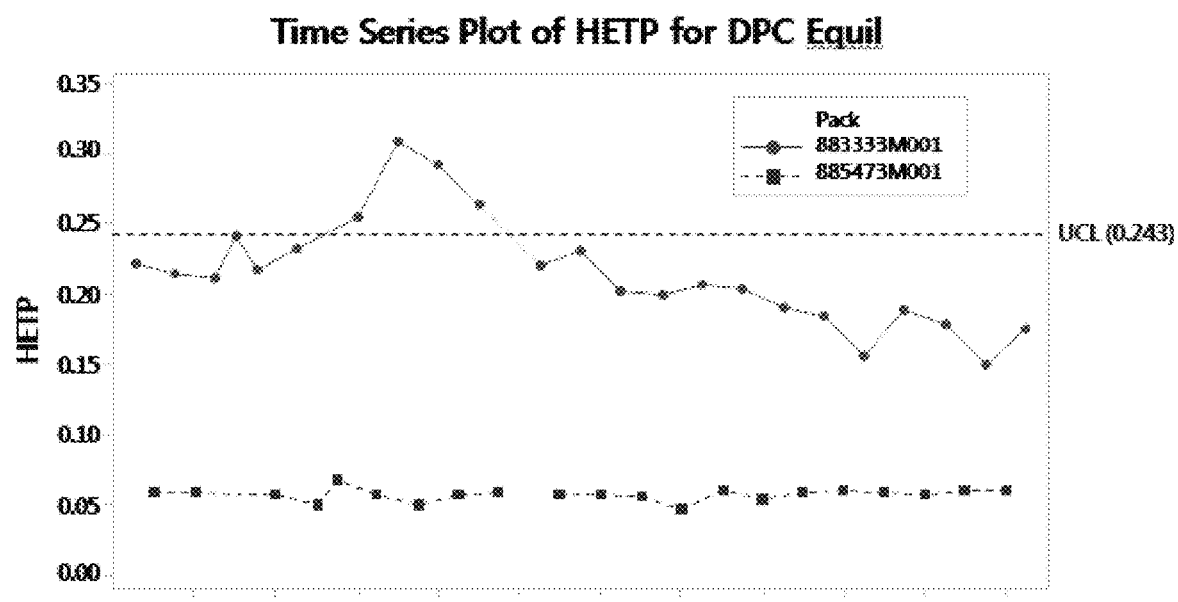
FIG. 32 is a time series plot of HETP for two different Protein A column packs as assessed over the equilibration front for 45 batches of REMICADE® (infliximab).

Trending of Equilibration HETP results for the 45 batches, see FIG. 32, showed a significant difference between column packs. Current controls for column evaluation did not identify any difference between the two column packs. Evaluation of the batch yield showed a significant ($p=0.001$) difference between the batches processed on the two column packs, estimated at 4.3% lower for the column pack with the higher HETP values. Other potential factors were evaluated and showed no correlation to the yield difference. Thus, the conclusion from this analysis is that the column performance difference caused lower yield. Based on this finding, the lower yielding column was conditioned to improve column packing before continued use. This example demonstrates the sensitivity of the GDTA method in assessing chromatography column quality.

Example 3—Application of the Gamma Distribution Transition Analysis for Column Qualification of SP-Sepharose High Performance Chromatography Columns Used in to REMICADE® (Infliximab) Manufacturing Overview:

As discussed above, the manufacturing process of REMICADE® (infliximab) involves several stages, four of which involve chromatography purification. This Example describes the application of the GDTA method to the SP-Sepharose High Performance (SPHP) column purification step employed REMICADE® (infliximab) manufacturing. The SPHP column is a cation exchange chromatography column. The purification process includes three transition fronts, i.e., equilibration, WFI flush, and storage fronts, that are appropriate for GDTA as described herein.

The GDTA was executed on 69 fronts from the purification of 23 batches of REMICADE® (infliximab), comprising 23 equilibration, WFI flush, and storage fronts. The gamma front distribution analysis was performed concurrently with manufacturing and did not impact the manufacturing process. All manufacturing, monitoring and controls were performed using current, effective procedures. During the column chromatography purification of REMICADE® (infliximab), conductivity (i.e., the column outlet signal) and flow of the eluent (i.e., accumulated flow) were recorded.

In addition to the application of the GDTA to column operation in real time, historical data for 189 transition fronts processed over the course of the four previous years was also collected and analyzed as described herein. The data set included 64 equilibration fronts, 63 WFI flush fronts, and 62 storage fronts. This data set was selected to provide an even distribution through the life of the columns and represents 6 column packs.

The GDTA for the SPHP column fronts was carried out as described in Example 1 above. This analysis produced measurements for HETP, SS and mean for each front. Control limits that were derived for each of these three parameters based on statistical evaluation are listed in Table 3 below.

Figure 33:
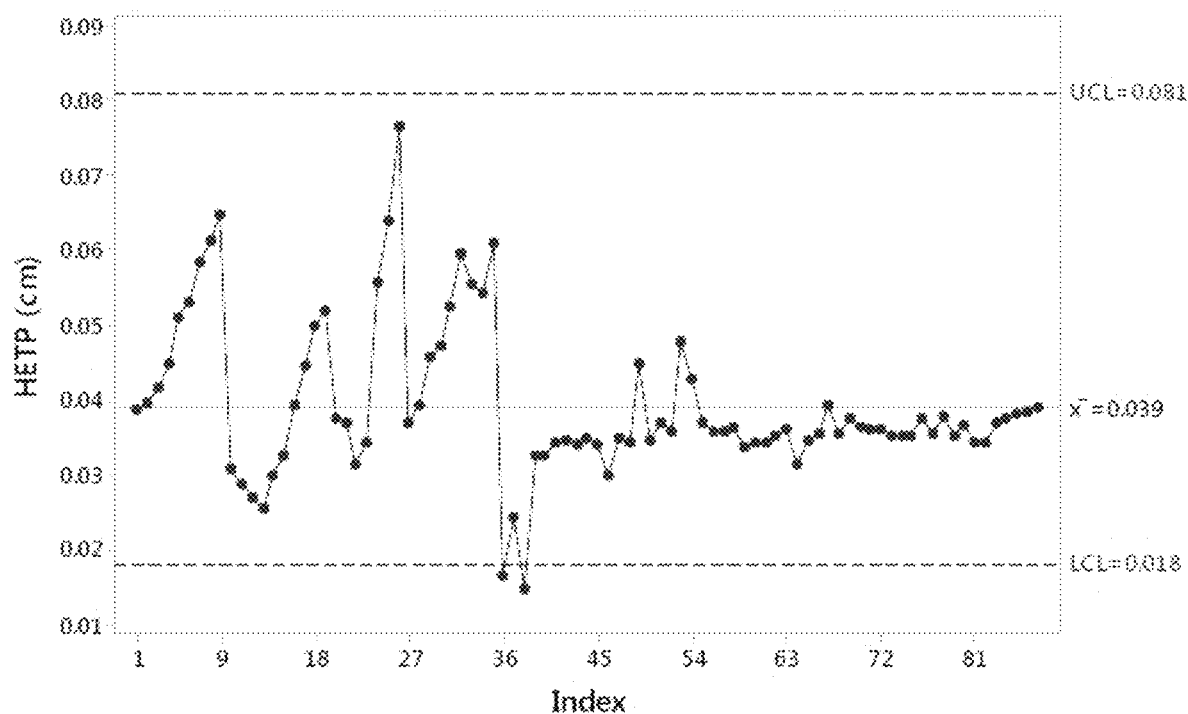
FIG. 33 is a time series plot of HETP for SP-Sepharose High Performance (SPHP) column equilibration front. Control limits are derived from the natural log Box-Cox transformation data.
Figure 34:
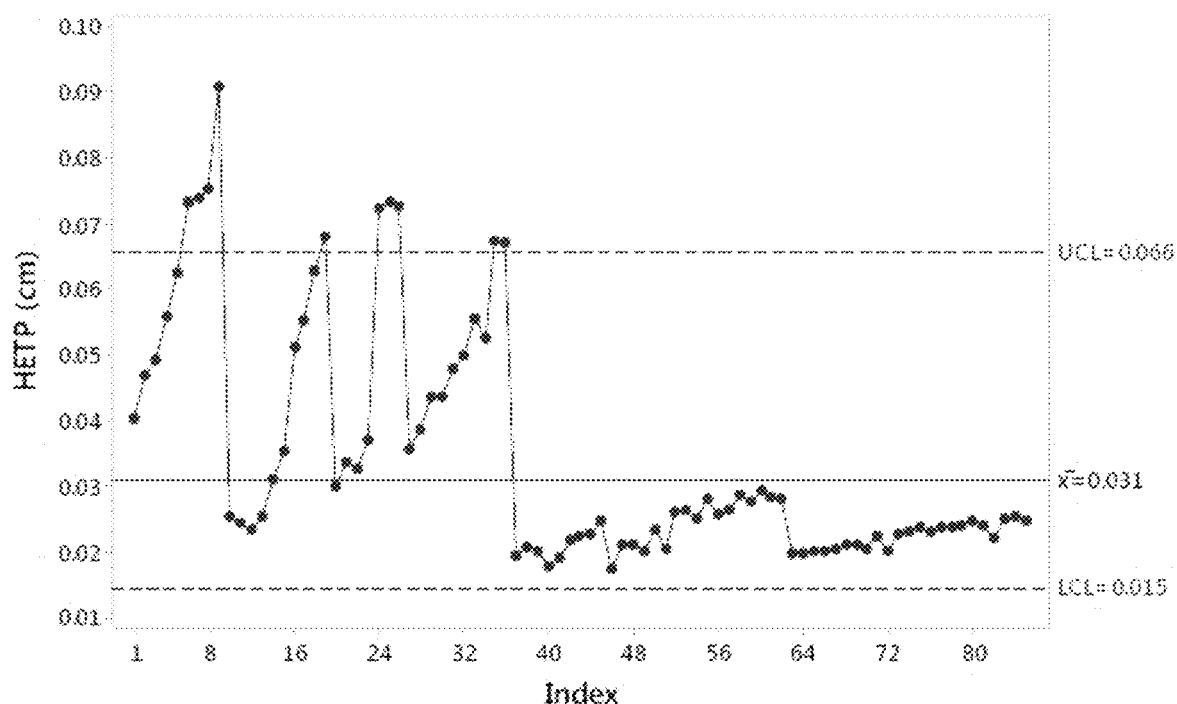
FIG. 34 is a time series plot of HETP for SPHP column WFI flush front. Control limits are derived from the natural log Box-Cox transformation data.
Figure 35:
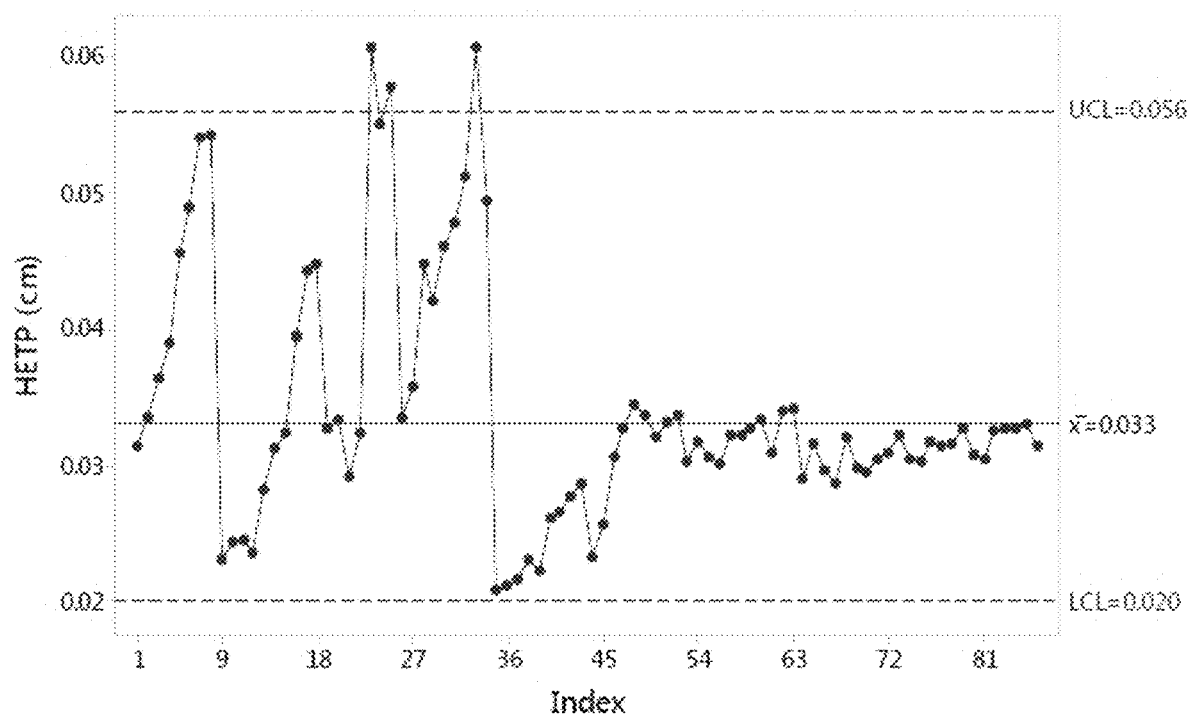
FIG. 35 is a time series plot of HETP for SPHP column storage front. Control limits are derived from the natural log Box-Cox transformation data.

Control Limits for SPHP Column:

HETP:

HETP is directly related to the column performance and is also affected by other factors in the system that may increase dispersion. The result must be >0. The control limits for HETP are best determined by using the natural log Box-Cox transformation ($\lambda=0$). The control limits for the transformed data were calculated by Minitab using the mean+/−3 standard deviations. Standard deviation is determined based on the average moving range. A moving range of 25 was selected to account for the variation in column performance over the column life. The upper and lower control limits are reverse transformed ($e^x$) to determine the control limits for the untransformed data. A time series plot for each front's HETP results and control limits is shown in FIG. 33 (equilibration front), FIG. 34 (WFI flush front), and FIG. 35 (storage front). Operation within these limits is expected to produce acceptable chromatographic performance based on this historical review. Values above the upper control limits may indicate column flow issues and should be evaluated further. Values below the lower control limits may be indicative of a calculation error.

Sum of Squares (SS):

The SS is a measure of how well the gamma distribution model fits the data. This measure will be used to ensure that HETP values calculated using the GDTA method represent the process data. There is no lower limit and the result must be >0. The upper control limit for SS is best determined by using the natural log Box-Cox transformation ($\lambda=0$). The control limits for the transformed data was calculated by Minitab using the mean+/−3 standard deviations. Standard deviation is determined based on the average moving range. A moving range of 100 was selected to account for the variation in column performance over the column life. The upper control limits for the transformed data were reverse transformed to give 0.110 for the equilibration front, 0.027 for the WFI flush front, and 0.073 for the storage front (see Table 3). Results within the limits will ensure that the model fits the data as well as historical results. If the result is outside of this range, a special cause is likely.

Mean:

The mean was added as a second measure of the accuracy of the gamma distribution model. The mean represents the theoretical center of mass for the front and should always be near 1 column volume unless there are other factors in the system that cause it to shift, such as large extra column volume or interaction between the mobile phase and resin. The mean values for equilibration, WFI flush and storage fronts have an irregular distribution and do not benefit from transformation. It is recommended to apply control limits of 0.80 to 1.20 CV for the mean for each of the fronts (see Table 3). This is appropriate because the mean is not a measure of the column performance but is used as a check to ensure that the analysis was appropriate. These limits are expected to be sufficient to identify significant departures from the expected calculation results. Tighter control limits would result in unnecessary sensitivity for this check, which is seen to vary with each column pack.

TABLE 3

Recommended HETP, SS, and Mean Control Limits for SPHP Column Purification during REMICADE ® (infliximab) Manufacturing

| Front | Parameter | UCL | LCL |
|---|---|---|---|
| Equilibration | HETP | 0.081 | 0.018 |
| | SS | 0.110 | NA |
| | Mean | 1.20 | 0.80 |
| WFI Flush | HETP | 0.066 | 0.015 |
| | SS | 0.027 | NA |
| | Mean | 1.20 | 0.80 |
| Wash | HETP | 0.056 | 0.020 |
| | SS | 0.073 | NA |
| | Mean | 1.20 | 0.80 |

Example 4—Application of the Gamma Distribution Transition Analysis for Column Qualification of Q2 Chromatography Columns Used in to REMICADE® (Infliximab) Manufacturing Overview:

This Example describes the application of the GDTA method to the Secondary Anion Exchange (Q2) column purification step employed REMICADE® (infliximab) manufacturing. The Q2 column is an anion exchange chromatography column. The purification process includes three transition fronts, i.e., equilibration, strip, and storage fronts, which are appropriate for GDTA as described herein.

The GDTA was executed on 68 fronts, comprising 23 equilibration and strip fronts, and 22 storage fronts. The gamma front distribution analysis was performed concurrently with manufacturing and did not impact the manufacturing process. All manufacturing, monitoring and controls were performed using current, effective procedures. During the column chromatography purification of REMICADE® (infliximab), conductivity (i.e., the column outlet signal) and flow of the eluent (i.e., accumulated flow) were recorded.

In addition to the application of the GDTA to column operation in real time, historical data for 324 transition fronts processed over the course of the four previous years was also collected and analyzed as described herein. The data set included 121 equilibration fronts, 124 strip fronts, and 79 storage fronts. This data set was selected to provide an even distribution through the life of the columns and represents 10 column packs.

The GDTA for the Q2 column fronts was carried out as described in Example 1 above. This analysis produced measurements for HETP, SS and mean for each front. Control limits that were derived for each of these three parameters based on statistical evaluation listed in Table 4 below.

Control Limits for Q2 Column:
HETP:

HETP is directly related to the column performance and is also affected by other factors in the system that may increase dispersion. The result must be >0. The control limits for HETP are best determined by using the natural log Box-Cox transformation ($\lambda=0$). The control limits for the transformed data were calculated by Minitab using the mean+/−3 standard deviations. Standard deviation is determined based on the average moving range. A moving range of 100 was selected to account for the variation in column performance over the column life. The upper and lower control limits are reverse transformed ($e^x$) to determine the control limits for the untransformed data.

Figure 36:
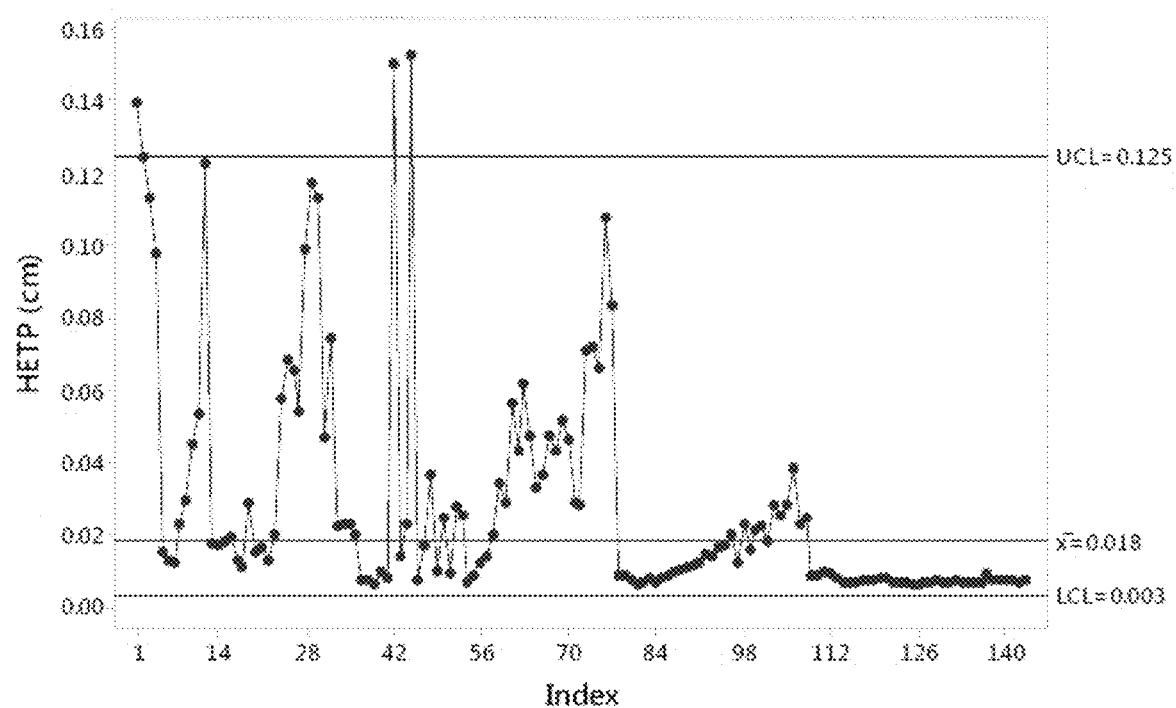
FIG. 36 is a time series plot of HETP for Q2 column equilibration front. Control limits are derived from the natural log Box-Cox transformation data.
Figure 37:
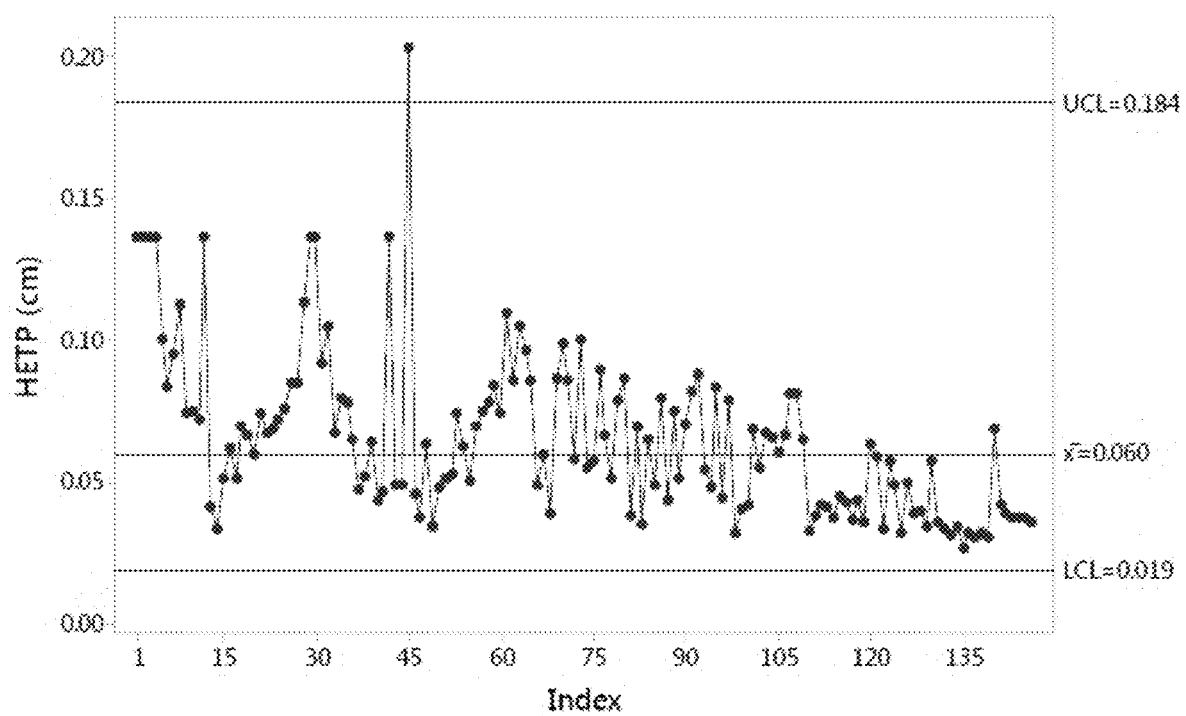
FIG. 37 is a time series plot of HETP for Q2 column strip equilibration front. Control limits are derived from the natural log Box-Cox transformation data.
Figure 38:
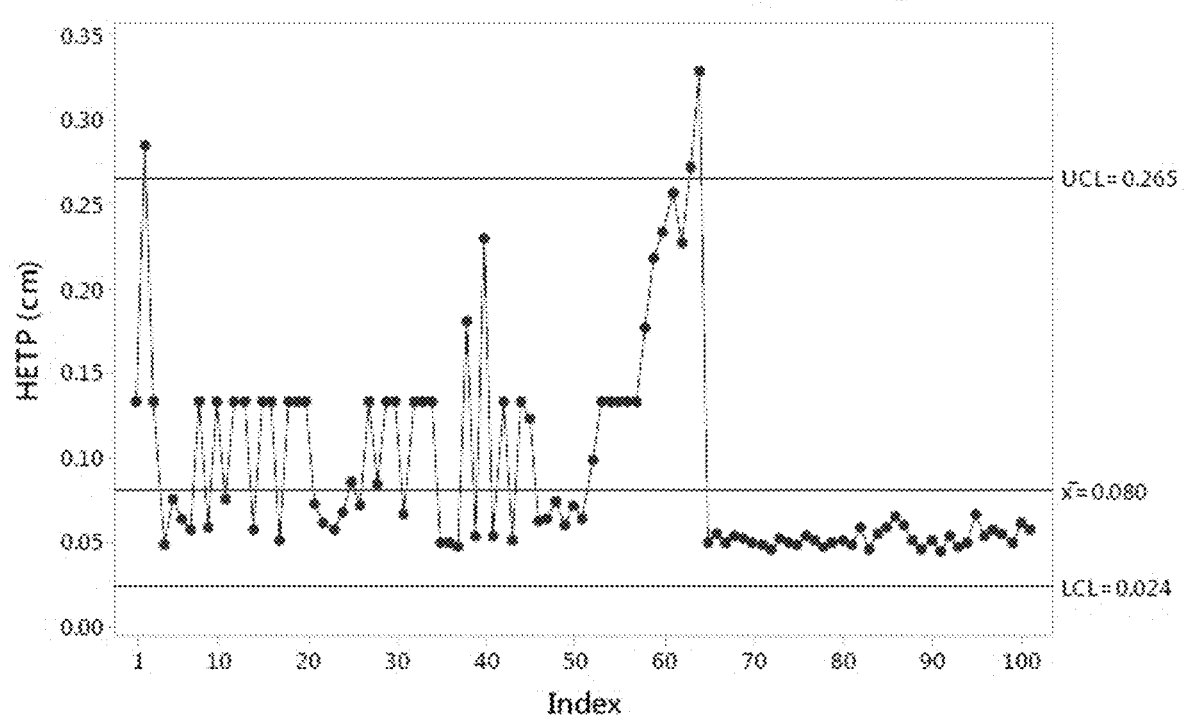
FIG. 38 is a time series plot of HETP for Q2 column storage front. Control limits are derived from the natural log Box-Cox transformation data.

A time series plot for each front's HETP results and control limits is shown in FIG. 36 (equilibration front), FIG. 37 (strip front), and FIG. 38 (storage front). Operation within these limits is expected to produce acceptable chromatographic performance based on this historical review. Values above the upper control limits may indicate column flow issues and should be evaluated further. Values below the lower control limits may be indicative of a calculation error.

Sum of Squares (SS):

The SS is a measure of how well the gamma distribution model fits the data. This measure will be used to ensure that HETP values calculated using the GDTA method represent the process data. There is no lower limit and the result must be >0. The upper control limit for SS is best determined by using the natural log Box-Cox transformation ($\lambda=0$). The control limits for the transformed data were calculated by Minitab using the mean+/−3 standard deviations. Standard deviation is determined based on the average moving range. A moving range of 100 was selected to account for the variation in column performance over the column life. The standard deviation was determined from the aggregate data for the Storage front, as the moving range method produced a higher standard deviation. The control limits are reported in Table 4 below. Results within the limits will ensure that the model fits the data as well as historical results. If the result is outside of this range, a special cause is likely.

Mean:

The mean was added as a second measure of the accuracy of the gamma distribution model. The mean represents the theoretical center of mass for the front and should always be near 1 column volume unless there are other factors in the system that cause it to shift, such as large extra column volume or interaction between the mobile phase and resin. The mean values for equilibration, strip, and storage fronts have an irregular distribution and do not benefit from transformation. It is recommended to apply control limits of 0.80 to 1.20 CV for the mean for each of the fronts (see Table 4). This is appropriate because the mean is not a measure of the column performance but is used as a check to ensure that the analysis was appropriate. These limits are expected to be sufficient to identify significant departures from the expected calculation results. Tighter control limits would result in unnecessary sensitivity for this check, which is seen to vary with each column pack.

TABLE 4

Recommended HETP, SS, and Mean Control Limits for Q2 Column Purification during REMICADE ® (infliximab) Manufacturing

| Front | Parameter | UCL | LCL |
|---|---|---|---|
| Equilibration | HETP | 0.125 | 0.003 |
| | SS | 0.344 | NA |
| | Mean | 1.20 | 0.80 |
| Strip | HETP | 0.184 | 0.019 |
| | SS | 0.156 | NA |
| | Mean | 1.20 | 0.80 |
| Wash | HETP | 0.265 | 0.024 |
| | SS | 0.691 | NA |
| | Mean | 1.20 | 0.80 |

Example 5—Manufacturing Processes to Produce SIMPONI® (Golimumab)

Background for Golimumab

Therapies with anti-TNFα agents have been used successfully in the treatment of inflammatory arthritides, but the early anti-TNFα agents had limitations with respect to safety, dosing regimen, cost, and/or immunogenicity. To address some of the limitations, a fully human anti-TNFα mAb was developed, designated SIMPONI® (golimumab). Golimumab (also known as CNTO 148 and rTNV148B) is a fully human monoclonal antibody with an Immunoglobulin G 1 (IgG1) heavy chain isotype (G1m[z] allotype) and a kappa light chain isotype. Golimumab has a heavy chain (HC) comprising amino acid sequence of SEQ ID NO:1 and a light chain (LC) comprising amino acid sequence of SEQ ID NO:2. The molecular weight of golimumab ranges from 149,802 to 151,064 Daltons.

Golimumab forms high affinity, stable complexes with both the soluble and transmembrane bioactive forms of human tumor necrosis factor alpha (TNFα) with high affinity and specificity which prevents the binding of TNFα to its receptors and neutralizes TNFα bioactivity. No binding to other TNFα superfamily ligands was observed; in particular, golimumab does not bind or neutralize human lymphotoxin. TNFα is synthesized primarily by activated monocytes, macrophages and T cells as a transmembrane protein that self-associates to form a bioactive homotrimer that is rapidly released from the cell surface by proteolysis. The binding of TNFα to either the p55 or p75 TNF receptors leads to clustering of the receptor cytoplasmic domains and initiates signaling. Tumor necrosis factor α has been identified as a key sentinel cytokine that is produced in response to various stimuli and subsequently promotes the inflammatory response through activation of the caspase-dependent apoptosis pathway and the transcription factors nuclear factor (NF)-κB and activator protein-1 (AP-1). Tumor necrosis factor α also modulates the immune response through its role in the organization of immune cells in germinal centers. Elevated expression of TNFα has been linked to chronic inflammatory diseases such as rheumatoid arthritis (RA), as well as spondyloarthropathies such as psoriatic arthritis (PsA) and ankylosing spondylitis (AS) and is an important mediator of the articular inflammation and structural damage that are characteristic of these diseases.

Clinical Trials with Golimumab

In a global, randomized, double-blind, placebo-controlled Phase 3 study of subcutaneously (SC) administered golimumab in subjects with Ankylosing Spondylitis (AS) (Study C0524T09), golimumab was demonstrated to be efficacious in improving the signs and symptoms, physical function, and health-related quality of life (HRQOL) in subjects affected by Ankylosing Spondylitis (AS). Furthermore, safety analyses showed that SC golimumab was generally well tolerated and demonstrated a safety profile similar to that observed with other anti-TNFα agents.

Given the known safety and efficacy of SC golimumab, it was anticipated that IV golimumab would also prove efficacious with an acceptable safety profile consistent with other anti-TNFα agents in rheumatologic diseases such as RA, PsA, and AS. Intravenous golimumab has been definitively studied in a Phase 3 study (CNTO148ART3001) that formed the basis of approval for the treatment of RA. The CNTO148ART3001 study was a randomized, double-blind, placebo-controlled, multicenter, 2-arm study of the efficacy and safety of IV administration of golimumab 2 mg/kg infusions administered over a period of 30±10 minutes at Weeks 0, 4, and every 8 weeks (q8w) thereafter in subjects with active RA despite concurrent methotrexate (MTX) therapy. Subjects with active RA despite MTX were randomized to receive either placebo infusions or IV golimumab administered 2 mg/kg at Weeks 0, 4, and every 8 weeks through Week 24. Starting at Week 24, all subjects were treated with IV golimumab through Week 100. It was demonstrated that IV golimumab provided substantial benefits in improving RA signs and symptoms, physical function, and health related quality of life, as well as inhibiting the progression of structural damage. Golimumab administered intravenously in the treatment of RA (CNTO148ART3001) demonstrated robust efficacy and an acceptable safety profile with a low incidence of infusion reactions.

More recently, two Phase 3 studies were designed to evaluate the efficacy and safety of intravenous (IV) golimumab in the treatment of subjects with active Ankylosing Spondylitis (AS) and active Psoriatric Arthritis (PsA). The IV route of administration in subjects is being evaluated since currently available IV anti-TNFα agents have limitations with respect to immunogenicity and infusion reactions, and have longer infusion times (60 to 120 minutes) compared with the 30±10 minute infusions with IV golimumab. Patients may also prefer the maintenance dosage schedule IV golimumab rather than more frequent administrations compared with SC agents.

Sequences

Example Anti-TNFα Antibody Sequences—SIMPONI® (Golimumab)

Heavy chain CDRs (HCDRs) and light chain CDRs (LCDRs) are underlined in the heavy chain and light chain of golimumab (defined by Kabat).

```
Heavy Chain (HC) - SEQ ID NO: 1
  1   QVQLVESGGG VVQPGRSLRL SCAASGFIFS SYAMHWVRQA

PGNGLEWVAF MSYDGSNKKY

61   ADSVKGRFTI SRDNSKNTLY LQMNSLRAED TAVYYCARDR

GIAAGGNYYY YGMDVWGQGT

121   TVTVSSASTK GPSVFPLAPS SKSTSGGTAA LGCLVKDYFP

EPVTVSWNSG ALTSGVHTFP

181   AVLQSSGLYS LSSVVTVPSS SLGTQTYICN VNHKPSNTKV

DKKVEPKSCD KTHTCPPCPA
```

```
-continued
241  PELLGGPSVF LFPPKPKDTL MISRTPEVTC VVVDVSHEDP

EVKFNWYVDG VEVHNAKTKP

301  REEQYNSTYR VVSVLTVLHQ DWLNGKEYKC KVSNKALPAP

IEKTISKAKG QPREPQVYTL

361  PPSRDELTKN QVSLTCLVKG FYPSDIAVEW ESNGQPENNY

KTTPPVLDSD GSFFLYSKLT

421  VDKSRWQQGN VFSCSVMHEA LHNHYTQKSL SLSPGK 456

Light chain (LC) - SEQ ID NO: 2
  1  EIVLTQSPAT LSLSPGERAT LSCRASQSVY SYLAWYQQKP

GQAPRLLIYD ASNRATGIPA

61  RFSGSGSGTD FTLTISSLEP EDFAVYYCQQ RSNWPPFTFG

PGTKVDIKRT VAAPSVFIFP

121  PSDEQLKSGT ASVVCLLNNF YPREAKVQWK VDNALQSGNS

QESVTEQDSK DSTYSLSSTL

181  TLSKADYEKH KVYACEVTHQ GLSSPVTKSF NRGEC
```

Recombinant Expression Cassettes

The present invention uses recombinant expression cassettes comprising a nucleic acid. A nucleic acid sequence, for example, a cDNA or a genomic sequence encoding an antibody used in the method of the present invention, can be used to construct a recombinant expression cassette that can be introduced into at least one desired host cell. A recombinant expression cassette will typically comprise a polynucleotide operably linked to transcriptional initiation regulatory sequences that will direct the transcription of the polynucleotide in the intended host cell. Both heterologous and non-heterologous (i.e., endogenous) promoters can be employed to direct expression of the nucleic acids.

In some embodiments, isolated nucleic acids that serve as promoter, enhancer, or other elements can be introduced in the appropriate position (upstream, downstream or in the intron) of a non-heterologous form of a polynucleotide of the present invention so as to up or down regulate expression of a polynucleotide. For example, endogenous promoters can be altered in vivo or in vitro by mutation, deletion and/or substitution.

Vectors and Host Cells

The present invention also relates to vectors that include isolated nucleic acid molecules, host cells that are genetically engineered with the recombinant vectors, and the production of at least one anti-TNFα antibody by recombinant techniques, as is well known in the art.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but are not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS) (U.S. Pat. Nos. 5,122,464; 5,770,359; 5,827,739) resistance for eukaryotic cell culture, and tetracycline or ampicillin resistance genes for culturing in E. coli and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be affected by calcium phosphate transfection, DEAE-dextran mediated transfection, cationic lipid-mediated transfection, electroporation, transduction, infection or other known methods. Such methods are well-known and well-described in the art.

At least one antibody used in the method of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. Such methods are described in many standard laboratory manuals, and the methods are well-known and well-described in the art.

Those of ordinary skill in the art are knowledgeable in the numerous expression systems available for expression of a nucleic acid encoding a protein used in the method of the present invention. Alternatively, nucleic acids can be expressed in a host cell by turning on (by manipulation) in a host cell that contains endogenous DNA encoding an antibody. Such methods are well known in the art, e.g., as described in U.S. Pat. Nos. 5,580,734, 5,641,670, 5,733,746, and 5,733,761.

Cells useful for the production of the antibodies, specified portions or variants thereof, include mammalian cells. Mammalian cell systems often will be cultured in the form of monolayers of cells, but the cells can also be adapted to grow in suspension, e.g., in shake flasks or bioreactors. A number of suitable host cell lines capable of expressing intact glycosylated proteins have been developed in the art, and include, e.g., COS-1 (e.g., ATCC® CRL1650), COS-7 (e.g., ATCC® CRL-1651), HEK293, BHK21 (e.g., ATCC® CCL-10), BSC-1 (e.g., ATCC® CCL-26), Hep G2, P3X63Ag8.653, Sp2/0-Ag14, HeLa and the like, which are readily available from, for example, American Type Culture Collection, Manassas, Va. (www.atcc.org). In certain embodiments, host cells include CHO cells and cells of lymphoid origin, such as myeloma and lymphoma cells, e.g., CHO-K1 cells, P3X63Ag8.653 cells (ATCC® CRL-1580) and Sp2/0-Ag14 cells (ATCC® CRL-1581).

Expression vectors for these cells can include one or more of the following expression control sequences, such as, but not limited to, an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., "Expression of a recombinant DNA gene coding for the vesicular stomatitis virus nucleocapsid protein." *J. Virol.* 45:773-781 (1983)). Additionally, gene sequences to control replication in the host cell can be incorporated into the vector, as known in the art.

CHO Cell Lines

Despite the availability of several other mammalian cell lines, a majority of recombinant therapeutic proteins produced today are made in Chinese hamster ovary (CHO) cells (Jayapal K P, et al. "Recombinant protein theo rapeutics from CHO cells-20 years and counting." Chem Eng Prog. 2007; 103:40-47; Kunert R, Reinhart D. "Advances in recombinant antibody manufacturing." *Appl Microbiol Biotechnol.* 2016; 100(8):3451-61). Their strengths include, e.g., robust growth as adherent cells or in suspension, adaptability to serum-free and chemically defined media, high productivity, and an established history of regulatory approval for therapeutic recombinant protein production. They are also very amenable to genetic modifications and the methods for cell transfection, recombinant protein expression, and clone selection are all well characterized. CHO cells can also provide human-compatible post-translational modifications. As used herein, "CHO cells" include, but are not limited to, e.g., CHO-DG44, CHO-K1, CHO-M, CHO-S, CHO GS knockout, and modifications and derivatives thereof.

Cloning and Expression in CHO Cells.

One vector commonly used for expression in CHO cells is pC4. Plasmid pC4 is a derivative of the plasmid pSV2-dhfr (ATCC® 37146). The plasmid contains the mouse DHFR gene under control of the SV40 early promoter. Chinese hamster ovary cells or other cells lacking dihydrofolate activity that are transfected with these plasmids can be selected by growing the cells in a selective medium (e.g., alpha minus MEM, Life Technologies, Gaithersburg, Md.) supplemented with the chemotherapeutic agent methotrexate. The amplification of the DHFR genes in cells resistant to methotrexate (MTX) has been well documented (see, e.g., F. W. Alt, et al., "Selective multiplication of dihydrofolate reductase genes in methotrexate-resistant variants of cultured murine cells." *J. Biol. Chem.* 253:1357-1370 (1978); and M. J. Page and M. A. Sydenham, "High level expression of the humanized monoclonal antibody Campath-1H in Chinese hamster ovary cells." *Biotechnology* 9:64-68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach can be used to develop cell lines carrying more than 1,000 copies of the amplified gene(s). Subsequently, when the methotrexate is withdrawn, cell lines are obtained that contain the amplified gene integrated into one or more chromosome(s) of the host cell.

Plasmid pC4 contains for expressing the gene of interest the strong promoter of the long terminal repeat (LTR) of the Rous Sarcoma Virus (Cullen, et al., "Functional analysis of the transcription control region located within the avian retroviral long terminal repeat." *Molec. Cell. Biol.* 5:438-447 (1985)) plus a fragment isolated from the enhancer of the immediate early gene of human cytomegalovirus (CMV) (Boshart, et al., "A very strong enhancer is located upstream of an immediate early gene of human cytomegalovirus." *Cell* 41:521-530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human beta-actin promoter, the SV40 early or late promoters or the long terminal repeats from other retroviruses, e.g., HIV and HTLVI. Clontech's Tet-Off and Tet-On gene expression systems and similar systems can also be used to express proteins in a regulated way in mammalian cells (M. Gossen, and H. Bujard, "Tight control of gene expression in mammalian cells by tetracycline-responsive promoters." *Proc. Natl. Acad. Sci. USA* 89: 5547-5551 (1992)). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

General Purification Methods

An anti-TNFα antibody can be recovered and purified from recombinant cell cultures by well-known methods including, but not limited to, e.g., protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification.

As used herein, the terms "antibody" or "antibodies", include biosimilar antibody molecules approved under the Biologics Price Competition and Innovation Act of 2009 (BPCI Act) and similar laws and regulations globally. Under the BPCI Act, an antibody may be demonstrated to be biosimilar if data show that it is "highly similar" to the reference product notwithstanding minor differences in clinically inactive components and are "expected" to produce the same clinical result as the reference product in terms of safety, purity and potency (R. Dolinar, F. Lavernia, and S. Edelman. "A GUIDE TO FOLLOW-ON BIOLOGICS AND BIOSIMILARS WITH A FOCUS ON INSULIN." *Endocrine Practice*: February 2018, Vol. 24, No. 2, pp. 195-204). These biosimilar antibody molecules are provided an abbreviated approval pathway, whereby the applicant relies upon the innovator reference product's clinical data to secure regulatory approval. Compared to the original innovator reference antibody that was FDA approved based on successful clinical trials, a biosimilar antibody molecule is referred to herein as a "follow-on biologic". As presented herein, SIMPONI® (golimumab) is the original innovator reference anti-TNFα antibody that was FDA approved based on successful clinical trials. Golimumab has been on sale in the United States since 2009.

As used herein, the term "antigen-binding fragment" refers to an antibody fragment such as, for example, a diabody, a Fab, a Fab', a F(ab')2, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), a single domain antibody (sdab) an scFv dimer (bivalent diabody), a multi-specific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment binds. According to particular embodiments, the antigen-binding fragment comprises a light chain variable region, a light chain constant region, and an Fd segment (i.e., portion of the heavy chain which is included in the Fab fragment). According to other particular embodiments, the antigen-binding fragment comprises Fab and F(ab').

Manufacturing Process Overview

Figure 39:
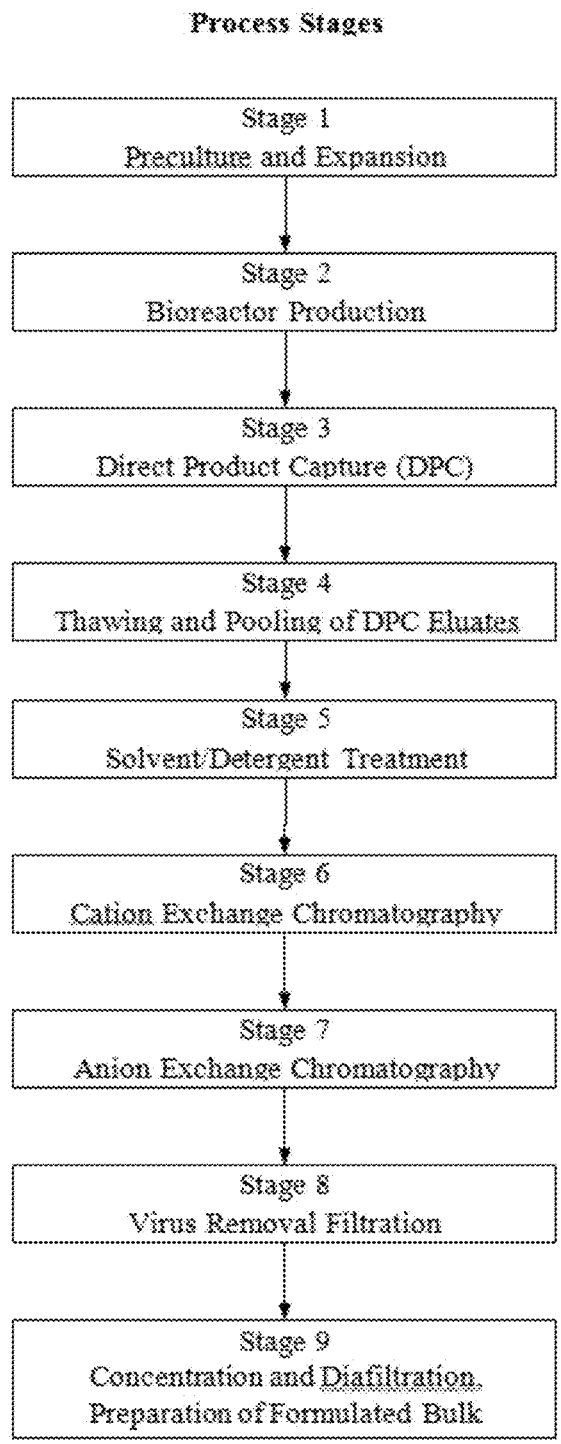
FIG. 39 shows an overview of the 9 stages of the golimumab manufacturing process.

SIMPONI® (golimumab) is manufactured in a 9-stage process that includes continuous perfusion cell culture followed by purification. An overview of the manufacturing process is provided in FIG. 39.

As used herein, the terms "culture", "culturing", "cultured", and "cell culture" refer to a cell population that is suspended in a medium under conditions suitable to survival and/or growth of the cell population. As will be clear from context to those of ordinary skill in the art, these terms as used herein also refer to the combination comprising the cell population and the medium in which the population is suspended. Cell culture includes, e.g., cells grown by batch, fed-batch or perfusion cell culture methods and the like. In certain embodiments, the cell culture is a mammalian cell culture.

Cell lines for use in the present invention include mammalian cell lines including, but not limited to, Chinese Hamster Ovary cells (CHO cells), human embryonic kidney cells (HEK cells), baby hamster kidney cells (BHK cells), mouse myeloma cells (e.g., NS0 cells and Sp2/0 cells), and human retinal cells (e.g., PER.C6 cells).

As used herein, the terms "chemically defined medium", "chemically defined media", "chemically defined hybridoma medium", or "chemically defined hybridoma media" refer to a synthetic growth medium in which the identity and concentration of all the components are known. Chemically defined media do not contain bacterial, yeast, animal, or plant extracts, animal serum or plasma although they may or may not include individual plant or animal-derived components (e.g., proteins, polypeptides, etc). Chemically defined media may contain inorganic salts such as phosphates, sulfates, and the like needed to support growth. The carbon source is defined, and is usually a sugar such as glucose, lactose, galactose, and the like, or other compounds such as glycerol, lactate, acetate, and the like. While certain chemically defined media also use phosphate salts as a buffer, other buffers may be employed such as citrate, triethanolamine, and the like. Examples of commercially available chemically defined media include, but are not limited to, ThermoFisher's CD Hybridoma Medium and CD Hybridoma AGT™ Medium, various Dulbecco's Modified Eagle's (DME) mediums (Sigma-Aldrich Co; SAFC Biosciences, Inc), Ham's Nutrient Mixture (Sigma-Aldrich Co; SAFC Biosciences, Inc), combinations thereof, and the like. Methods of preparing chemically defined mediums are known in the art, for example in U.S. Pat. Nos. 6,171,825 and 6,936,441, WO 2007/077217, and U.S. Patent Application Publication Nos. 2008/0009040 and 2007/0212770.

The term "bioreactor" as used herein refers to any vessel useful for the growth of a cell culture. The bioreactor can be of any size so long as it is useful for the culturing of cells. In certain embodiments, such cells are mammalian cells. Typically, the bioreactor will be at least 1 liter and may be 10, 100, 250, 500, 1,000, 2,500, 5,000, 8,000, 10,000, 12,000 liters or more, or any volume in between. The internal conditions of the bioreactor, including, but not limited to pH and temperature, are optionally controlled during the culturing period. The bioreactor can be composed of any material that is suitable for holding mammalian cell cultures suspended in media under the culture conditions of the present invention, including glass, plastic or metal. The term "production bioreactor" as used herein refers to the final bioreactor used in the production of the polypeptide or glycoprotein of interest. The volume of the production bioreactor is typically at least 500 liters and may be 1,000, 2,500, 5,000, 8,000, 10,000, 12,000 liters or more, or any volume in between. One of ordinary skill in the art will be aware of and will be able to choose suitable bioreactors for use in practicing the present invention.

Preculture, cell expansion, and cell production are performed in Stages 1 and 2. In Stage 1, preculture is initiated from a single working cell bank vial of transfected Sp2/0 cells expressing the HC and LC sequences of golimumab and the cells are expanded in culture flasks, disposable culture bags, and either a 50-L perfusion seed bioreactor equipped with an internal spin filter or a 200-L perfusion seed bioreactor equipped with an alternating tangential flow hollow-fiber filter (ATF) cell retention system. The cells are cultured until the cell density and volume required for inoculation of a 500-L or a 1000-L production bioreactor are obtained. In Stage 2, the cell culture is continuously perfused in a 500-L or a 1000-L production bioreactor using an ATF system. Cell culture permeate (harvest) is collected from the ATF system while cells are returned to the bioreactor, and the culture is replenished with fresh medium. Biomass removed from the bioreactor may be combined with harvest withdrawn from the ATF system and then may be clarified to create a pooled harvest for further processing.

Purification of golimumab from the cell culture harvest is performed in Stages 3 through 8 by a combination of affinity and ion exchange chromatography steps and steps to inactivate or remove potential virus contamination (solvent/detergent treatment and virus removal filtration). In Stage 3, harvest and/or pooled harvest is clarified and purified using Protein A affinity chromatography. The resultant direct product capture (DPC) eluate is frozen until further processing. DPC eluates are filtered and pooled in Stage 4 following thaw, and subsequently treated in Stage 5 with tri-n-butyl phosphate (TNBP) and polysorbate 80 (PS 80) to inactivate any lipid-enveloped viruses potentially present.

In Stage 6, TNBP and PS 80 reagents and impurities are removed from the golimumab product using cation exchange chromatography. The golimumab product is further purified using anion exchange chromatography in Stage 7 to remove DNA, potentially present viruses, and impurities. In Stage 8, the purified golimumab product is diluted and filtered through a virus retentive filter.

Final preparation of golimumab is performed in Stage 9. The ultrafiltration step concentrates the golimumab product, and the diafiltration step adds the formulation excipients and removes the in-process buffer salts. PS 80 is added, and the bulk intermediate is filtered into polycarbonate containers for frozen storage as formulated bulk.

A batch is defined a s a quantity of material, intermediate, or finished product that is intended to be uniform in character and quality, and which has been produced during a defined cycle of manufacture. The term "batch" is applied to:

Preculture
50-L seed reactor/500-L production bioreactor
200-L seed bioreactor
1000-L production bioreactor
Direct product capture
Downstream processing During multiple stages of the manufacturing process, various batch numbers are assigned. Below a summary is given of the stages of the manufacturing process that are defined as a batch.

The first stage in the manufacturing process is the initiation of a preculture from a working cell bank (WCB) vial. Each preculture or backup preculture is identified as a batch.

When the preculture meets inoculation criteria, the preculture is transferred to a 50-L seed bioreactor and the contents of one 50-L seed bioreactor are transferred to one 500-L production bioreactor, each combination of 50-L and 500-L bioreactor is identified as a batch. Biomass removed from the bioreactor may be combined with harvest withdrawn from the ATF system and then may be clarified to create a pooled harvest for further processing. All cell culture supernatant harvest or pooled harvest derived from one 500-L bioreactor receives the bioreactor batch number plus an extension corresponding with a specific harvest (i.e., 001, 002, etc.).

The preculture may also be transferred to a 200-L seed bioreactor and the contents of one 200-L seed bioreactor are transferred to one 1000-L production bioreactor. Each individual 200-L and 1000-L bioreactor is defined as a batch. All cell culture supernatant harvest derived from one 1000-L bioreactor receives the bioreactor batch number plus an extension corresponding with a specific harvest (i.e., 001, 002, etc.).

Pooling of cell culture supernatant harvest from multiple bioreactors is allowed for purification in the Direct Product Capture (DPC) Protein A chromatography step. Each DPC run is identified as a batch. A 28, 40, 60, or 80-cm diameter column may be used for DPC. Each batch may contain different amounts of golimumab starting material and different diameter columns are used based on the amount of golimumab starting material. Multiple DPC batches are pooled to initiate a downstream processing (DSP) batch, which may be initiated with varying amounts of golimumab.

The bulk manufacturing process permits the pooling of any harvest meeting in-process control acceptance criteria for further processing by Protein A chromatography (Stage 3). Similarly, any DPC batch meeting in-process control specifications may be pooled (Stage 4) in order to initiate a downstream batch. However, the mass weighted average age of the cell culture harvest contributing to the DPC pool must be between 15 and 51 days, inclusive.

The mass weighted average age of a DPC pool is defined as the sum of the golimumab mass contributed by each harvest multiplied by the harvest day number, divided by the total golimumab mass of the DPC pool:

$$\text{Mass Weighted Average} = \frac{(m_1 d_1 + m_2 d_2 + m_3 d_3 + \ldots m_i d_i)}{(m_1 + m_2 + \ldots m_i)}$$

Where, m is the golimumab mass contributed to the pool by each harvest and d is the bioreactor day when the collection of the harvest lot is completed.

Process variables, including both inputs (i.e., process parameters) and outputs (i.e., in-process controls [IPCs] and process monitoring tests [PMTs]) are controlled throughout the manufacturing process and documented in production batch records to ensure both process and product consistency.

Detailed Description of Manufacturing Process and Process Controls

Stage 1
Preculture and Expansion

The first stage in the production of SIMPONI® (golimumab) is the initiation of preculture from a Working Cell Bank (WCB) vial of transfected Sp2/0 cells expressing the HC and LC sequences of golimumab and subsequent expansion of the cell culture in culture flasks, disposable culture bags, and 50- or 200-L seed bioreactor. The cells are cultured until the cell density and volume required for inoculation of the 500- or 1000-L production bioreactor are obtained.

Manufacturing Procedure

A cryovial from the WCB is thawed and diluted with chemically defined Hybridoma medium supplemented with 6 mM L-glutamine, 0.5 mg/L mycophenolic acid, 2.5 mg/L hypoxanthine, and 50 mg/L xanthine (CDH-A medium) to a seeding density of 0.2-0.4×10$^6$ viable cells (VC)/mL. Culture viability at thaw must be 50%. The initial passage is maintained in culture flask(s) in a humidified $CO_2$ incubator with temperature and $CO_2$ controlled within ranges defined in the batch record. The culture is incubated for 2-3 days until a minimum cell density of 0.6×10$^6$ VC/mL is obtained.

Scale-up is accomplished by sequentially expanding the culture in culture flasks and disposable culture bags. Each passage is started at a cell density of 0.2-0.4×10$^6$ VC/mL by dilution with CDH-A medium. Passages are incubated for 2-3 days at each expansion step until a minimum cell density of 0.6×10$^6$ VC/mL is obtained. Once sufficient culture volume is achieved in a disposable culture bag at ≥0.8×10$^6$ VC/mL and ≥80% culture viability, the culture may be inoculated into the 50- or 200-L seed bioreactor.

Each preculture passage is sampled for viable cell density (VCD), culture viability, and microscopic examination. Prior to inoculation of the 50- or 200-L seed bioreactor, the preculture is sampled for bioburden. Preculture may be maintained for a maximum of 30 days post-thaw. Preculture is terminated if microbial contamination is detected or the maximum duration is exceeded. A back-up preculture may be retained upon inoculation of the seed bioreactor or may be started with a new WCB vial thaw. The back-up preculture is expanded as described above and is subject to the same in-process controls and operating parameters as the primary cultures. A back-up preculture may be maintained and used to inoculate a 50- or 200-L seed bioreactor as needed.

When the preculture meets inoculation criteria, the contents of the disposable culture bag(s) are transferred to the 50- or 200-L seed bioreactor to achieve a seeding density of ≥0.3×10$^6$ VC/mL. The 50- or 200-L seed bioreactor is fed with CDH-A culture medium and, at full working volume, is operated in perfusion mode. The culture is controlled for pH, temperature, and dissolved oxygen concentration to support cell growth. The 50- or 200-L seed bioreactor culture is expanded until a cell density of ≥2.0×10$^6$ VC/mL, at ≥80% culture viability, is obtained. The 50- or 200-L seed bioreactor culture is sampled throughout the process for VCD, culture viability, and microscopic examination. Prior to inoculation of the 500- or 1000-L production bioreactor, the 50- or 200-L seed bioreactor is sampled for bioburden. If the VCD of the 50- or 200-L seed bioreactor reaches ≥2.0×10$^6$ VC/mL and the 500- or 1000-L production bioreactor is not ready for inoculation, the culture may be continued in perfusion mode up to the maximum culture duration of 6 days post inoculation of the 50-L seed bioreactor and 7 days post inoculation of the 200-L seed bioreactor. The 50- or 200-L seed bioreactor operation is terminated if microbial contamination is detected or the maximum duration is exceeded.

Stage 2
Bioreactor Production

The second stage in the manufacturing process is perfusion cell culture in a 500- or 1000-L production bioreactor. Cell culture permeate (harvest) is collected from the production bioreactor while cells are retained via an alternating tangential flow (ATF) hollow fiber cell-retention device, and the culture is replenished with fresh media.

Manufacturing Procedure

The inoculation of the 500-L or 1000-L production bioreactor is performed by transferring the contents of the 50- or 200-L seed bioreactor into the 500- or 1000-L production bioreactor containing chemically defined Hybridoma medium supplemented with 6 mM L-glutamine, 0.5 mg/L mycophenolic acid, 2.5 mg/L hypoxanthine, and 50 mg/L xanthine (CDH-A medium). The volume transferred must be sufficient to yield a seeding density of ≥0.3×10$^6$ viable cells (VC)/mL. The cultures are maintained at a temperature of 34.0-38.0° C., a pH of 6.80-7.40, and dissolved oxygen concentration of 10-80%. Sampling is performed throughout the 500- or 1000-L production process for viable cell density (VCD), culture viability, bioburden, and immunoglobulin G (IgG) concentration.

After inoculation, the medium feed rate to the culture is increased according to a predetermined schedule until the maximum feed rate is reached. The maximum feed rate is controlled to 0.80-1.50 reactor volumes per day. When the full working volume of the bioreactor is reached, perfusion is initiated using the ATF system to separate cells from the permeate. Permeate is continuously withdrawn through the ATF filter, while cell culture is cycled between the ATF system and the bioreactor. The ATF permeate is collected in bioprocess containers (BPCs).

The medium feed to the bioreactor is switched from CDH-A to CD Hybridoma medium supplemented with 6 mM L-glutamine, 0.5 mg/L mycophenolic acid, 2.5 mg/L hypoxanthine, 50 mg/L xanthine, and 10 mM sodium acetate (CDH-B medium) when the VCD reaches ≥0.5×10$^6$ VC/mL, but no later than Day 15 post inoculation of the 500- or 1000-L production bioreactor. The viable cell density in the bioreactor is controlled to a target of at least 12.0×10$^6$ VC/mL by means of a variable biomass removal flow from the culture.

Biomass removed from the bioreactor may be discarded or combined with the ATF permeate and clarified by filtration.

The ATF permeate is designated as the harvest stream. Ethylenediaminetetraacetic acid (EDTA) is added to the harvest stream to a concentration of 5-20 mM. The harvest is stored in bioprocess containers (BPCs) in a 2-8° C. environment for a maximum period of 21 days after disconnection from the bioreactor. Each harvest BPC is sampled for IgG concentration, endotoxin, and bioburden prior to direct product capture (Stage 3).

Perfusion cell culture operation in the 500- or 1000-L production bioreactor continues for up to 60 days post inoculation. On the final day of the 500- or 1000-L production bioreactor operation, the culture is sampled for mycoplasma and adventitious virus testing. The bioreactor IgG concentration is monitored and reported for information only.

Stage 3
Direct Product Capture (DPC)

In Stage 3, harvest from one or more 500- or 1000-L production bioreactors is filtered and purified using a MabSelect™ (GE Healthcare Bio-Sciences, Pittsburgh, Pa., USA) Protein A affinity chromatography column and an automated chromatography skid. The golimumab product is captured from the harvest, and process related impurities, including media components and host-cell related impurities (e.g., DNA and host cell protein), and potentially present viruses are removed. The resultant direct product capture (DPC) eluate is frozen until further processing.

Protein A Column Preparation and Regeneration

Prior to harvest load, the MabSelect™ Protein A column is equilibrated with 50 mM sodium phosphate, 150 mM sodium chloride, 0.1% polysorbate 80 (PS 80), pH 7.3 (equilibration buffer). The column effluent is monitored for pH and conductivity to ensure the column is equilibrated.

After use, the MabSelect™ Protein A column may be regenerated by applying 6 M guanidine HCl followed by a rinse with 0.1 M sodium citrate, pH 3.5 followed by a wash in equilibration buffer. An alternate regeneration procedure that may also be used includes applying equilibration buffer followed by 6 M guanidine HCl, followed by equilibration buffer, followed by 0.1 M sodium citrate, pH 3.5, followed by equilibration buffer. The MabSelect™ resin is stored in 20% ethanol if required.

Manufacturing Procedure

The harvest is passed through a 0.45-μm filter and loaded onto the Protein A column at a load ratio of 20-50 g/L. After washing the column with equilibration buffer until the ultraviolet absorbance at 280 nm ($A_{280}$) returns to ≤100 mAU/mm path length, the column with the bound golimumab product is washed with an additional 2-6 column volumes (CV) of equilibration buffer. Thereafter, an intermediate wash with 4.5-7.0 CVs of 0.1 M sodium citrate, pH 5.0 is performed.

The golimumab product is eluted using 0.1 M sodium citrate, pH 3.5, buffer. The collection of eluted product starts at an ascending $A_{280}$-signal of ≥50 mAU/mm path length and stops at a descending $A_{280}$-signal of ≥50 mAU/mm path length. The flow rate applied during loading, washing and elution is 150-500 cm/h.

Following collection, the golimumab DPC eluate is neutralized to a pH of 6.0-6.5 by addition of 1.0 M Tris buffer (untitrated) and, if needed, 1.0 M citric acid (untitrated). During the pH adjustment, the DPC eluate is mixed to ensure homogeneity of the solution. The pH adjusted golimumab DPC eluate is sampled for analysis of bioburden prior to 0.2-μm filtration. A second 0.2-μm filtration may be performed in case the integrity test of the 0.2-μm filter used during the first 0.2-μm filtration fails.

The filtered DPC eluate is aliquoted into polycarbonate containers. The filtered DPC eluate is sampled for analysis of monomer content, bioburden, endotoxin, and protein concentration (from which the step yield is calculated, which should be ≥55%). The filtered DPC eluate can be held for a cumulative time of ≤48 hours at 15-25° C. and ≤168 hours at 2-8° C. prior to storage at ≤−40° C.

Stage 4
Thawing and Pooling of Direct Product Capture (DPC) Eluates

In Stage 4, multiple direct product capture (DPC) eluates are thawed, filtered, and pooled prior to solvent/detergent treatment.

Manufacturing Procedure

DPC eluates are selected so that the mass weighted average age of the DPC pool is 15-51 days, inclusive. Frozen DPC eluates are thawed at 15-25° C. Thawing is considered complete when the eluates are visibly free of ice. Thawing must not exceed 120 hours. After thawing, pooling, and mixing, the pH of the pooled DPC eluates is tested and, if needed, adjusted by the addition of either 1.0 M Tris (untitrated) or 1.0 M citric acid (untitrated) to a pH of 5.9-6.5. After the final pH is reached, the pooled DPC eluates are sampled for analysis of bioburden. The protein concentration of the pool is calculated based on the total pool volume and total grams of protein in the pool. The pooled DPC eluates are then 0.2-μm filtered into a mixing vessel. The filtered and pooled DPC eluates can be stored for a cumulative time of hours at 15-25° C. and 168 hours at 2-8° C. prior to further processing in Stage 5.

Stage 5
Solvent/Detergent (S/D) Treatment of DPC Eluates

In Stage 5, the pooled direct product capture (DPC) eluates are incubated with tri-n-butyl phosphate (TNBP) and polysorbate 80 (PS 80) (solvent/detergent [S/D] treatment) to inactivate any lipid-enveloped viruses potentially present.

Manufacturing Procedure

A S/D stock solution containing 2% TNBP/10% PS 80 (w/w) is transferred into the mixing vessel with the pooled DPC eluates until a ratio of 0.08-0.12 (v/v) is achieved. The solution is mixed to ensure homogeneity of the solution and then transferred into the inactivation vessel. After transfer, the virus inactivation is accomplished through incubation for at least 90 minutes at a temperature of 15-25° C. The load of the S/D treated golimumab product onto the cation exchange chromatography column (Stage 6) is completed in ≤20 hours after the addition of S/D-chemicals (Stage 5).

Stage 6
Cation Exchange Chromatography

In Stage 6, the solvent/detergent (S/D) treated Stage 5 material is purified using a UNOsphere S™ (Bio-Rad, Hercules, Calif., USA) cation exchange chromatography column and an automated chromatography skid. Stage 6 is designed to remove S/D process chemicals (tri-n-butyl phosphate [TNBP] and polysorbate 80 [PS 80]) and other impurities from the product.

Chromatography Column Preparation and Regeneration

Prior to loading, the packed column is equilibrated with 30 mM sodium phosphate, pH 6.5 buffer (equilibration buffer). The column effluent is monitored for pH and conductivity to ensure the column is equilibrated.

After use, the UNOsphere S™ cation exchange column is regenerated by washing with 50 mM Tris, 1.0 M NaCl, pH 7.6-8.0 buffer followed by a sanitization using 1.0 M NaOH and, if required, stored in solution (0.1 M NaOH).

Manufacturing Procedure

During loading, the S/D-treated product is diluted in-line with water for injection to achieve a load conductivity of 1.5-4.5 mS/cm. After loading the column to a load ratio of 35-55 g golimumab/L, the column is washed with 1.6-6.7 column volumes (CV) of equilibration buffer and, thereafter, 5.2-9.8 CVs of 50 mM Tris, pH 7.6-8.0 buffer.

The material is then eluted from the cation exchange column using 50 mM Tris, 50 mM NaCl, pH 7.6-8.0 buffer. The collection of eluted product starts at an ascending ultraviolet absorbance at 280 nm ($A_{280}$) of ≥30 mAU/mm path length and stops at a descending $A_{280}$ of ≥75 mAU/mm path length. The flow rate applied during loading, washing, and elution is 45-150 cm/h.

The eluted material is sampled for analysis of bioburden, HCP, residual Protein A, aggregate, and protein concentration. The step yield is calculated from the protein concentration, and must conform to ≥80%. The product is then 0.2-μm filtered prior to further processing in Stage 7.

Alternatively, the eluted material is sampled for bioburden and the product is 0.2-μm filtered and sampled for analysis of HCP, residual Protein A, aggregate, and protein concentration. The step yield is calculated from the protein concentration, and must conform to ≥80%. The material is then further processed in Stage 7.

The Stages 6 through 8 cumulative processing and hold time proven acceptable range (PAR) for golimumab is less than or equal to 115 hours, with a manufacturing operating range (MOR) of 70-90 hours at controlled room temperature (15-25° C.). Cumulative processing and hold time is defined as starting at the end of Stage 6 product elution and ending at the start of Stage 9 product concentration, and includes active processing steps as well as intermediate hold times between stages. No individual stage-specific limit for Stage 6, 7, or 8 has been established given that the material conditions do not change for the 3 stages. Thus, process control is based on the cumulative time across the three stages.

Stage 7
Anion Exchange Chromatography

In Stage 7, the Stage 6 material is purified using a Q Sepharose™ XL (GE Healthcare Bio-Sciences, Pittsburgh, Pa., USA) anion exchange chromatography column and an automated chromatography skid. Golimumab flows through the resin while DNA, other impurities, and viruses (if present) are retained.

Chromatography Column Preparation and Regeneration

Prior to loading, the anion exchange column is equilibrated with 50 mM Tris, 50 mM NaCl, pH 7.6-8.0 (equilibration buffer). The column effluent is monitored for pH and conductivity to ensure the column is equilibrated.

After use, the Q Sepharose™ XL anion exchange chromatography column is regenerated by washing with 50 mM Tris, 1.0 M NaCl, pH 7.6-8.0 buffer followed by a sanitization using 2.0 M NaOH and consecutive rinses with WFI, 3.0 M KCl, and WFI or (at Janssen Biologics BV [JBV] only) followed by a sanitization using 1.0 M NaOH/1.0 M NaCl and a rinse with WFI and, if required, the column is stored in solution (0.1 M NaOH).

Manufacturing Procedure

The material purified by cation exchange chromatography (Stage 6) is loaded onto the anion exchange column at a loading flow rate of 50-250 cm/h and a load ratio of 50-150 g/L. The golimumab flows through the column (non-binding mode) and is collected once the ultraviolet absorbance at 280 nm ($A_{280}$) increases to ≥30 mAU/mm path length. After loading the column is washed with equilibration buffer at a flow rate of 50-250 cm/h. The collection of product flow-through continues until the $A_{280}$ reading returns to ≥80 mAU/mm path length.

The flow-through is sampled for analysis of bioburden and protein concentration. The step yield is calculated from the protein concentration, and must conform to ≥80%. The material is then 0.2-μm filtered prior to further processing in Stage 8.

Alternatively, the flow-through is sampled for analysis of bioburden and the material is then 0.2-μm filtered and sampled for protein concentration. The step yield is calculated from the protein concentration, and must conform to ≥80%. Thereafter, if required for Stage 8 processing, the material is diluted with 50 mM Tris, 50 mM NaCl, pH 7.6-8.0 to a protein concentration of g/L, and mixed prior to further processing in Stage 8.

The Stages 6 through 8 cumulative processing and hold time proven acceptable range (PAR) for golimumab is less than or equal to 115 hours, with a manufacturing operating range (MOR) of 70-90 hours at controlled room temperature (15-25° C.). Cumulative processing and hold time is defined as starting at the end of Stage 6 product elution and ending at the start of Stage 9 product concentration, and includes active processing steps as well as intermediate hold times between stages. No individual stage-specific limit for Stage 6, 7, or 8 has been established, as process control is based on the cumulative time across the three stages.

Stage 8
Virus Removal Filtration

In Stage 8, the Stage 7 material, purified by anion exchange chromatography, is filtered through NFP™ virus retentive filters. This step targets the removal of both small and large viruses potentially present.

NFP™ Filter Preparation

Prior to use, the NFP™ filters are installed into the NFP™ filtration system, flushed with water for injection (WFI), and autoclaved. After autoclaving, the filters are flushed with WFI and then tested for water permeability. The filters are equilibrated with 50 mM Tris, 50 mM NaCl, pH 7.6-8.0 buffer. The filtrate is monitored for pH and conductivity to ensure the NFP™ filters are equilibrated.

After product filtration and buffer rinse, the NFP™ filters are individually integrity tested.

Manufacturing Procedure

If required, prior to product filtration, the product purified by anion exchange chromatography (in Stage 7) is diluted with 50 mM Tris, 50 mM NaCl, pH 7.6-8.0 to a protein concentration of ≤6.5 g/L. After dilution, the product solution is mixed and thereafter filtered through a 0.2-μm filter.

The diluted product is then filtered through the equilibrated NFP™ filters using a pressure of ≤3.1 bars. A membrane loading of ≤725 g/m² is applied. An initial product filtration flux rate can be recorded within 20 minutes after start of product filtration for the process. An initial product filtration flux may be recorded within ≤154 L for 9 filters or ≤171 L for 10 filters after start of product filtration. The flux decay is monitored to ensure the reduction from the initial flux rate (defined as 0% flux decay) does not exceed 74%. In case the flux decay reaches the limit of 74% (defined as flux decay limit), the filter may be isolated and product load to that filter stopped. The isolated filter is put back in-line for the buffer flush step, post-load. During filtration, if the flux decay reaches the limit of 74% (defined as flux decay limit), the filtration can be stopped and buffer flushing is immediately executed.

Once filtration is complete, the system including filters is flushed with 50 mM Tris, 50 mM NaCl, pH 7.6-8.0 buffer for a total of ≤10.1 L/m², using a filtration pressure of ≤3.1 bars. The buffer flush is collected, combined, and mixed with the rest of the NFP™-filtered product and sampled for bioburden and protein concentration. The step yield is calculated from the protein concentration, and must conform to ≥90%. The combined NFP™-filtrate is then filtered through a 0.2-μm filter, prior to further processing in Stage 9.

The diluted material from Stage 7 can be sampled for analysis of bioburden just prior to NFP™ filtration. Once filtration is complete, the system including filters is flushed with 50 mM Tris, 50 mM NaCl, pH 7.6-8.0 buffer for a total of ≤10.1 L/m², using a filtration pressure of bars. The buffer flush is collected, combined, and mixed with the rest of the NFP™-filtered material and sampled for analysis of protein concentration. The step yield is calculated from the protein concentration, and must conform to ≥90%, prior to further processing in Stage 9.

The Stages 6 through 8 cumulative processing and hold time proven acceptable range (PAR) for golimumab is less than or equal to 115 hours, with a manufacturing operating range (MOR) of 70-90 hours at controlled room temperature (15-25° C.). Cumulative processing and hold time is defined as starting at the end of Stage 6 elution and ending at the start of Stage 9 concentration, and includes active processing steps as well as intermediate hold times between stages. No individual stage-specific limit for Stage 6, 7, or 8 has been established, as process control is based on the cumulative time across the three stages.

Stage 9
Concentration and Diafiltration to Obtain Formulated Bulk (FB)

In Stage 9, the Stage 8 material is concentrated and diafiltered to add formulation excipients. Thereafter, polysorbate 80 (PS 80) is added to the concentrated and diafiltered golimumab solution to obtain formulated bulk (FB).

Ultrafiltration System Preparation

Prior to use, the ultrafiltration system including membranes is equilibrated with 50 mM Tris, 50 mM NaCl, pH 7.6-8.0 buffer. The filtrate and retentate are monitored for pH to ensure the membranes are equilibrated.

After use, the ultrafiltration system including membranes is sanitized by flushing with water for injection (WFI) and 1.0 M NaOH. WFI is then flushed through the system, and a normalized water permeability test is performed. If required, the system and membranes are stored in an appropriate solution.

Manufacturing Procedure

The golimumab product purified by virus removal filtration (in Stage 8) is concentrated to 40-90 g/L and diafiltered using 8-12 diafiltration volumes of 10 mM histidine, 4.5% sorbitol, pH 5.3 buffer (diafiltration buffer). After diafiltration, the filtrate pH, conductivity, and osmolality are tested to ensure the buffer exchange is performed completely. After buffer exchange, the solution is over-concentrated to ≤180 g/L and then recovered by emptying the system. During concentration, diafiltration, and over-concentration, the feed and the retentate pressure can be controlled to be ≤2.8 bar and ≤2.1 bar, respectively. Alternatively, the trans-membrane pressure (TMP) can be controlled at ≤2.5 bar during concentration, diafiltration, and over-concentration. The temperature of the holding tank is monitored to be ≤35° C.

After determining the protein concentration of the over-concentrated golimumab product, the remaining product is recovered from the system with a buffer flush using ≤100% of the calculated amount of diafiltration buffer needed for dilution. After determining the protein concentration of the combined recovered buffer flush and over-concentrated golimumab product, the concentration of the product is adjusted further by addition of ≤100% of the calculated amount of diafiltration buffer needed for dilution. Yield is monitored and should be ≥90%.

FB is then prepared by the addition of 1% PS 80 in 10 mM histidine, 4.5% sorbitol, pH 5.3 buffer to the concentrated and diafiltered golimumab product in a buffer to product ratio of 0.013-0.017% (w/v). After addition, the golimumab product is mixed to ensure homogeneity of the solution. The FB is sampled for analysis of bioburden and filtered using a prefilter, followed by 0.2-μm filtration into polycarbonate containers. Product samples are taken for golimumab oligosaccharide IPC testing and FB release testing. Oligosaccharide composition is analyzed by normal phase anion exchange HPLC with fluorescence detection. Before and/or after the final 0.2-μm filtration, FB can be held at 15-25° C. or at 2-8° C. for a total of ≤120 hours prior to storage at ≤−40° C.

Example 6—Application of the Gamma Distribution Transition Analysis (GDTA) Method for Chromatography Columns Used in SIMPONI® (Golimumab) Manufacturing This Example describes the application of the GDTA method to chromatography columns in purification during manufacturing of anti-TNF antibodies, e.g., the anti-TNFα antibody SIMPONI® (golimumab), e.g., a protein A affinity chromatography column in Stage 3, a cation exchange chromatography column in Stage 6, and an anion exchange chromatography column in Stage 7.

Stage 3—Protein A Affinity Chromatography Column

Figure 40:
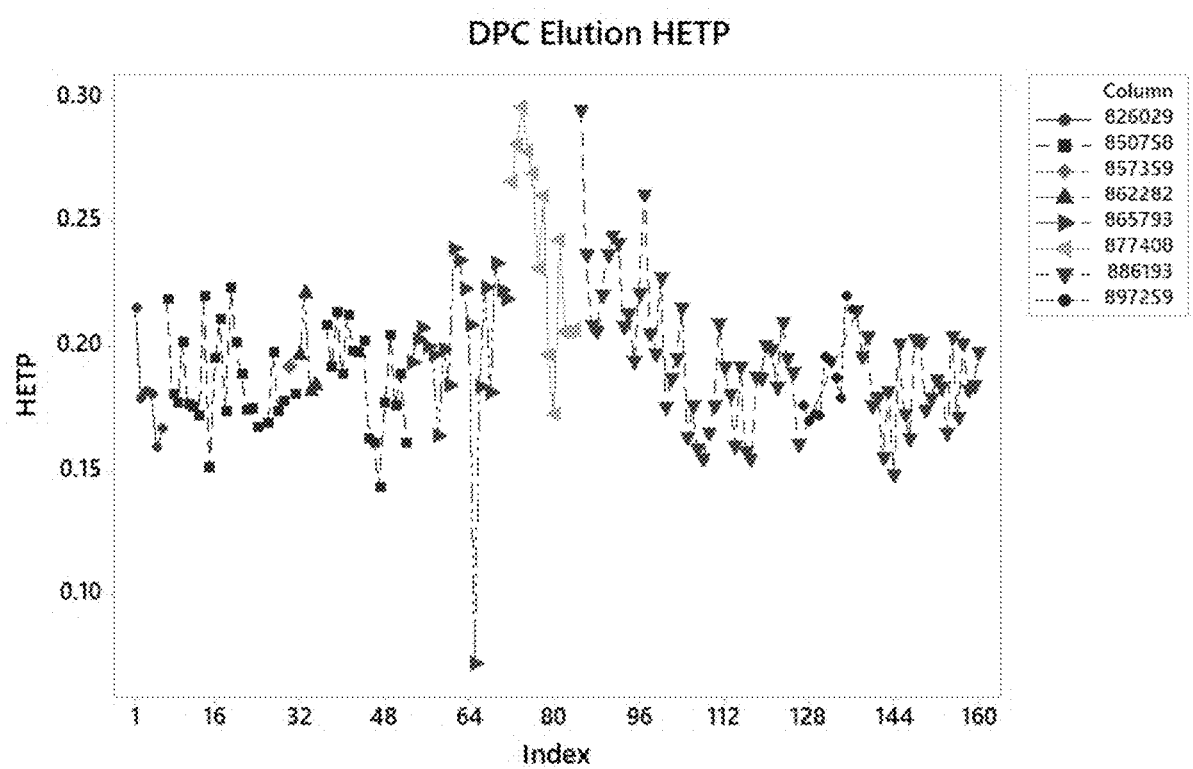
FIG. 40 is chart showing HETP results for a Stage 3 MabSelect™ Protein A affinity chromatography column for the front generated during elution of SIMPONI® (golimumab). DPC refers to Direct Product Capture of SIMPONI® (golimumab) on the MabSelect™ Protein A column.
Figure 41:
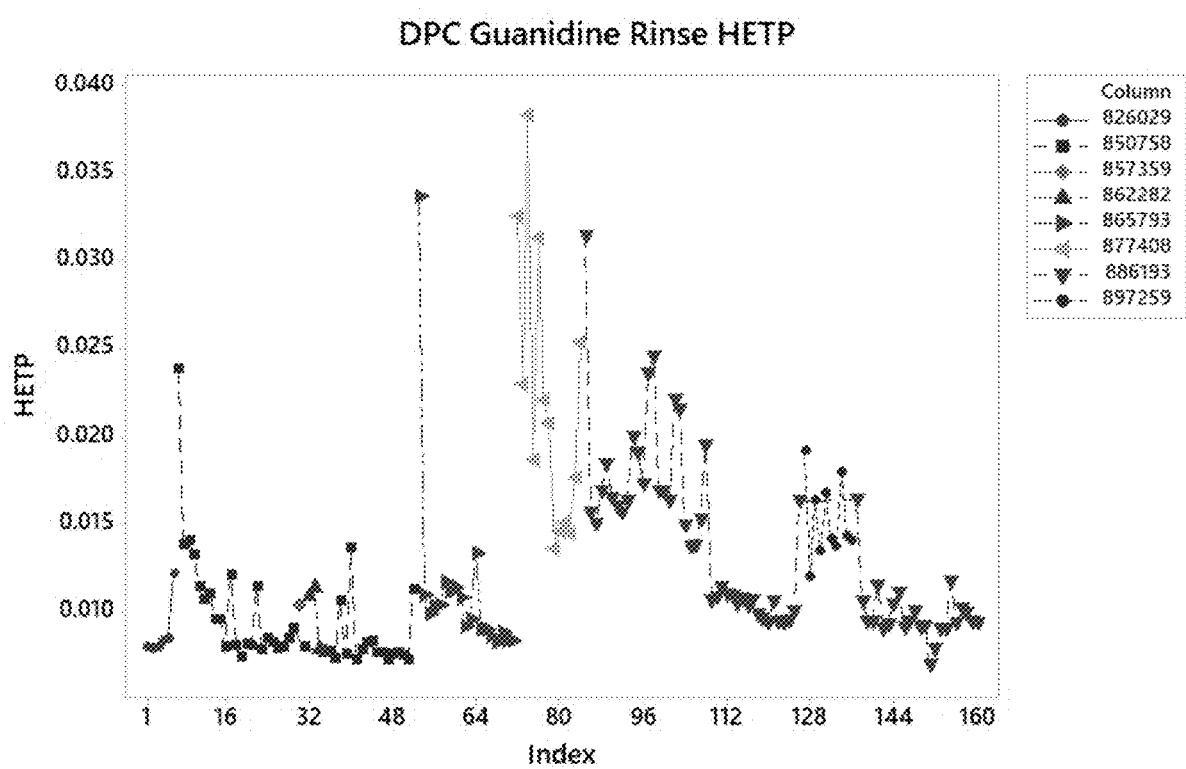
FIG. 41 is chart showing HETP results for a Stage 3 MabSelect™ Protein A affinity chromatography column for the front generated during sanitization with Guanidine HCl. DPC refers to Direct Product Capture of SIMPONI® (golimumab) on the MabSelect™ Protein A column.
Figure 42:
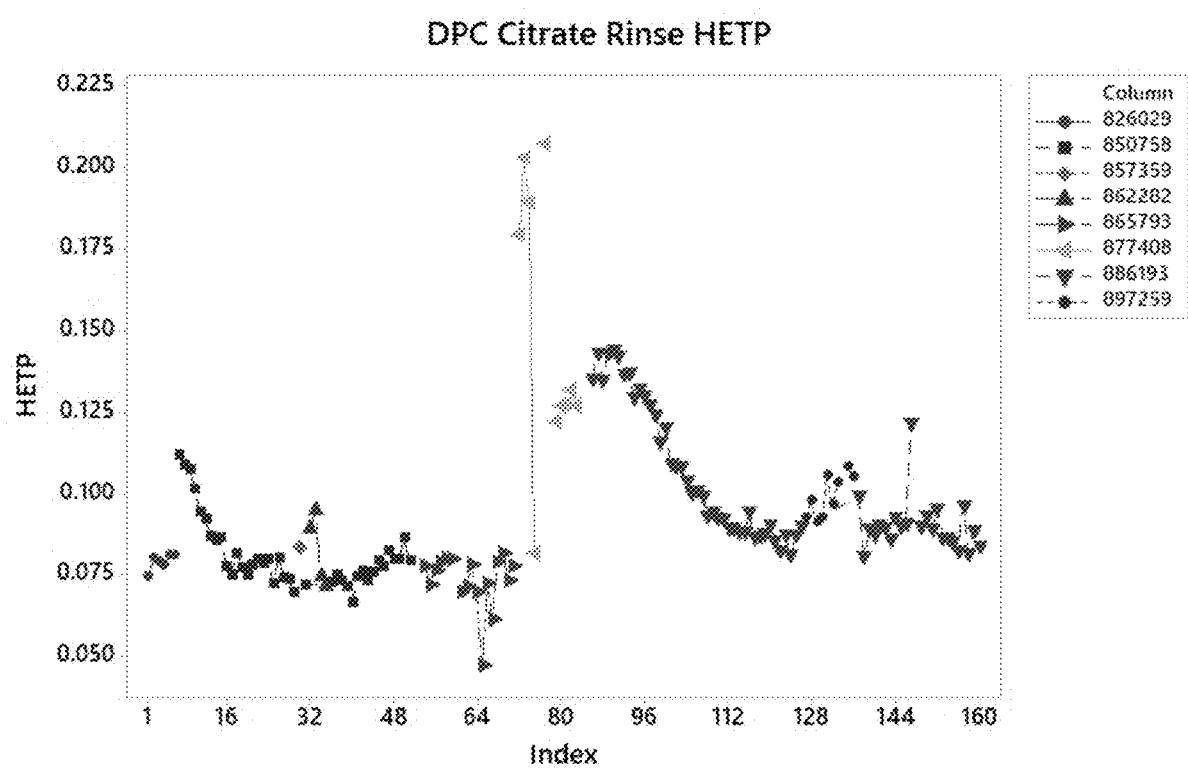
FIG. 42 is chart showing HETP results for a Stage 3 MabSelect™ Protein A affinity chromatography column for the front generated during post-sanitization rinsing with 0.1 M Sodium Citrate, pH 3.5. DPC refers to Direct Product Capture of SIMPONI® (golimumab) on the MabSelect™ Protein A column.

For the Stage 3, using a MabSelect™ Protein A affinity chromatography column, the analyzed transition fronts included, e.g., the elution front (FIG. 40), the front generated during sanitization with Guanidine HCl (FIG. 41), and the front generated during post-sanitization rinsing with 0.1 M Sodium Citrate, pH 3.5 (FIG. 42). The results shown represent the analysis of 160 batches of SIMPONI® (golimumab). Preliminary evaluation of the trends shows some drift apparent in column performance and some differences observed between column packs. A full analysis of this data, including comparison to other available batch information and column performance data will be completed in order to establish control limits for use in future implementation of the GDTA method for process monitoring in real time.

Stage 6—Cation Exchange Chromatography Column

Figure 43:
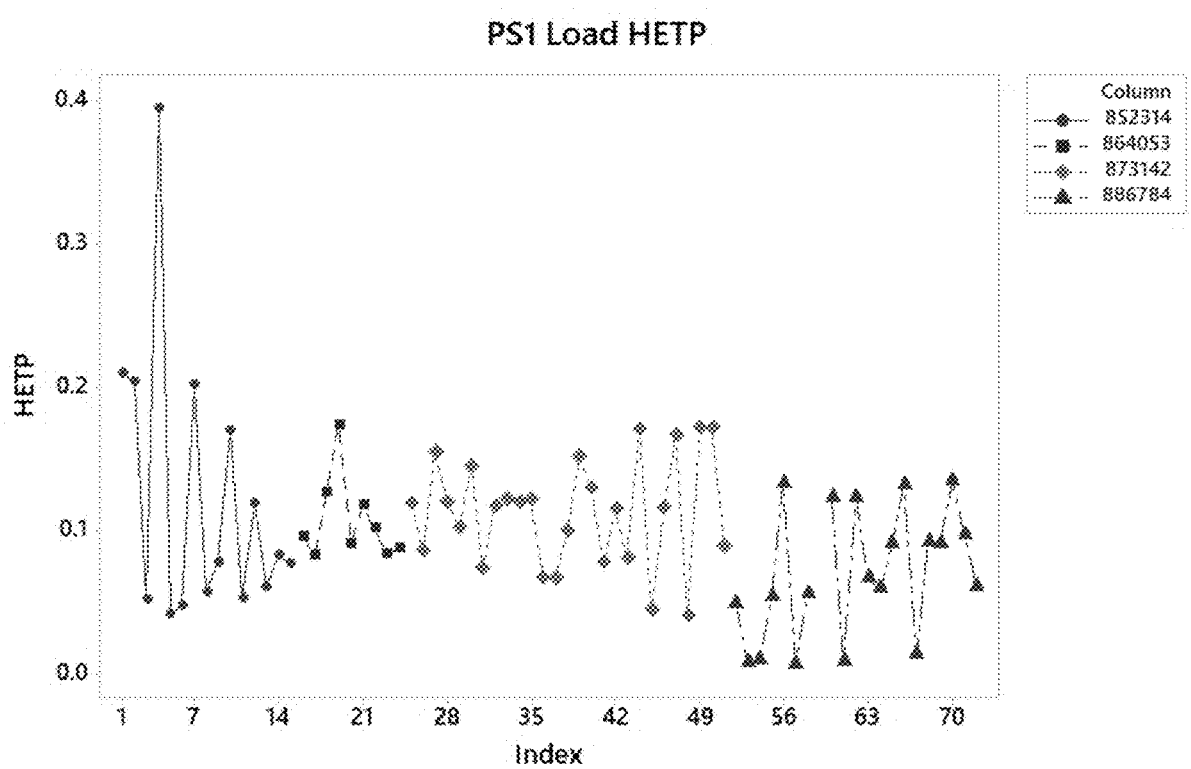
FIG. 43 is chart showing HETP results for a Stage 6 UNOsphere S™ cation exchange chromatography column front generated during loading of solvent/detergent (S/D) treated material containing SIMPONI® (golimumab). PS1 refers to Polishing Step 1 for SIMPONI® (golimumab) on the UNOsphere S™ column.
Figure 44:
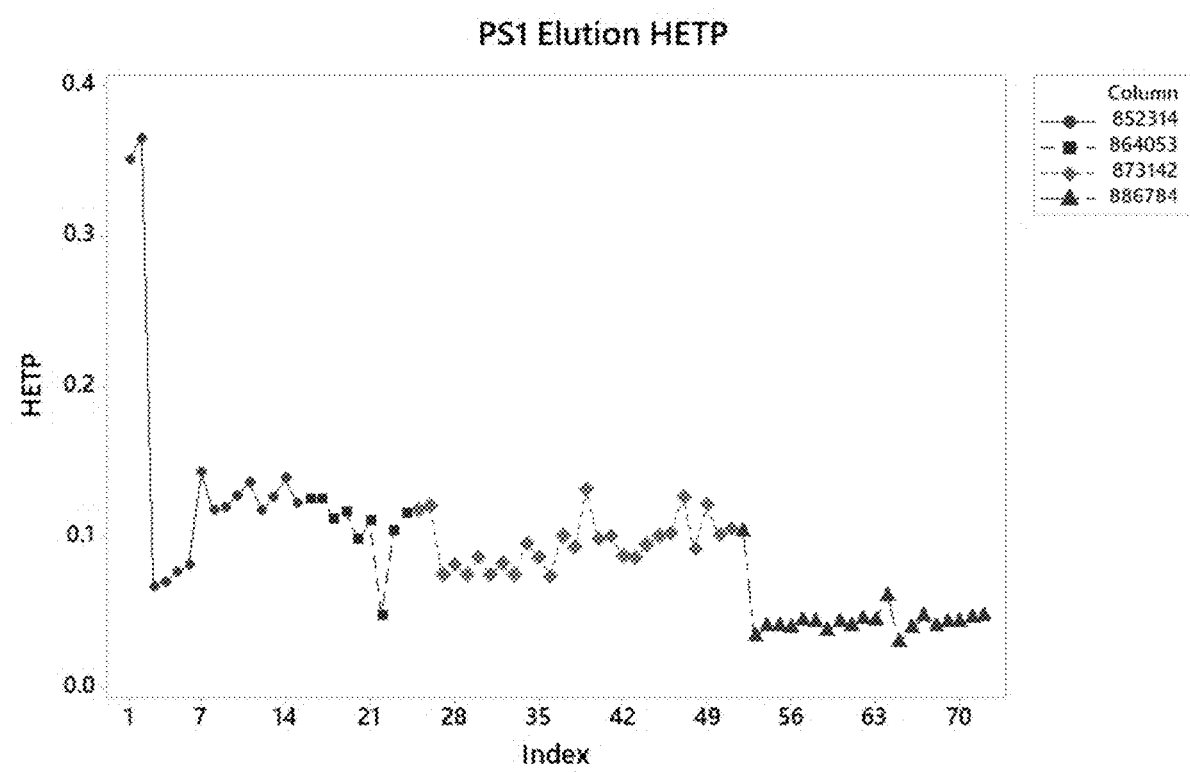
FIG. 44 is chart showing HETP results for a Stage 6 UNOsphere S™ cation exchange chromatography column front generated during elution of SIMPONI® (golimumab). PS1 refers to Polishing Step 1 for SIMPONI® (golimumab) on the UNOsphere S™ column.
Figure 45:
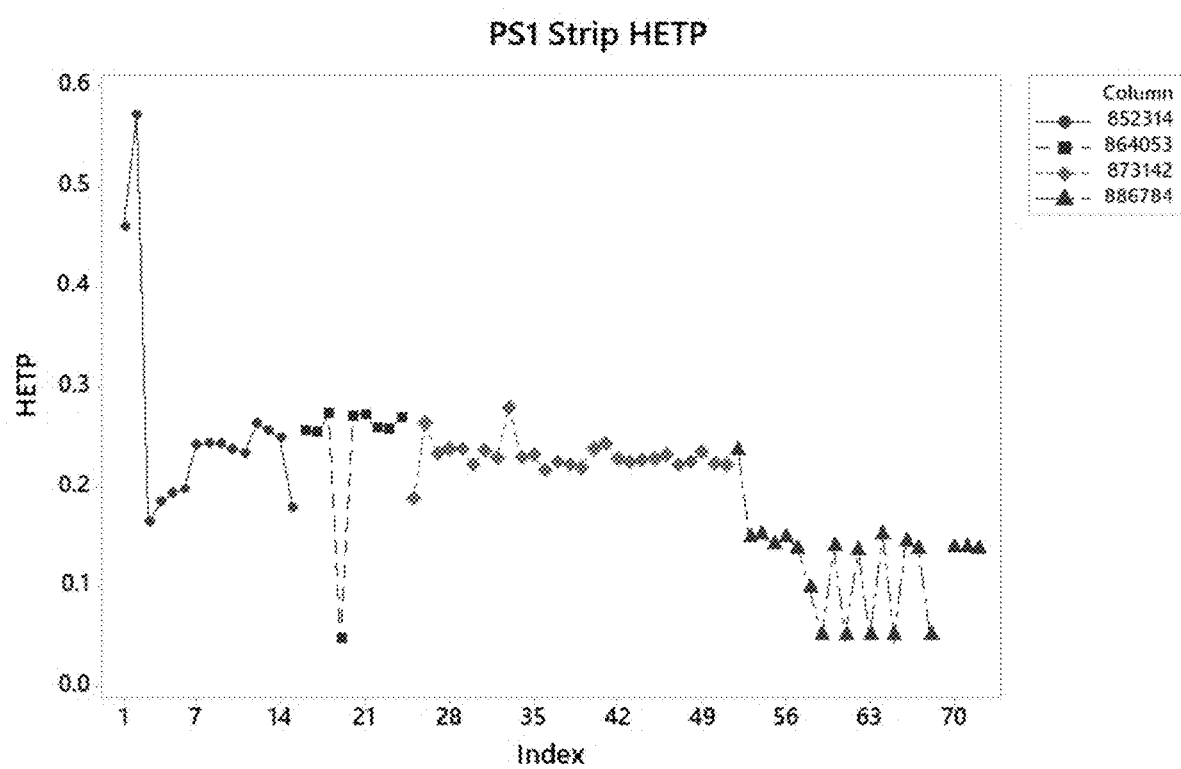
FIG. 45 is chart showing HETP results for a Stage 6 UNOsphere S™ cation exchange chromatography column front generated during the column strip. PS1 refers to Polishing Step 1 for SIMPONI® (golimumab) on the UNOsphere S™ column.

For the Stage 6, using a UNOsphere S™ cation exchange chromatography column, the analyzed transition fronts included, e.g., the front generated during loading of solvent/detergent (S/D) treated material (FIG. 43), the front generated during elution (FIG. 44), and the front generated during the strip (FIG. 45). The results shown represent the analysis of 72 batches of SIMPONI® (golimumab). Preliminary evaluation of the trends shows some drift apparent in column performance and some differences observed between column packs. A full analysis of this data, including comparison to other available batch information and column performance data will be completed in order to establish control limits for use in future implementation of the GDTA method for process monitoring in real time.

Stage 7—Anion Exchange Chromatography Column

Figure 46:
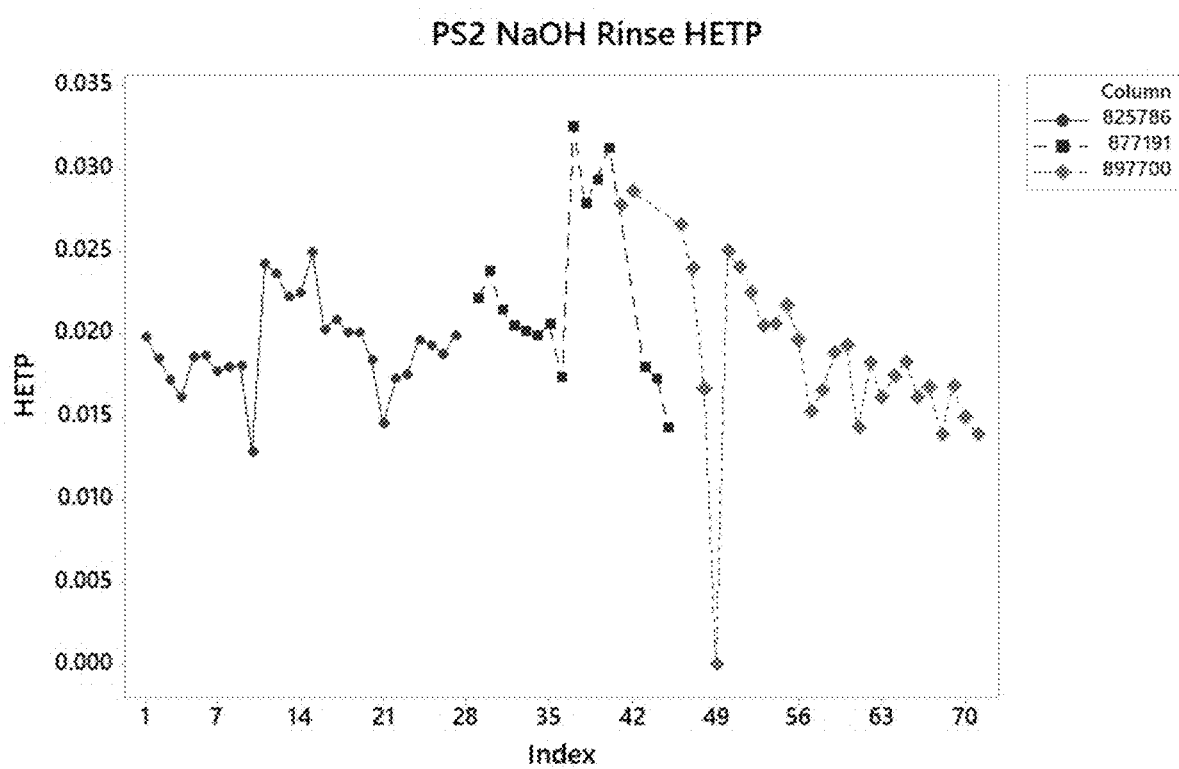
FIG. 46 is chart showing HETP results for a Stage 7 Q Sepharose™ XL anion exchange chromatography column front generated during cleaning with Sodium Hydroxide. PS2 refers to Polishing Step 2 for SIMPONI® (golimumab) on the Q Sepharose™ XL column.
Figure 47:
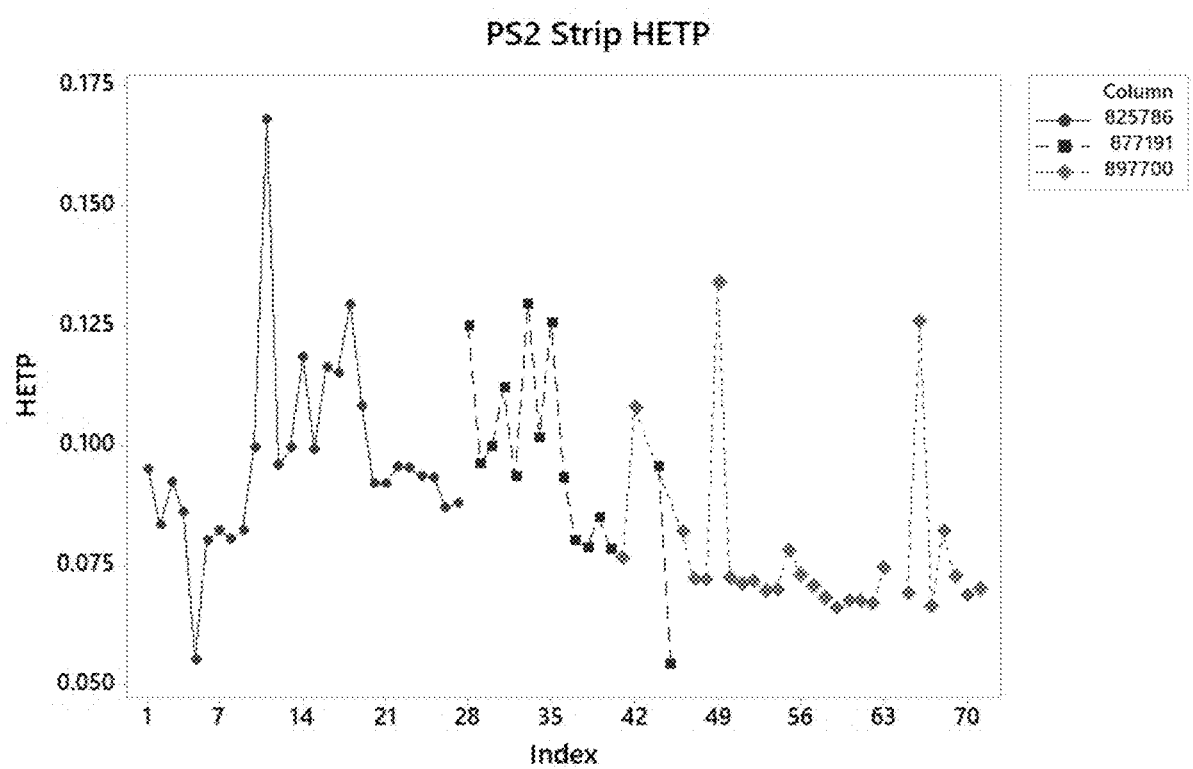
FIG. 47 is chart showing HETP results for a Stage 7 Q Sepharose™ XL anion exchange chromatography column front generated during the column strip. PS2 refers to Polishing Step 2 for SIMPONI® (golimumab) on the Q Sepharose™ XL column.

For the Stage 7, using a Q Sepharose™ XL anion exchange chromatography column, the analyzed transition fronts included, e.g., the front generated during cleaning with Sodium Hydroxide (FIG. 46) and the front generated during strip (FIG. 47). The results shown represent the analysis of 71 batches of SIMPONI® (golimumab). Preliminary evaluation of the trends shows some drift apparent in column performance and some differences observed between column packs. A full analysis of this data, including comparison to other available batch information and column performance data will be completed in order to establish control limits for use in future implementation of the GDTA method for process monitoring in real time.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of operating a chromatography column in methods of manufacture for producing anti-TNF antibodies, wherein the anti-TNF antibodies comprise a heavy chain (HC) comprising amino acid sequence of SEQ ID NO:1 and a light chain (LC) comprising amino acid sequence of SEQ ID NO:2 or an antigen binding fragment thereof, said method comprising:

collecting a column outlet signal and accumulated flow parameters at two or more intervals of at least one mobile phase transition front during a first operation of the chromatography column comprising column packing;

determining a model gamma cumulative distribution curve based on the collected column outlet signal and accumulated flow parameters for the at least one mobile phase transition front using Formula Ia for a rising transition front or Formula Ib for a falling transition front, $$C = 1 - \frac{1}{\Gamma(k)}\gamma\left(k, \frac{V - V_i}{\theta}\right) \quad \text{Formula Ia}$$

or $$C = \frac{1}{\Gamma(k)}\gamma\left(k, \frac{V - V_i}{\theta}\right) \quad \text{Formula Ib}$$

wherein C is the column outlet signal for a given V, V is the accumulated flow divided by column volume, and k, θ, and Vi are the shape, scale, and offset parameters, respectively, used to define the curve;

calculating a height equivalent theoretical plate (HETP) value for the at least one mobile phase transition front using Formula II and the model gamma cumulative distribution curve parameters of k, θ, and VI, $$HETP = \frac{\sigma^2}{\mu^2}L \quad \text{Formula II}$$

wherein
μ=kθ+V$_i$
σ=√kθ²
L=column length assessing the quality of the chromatography column packing based on said calculated HETP value;

wherein the quality of the chromatography column packing is acceptable if the calculated HETP value is above a lower control limit and below an upper control limit, wherein the lower control limit and the upper control limit are determined using a compiled trend of determined HETP values; or the method further comprises conditioning, replacing, or repacking the chromatography column to improve the quality of the chromatography column packing if the calculated HETP value is below the lower control limit or above the upper control limit.

2. The method of claim 1, the conditioning, replacing, or repacking the chromatography column based on said assessing improves the manufacture yield for producing the anti-TNF antibodies.

3. The method of claim 2 further comprising:
collecting a column outlet signal and accumulated flow parameters at two or more intervals of a corresponding mobile phase transition front during one or more subsequent uses of the chromatography column packing;
performing said determining and said calculating using the column outlet signal and accumulated flow parameters collected during each of the one or more subsequent uses of the chromatography column packing;
determining an HETP value of the chromatography column packing during each of said one or more subsequent uses based on said performing;
compiling a trend of the determined HETP values of the chromatography column packing of the one or more subsequent uses; and
identifying a change in the quality of the chromatography column packing based on said compiled trend, wherein said conditioning, replacing or repacking of the chromatography column is based on said identifying.

4. The method of claim 3, wherein an increase in the HETP value of the chromatography column packing in the one or more subsequent uses of said column packing as compared to the HETP value of the chromatography column packing in one or more earlier uses of said column packing identifies a decrease in the quality of the chromatography column packing.

5. The method of claim 2, wherein column outlet signal and accumulated flow parameters of two or more different mobile phase transition fronts during said first operation of the column packing are collected, said method comprising:
performing said determining and calculating using the column outlet signal and accumulated flow parameters collected for each of the two or more different mobile phase transition fronts independently to calculate an HETP value for each of the two of more different mobile phase transition fronts;
assessing the quality of the chromatography column packing based on the two or more calculated HETP values, whereby said conditioning, replacing or repacking of the chromatography column is based on said assessing.

6. The method of claim 1, wherein the chromatography column is selected from the group consisting of: a Protein A affinity chromatography column, a cation exchange chromatography column, and an anion exchange chromatography column.

7. The method of claim 6, wherein the Protein A affinity chromatography column comprises a Mab Select™ Protein A affinity chromatography column, the cation exchange chromatography column comprises a UNOsphere™ S cation exchange chromatography column, and the anion exchange chromatography column comprises a Q Sepharose® XL anion exchange chromatography column.

8. The method of claim 6, wherein the chromatography column is a Protein A affinity chromatography column and the at least one mobile phase transition front is generated from one or more fronts selected from the group consisting of: a front generated during an elution of the anti-TNF antibodies, a front generated during a sanitization of the column with guanidine HCl, and a front generated during a post-sanitization rinsing of the column with 0.1 M sodium citrate, pH 3.5.

9. The method of claim 6, wherein the chromatography column is a cation exchange chromatography column and the at least one mobile phase transition front is generated from one or more fronts selected from the group consisting of: a front generated during a loading of solvent/detergent (S/D) treated material comprising the anti-TNF antibodies, a front generated during an elution of the anti-TNF antibodies, and a front generated during a column strip.

10. The method of claim 6, wherein the chromatography column is an anion exchange chromatography column and the at least one mobile phase transition front is generated from one or more fronts selected from the group consisting of: a front generated during a cleaning of the column with sodium hydroxide and a front generated during a column strip.

11. The method of claim 3, wherein the chromatography column is selected from the group consisting of: a Protein A affinity chromatography column, a cation exchange chromatography column, and an anion exchange chromatography column.

12. The method of claim 11, wherein the Protein A affinity chromatography column comprises a Mab Select® Protein A affinity chromatography column, the cation exchange chromatography column comprises a UNOsphere™ S cation exchange chromatography column, and the anion exchange chromatography column comprises a Q Sepharose® XL anion exchange chromatography column.

13. The method of claim 11, wherein the chromatography column is a Protein A affinity chromatography column and the at least one mobile phase transition front is generated from one or more fronts selected from the group consisting of: a front generated during an elution of the anti-TNF antibodies, a front generated during a sanitization of the column with guanidine HCl, and a front generated during a post-sanitization rinsing of the column with 0.1 M sodium citrate, pH 3.5.

14. The method of claim 11, wherein the wherein the chromatography column is a cation exchange chromatography column and the at least one mobile phase transition front is generated from one or more fronts selected from the group consisting of: a front generated during a loading of solvent/detergent (S/D) treated material comprising anti-TNF antibodies, a front generated during an elution of the anti-TNF antibodies, and a front generated during a column strip.

15. The method of claim 11, wherein the chromatography column is an anion exchange chromatography column and the at least one mobile phase transition front is generated from one or more fronts selected from the group consisting of: a front generated during a cleaning of the column with sodium hydroxide and a front generated during a column strip.

16. The method of claim 5, wherein the chromatography column is selected from the group consisting of: a Protein A affinity chromatography column, a cation exchange chromatography column, and an anion exchange chromatography column.

17. The method of claim 16, wherein the Protein A affinity chromatography column comprises a Mab Select® Protein A affinity chromatography column, the cation exchange chromatography column comprises a UNOsphere™ S cation exchange chromatography column, and the anion exchange chromatography column comprises a Q Sepharose® XL anion exchange chromatography column.

18. The method of claim 16, wherein the chromatography column is a Protein A affinity chromatography column and the at least one mobile phase transition front is generated from one or more fronts selected from the group consisting of: a front generated during an elution of the anti-TNF antibodies, a front generated during a sanitization of the column with guanidine HCl, and a front generated during a post-sanitization rinsing of the column with 0.1 M sodium citrate, pH 3.5.

19. The method of claim 16, wherein the wherein the chromatography column is a cation exchange chromatography column and the at least one mobile phase transition front is generated from one or more fronts selected from the group consisting of: a front generated during a loading of solvent/detergent (S/D) treated material comprising anti-TNF antibodies, a front generated during an elution of the anti-TNF antibodies, and a front generated during a column strip.

20. The method of claim 16, wherein the chromatography column is an anion exchange chromatography column and the at least one mobile phase transition front is generated from one or more fronts selected from the group consisting of: a front generated during a cleaning of the column with sodium hydroxide and a front generated during a column strip.

* * * * *